US009862982B2

(12) United States Patent
Zhang et al.

(10) Patent No.: US 9,862,982 B2
(45) Date of Patent: Jan. 9, 2018

(54) METHODS OF HYDROLYZING A CELLULOSE USING HALOPHILIC, THERMOSTABLE AND IONIC LIQUIDS TOLERANT CELLULASES

(71) Applicants: The Regents of the University of California, Oakland, CA (US); Sandia Corporation, Albuquerque, NM (US)

(72) Inventors: Tao Zhang, San Diego, FL (US); Supratim Datta, Berkeley, CA (US); Blake A. Simmons, San Francisco, CA (US); Edward M. Rubin, Berkeley, CA (US)

(73) Assignees: The Regents of the University of California, Oakland, CA (US); Sandia Corporation, Albuquerque, NM (US)

( * ) Notice: Subject to any disclaimer, the term of this patent is extended or adjusted under 35 U.S.C. 154(b) by 0 days.

(21) Appl. No.: 15/164,813

(22) Filed: May 25, 2016

(65) Prior Publication Data
US 2017/0029856 A1 Feb. 2, 2017

Related U.S. Application Data

(62) Division of application No. 13/493,938, filed on Jun. 11, 2012, now Pat. No. 9,376,728.

(60) Provisional application No. 61/495,893, filed on Jun. 10, 2011.

(51) Int. Cl.
*C12P 19/14* (2006.01)
*C12P 19/02* (2006.01)
*C12N 9/42* (2006.01)

(52) U.S. Cl.
CPC ............ *C12P 19/14* (2013.01); *C12N 9/2437* (2013.01); *C12P 19/02* (2013.01); *C12Y 302/01091* (2013.01); *C12P 2201/00* (2013.01); *C12P 2203/00* (2013.01); *Y02P 20/52* (2015.11)

(58) Field of Classification Search
None
See application file for complete search history.

(56) References Cited

U.S. PATENT DOCUMENTS

2008/0227162 A1   9/2008   Varanasi et al.

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Bakke, P.; Carney, N.; Deloache, W.; Gearing, M.; Ingvorsen, K.; Lotz, M.; McNair, J.; Penumetcha, P.; Simpson, Voss, L; Win, M.; Heyer, L. J; Campbell, A. M. PLoS One 2009, 4, e6291.
Bayer, E. A.; Lamed, R.; White, B. A.; Flint, H. J. Chem Rec 2008, 8, 364.
Bose, S.; Armstrong, D. W.; Petrich, J. W. J Phys Chem B 2010, 114, 8221.
Cendrin, F.; Chroboczek, J.; Zaccai, G.; Eisenberg, H.; Mevarech, M. Biochemistry 1993, 32, 4308.
Constatinescu, D.; Herrmann, C.; Weingartner, H. Phys Chem Chem Phys 2010, 12, 1756.
Dadi, A. P.; Varanasi, S.; Schall, C. A. Biotechnol Bioeng 2006, 95, 904.
Dadi, A. P.; Schall, C. A.; Varanasi, S. Appl Biochem Biotechnol 2007, 137-140, 407.
Gao, Z.; Ruan, L.; Chen, X.; Zhang, Y.; Xu, X. Appl Microbiol Biotechnol 2010, 87, 1373.
Kamiya, N.; Matsushita, Y.; Hanaki, M.; Nakashima, K.; Narita, M.; Goto, M.; Takahashi, H. Biotechnol Lett 2008, 30, 1037.
Kataeva, I. A.; Seidel, R. D., 3rd; Shah, A.; West, L. T.; Li, X. L.; Ljungdahl, L. G. Appl Environ Microbiol 2002, 68, 4292.
Little, E.; Bork, P.; Doolittle, R. F. J Mol Evol 1994, 39, 631.
Liu, H.; Pereira, J. H.; Adams, P. D.; Sapra, R.; Simmons, B. A.; Sale, K. L. FEBS Lett 2010, 584, 3431.
Moniruzzaman, M.; Kamiya, N.; Goto, M. Org Biomol Chem 2010, 8, 2887.
Natale, P.; Bruser, T.; Driessen, A. J. M. Bba-Biomembranes 2008, 1778, 1735.
Park, S.; Kazlauskas, R. J. Cuff Opin Biotechnol 2003, 14, 432.
Pereira, J. H.; Sapra, R.; Volponi, J. V.; Kozina, C. L.; Simmons, B.; Adams, P. D. Acta Crystallogr D Biol Crystallogr 2009, 65, 744.
Rees, H. C.; Grant, S.; Jones, B.; Grant, W. D.; Heaphy, S. Extremophiles 2003, 7, 415.
Rohban, R.; Amoozegar, M. A.; Ventosa, A. J Ind Microbiol Biotechnol 2009, 36, 333.
Shill, K.; Padmanabhan, S.; Xin, Q.; Prausnitz, J.; Clark, D. S.; Blanch, H. W. Biotechnol Bioeng 2011, 108, 511-520.
Taupin, C. M.; Hartlein, M.; Leberman, R. Eur J Biochem 1997, 243, 141.
van Rantwijk, F.; Sheldon, R. A. Chem Rev 2007, 107, 2757.
Voget, S.; Steele, H. L.; Streit, W. R. J Biotechnol 2006, 126, 26.
Vreeland, R. H.; Piselli, A. F., Jr.; McDonnough, S.; Meyers, S. S. Extremophiles 1998, 2, 321.
Waino, M.; Tindall, B. J.; Ingvorsen, K. Int J Syst Evol Microbiol 2000, 50 Pt 1, 183.
Waino, M.; Ingvorsen, K. Extremophiles 2003, 7, 87.
Wu, J.; Zhang, J.; Zhang, H.; He, J.; Ren, Q.; Guo, M. Biomacromolecules 2004, 5, 266.
Wu, D.; Hugenholtz, P.; Mavromatis, K.; Pukall, R.; Dalin, E.; Ivanova, N. N.; Kunin, V.; Goodwin, L.; Wu, M.; Tindall, B. J.; Hooper, S. D.; Pati, A.; Lykidis, A.; Spring, S.; Anderson, I. J.; D'Haeseleer, P.; Zemla, A.; Singer, M.; Lapidus, A.; Nolan, M.; Copeland, A.; Han, C.; Chen, F.; Cheng, J. F.; Lucas, S.; Kerfeld, C.; Lang, E.; Gronow, S.; Chain, P.; Bruce, D.; Rubin, E. M.; Kyrpides, N. C.; Klenk, H. P.; Eisen, J. A. Nature 2009, 462, 1056.

(Continued)

*Primary Examiner* — Christian Fronda
(74) *Attorney, Agent, or Firm* — Robin C. Chiang; Lawrence Berkeley National Laboratory

(57) ABSTRACT

The present invention provides for an isolated or recombinant polypeptide comprising an amino acid sequence having at least 70% identity with the amino acid sequence of a *Halorhabdus utahensis* cellulase, such as Hu-CBH1, wherein said amino acid sequence has a halophilic thermostable and/or thermophilic cellobiohydrolase (CBH) activity. In some embodiments, the polypeptide has a CBH activity that is resistant to up to about 20% of ionic liquids. The present invention also provides for compositions comprising and methods using the isolated or recombinant polypeptide.

18 Claims, 12 Drawing Sheets

(56) References Cited

OTHER PUBLICATIONS

Zhao, H.; Olubajo, O.; Song, Z.; Sims, A. L.; Person, T. E.; Lawal, R. A.; Holley, L. A. Bioorg Chem 2006, 34, 15.
Zhou, W.; Irwin, D. C.; Escovar-Kousen, J.; Wilson, D. B. Biochemistry 2004, 43, 9655.
Zhu, S. D.; Wu, Y. X.; Chen, Q. M.; Yu, Z. N.; Wang, C. W.; Jin, S. W.; Ding, Y. G.; Wu, G. Green Chemistry 2006, 8, 325.
Datta, S.; Holmes, B.; Park, J.I.; Chen, Z.; Dibble, D.C.; Hadi, M.; Blanch, H.W.; Simmons, B.A.; Sapra, R., Green Chemistry 2010, 12, 338-345.
Chica et al., Curr Opin Biotechnol 2005, 1694):378-384.
Sen et al., Appl Biochem Biotechnol 2007, 143(3)212-223.
Accession C7NVN1. Oct. 13, 2009.
Accession C7NVN2. Oct. 13, 2009.
Accession C7NVN3. Oct. 13, 2009.
Accession C7NVN5. Oct. 13, 2009.
Accession C7NVN6. Oct. 13, 2009.
Accession C7NMC1. Oct. 13, 2009.
Accession C7NMC2. Oct. 13, 2009.
Accession C7NMC3. Oct. 13, 2009.
Accession C7NMC4. Oct. 13, 2009.
Accession C7NMC5. Oct. 13, 2009.
Accession C7NMC6. Oct. 13, 2009.
Accession C7NMC7. Oct. 13, 2009.
Accession C7NMC0. Oct. 13, 2009.
Accession C7NVN4. Oct. 13, 2009.

\* cited by examiner

Figure 8B

SEQUENCE LISTING

```
<160> NUMBER OF SEQ ID NOS: 24

<210> SEQ ID NO 1
<211> LENGTH: 709
<212> TYPE: PRT
<213> ORGANISM: Halorhabdus utahensis

<400> SEQUENCE: 1

Val Arg Val Ser Gly Ser Met Thr Asp Pro Asp Arg Pro Pro Thr Gly
1               5                   10                  15

Asp Arg Glu Ala Ser Gln Ser Asn Thr Thr Gly Gly Glu Gly Pro
            20                  25                  30

Ser Arg Arg Thr Phe Leu Lys Ser Ser Val Leu Thr Gly Ala Leu Thr
        35                  40                  45

Phe Gly Val Gly Ala Gly Ala Leu Gly Ser Ala Ser Ala Ala Ile Pro
    50                  55                  60

Thr Pro Gln Leu His Arg Asp Gly Asn Leu Ile Lys Asp Pro Asp Gly
65                  70                  75                  80

Asn Thr Val Thr Leu Arg Gly Val Asn Ile Ala Asp Pro Lys Arg Ile
```

```
            85                  90                  95
Asn Glu Thr Ala Gln Ala Arg Gly Met Thr Ala Thr Gln Val Ile Asp
            100                 105                 110
Met Leu Thr Asp Glu Ser Asn Gly Trp Tyr Pro Arg Met Ile Arg Val
            115                 120                 125
Pro Val Gln Pro Val Asp Ile Gly Glu Tyr Glu Pro Gly Ser Gly Pro
            130                 135                 140
Pro Val Pro Ala Phe Asn Glu Ser Glu Leu Glu Ser Tyr Leu Ser Asn
145                 150                 155                 160
His Leu Asp Glu Val Val Gln Arg Cys Ala Asp Arg Gly Val Tyr Cys
            165                 170                 175
Ile Ile Asp Tyr His Arg His Arg Asp Val Gln Trp Ala Glu Gly Gln
            180                 185                 190
Asp Gly Pro Val Asn Thr Glu Leu Gln Asp Glu Val Asp Met Phe Trp
            195                 200                 205
Asp Thr Val Ala Pro Arg Tyr Ala Asp Gln Ser His Val Leu Tyr Glu
            210                 215                 220
Val Tyr Asn Glu Pro Thr Glu Pro Gly Met Trp Glu Asp Pro Thr Thr
225                 230                 235                 240
Thr Gln Trp Val Ala Asp Ile Trp Gln Leu Trp Leu Glu Met Ala Gln
            245                 250                 255
Pro Trp Asp Thr Ile Arg Ser His Ala Asp Asn Leu Ile Leu Met
            260                 265                 270
Gly Ser Pro Ser Trp Ser Gln Ser Pro Glu Gly Ala Leu Val Glu Glu
            275                 280                 285
Phe Asp Gly Glu Asp Ile Ala Tyr Thr Phe His Ile Tyr Pro Gly His
            290                 295                 300
Asn Ser Ser Gln Asn Gln Asn Trp Glu Asp Ala Ser Asn Asn Gly Glu
305                 310                 315                 320
Gly Val Ala Gly Val Tyr Glu Glu Ala Pro Leu Phe Val Thr Glu Phe
            325                 330                 335
Gly Trp Glu Glu Asn Gly Gly Gln Tyr Ile Gly Gly Thr Asp Asp Phe
            340                 345                 350
Gly Thr Ala Phe Leu Asp Phe Leu Glu Lys Ser Glu Ala Ile His Trp
            355                 360                 365
Thr Ala Trp Cys Ala Asp Pro Val Trp Arg Pro Val Met Phe Ser Arg
            370                 375                 380
Pro Phe Ala Asp Asn Ala Asp Asp Ser Val Gly Asp Pro Tyr Asn Gly
385                 390                 395                 400
Thr Val Pro Glu Ala Cys Ser Glu Leu Pro Cys Glu Trp Glu Leu Thr
            405                 410                 415
Thr Gly Ser Gly Tyr Met Gly Asp Val Lys Ser Ala Leu Glu Gln
            420                 425                 430
Tyr Arg Asn Asp Gly Ile Pro Gly Glu Gly Thr Gly Asn Gly Asp Asp
            435                 440                 445
Asp Asp Asp Asp Gly Asp Thr Gln Ala Pro Ser Ala Pro Ser Asn Val
            450                 455                 460
Ser Val Ala Ser Thr Ser Glu Thr Ser Val Glu Val Thr Trp Ser Ala
465                 470                 475                 480
Ser Thr Asp Ser Gly Gly Ser Gly Leu Asp Ser Tyr Val Val Thr Val
            485                 490                 495
Asp Gly Ser Glu Asp Gln Thr Val Pro Ala Gly Thr Thr Ser Ala Thr
            500                 505                 510
```

Ile Asp Gly Leu Ser Ala Gly Thr Thr Tyr Gln Ile Ala Val Ala Ala
        515                 520                 525

Val Asp Gly Ala Gly Asn Glu Ser Ala Ala Thr Thr Val Glu Ala Thr
    530                 535                 540

Thr Asp Glu Thr Asp Asp Gly Glu Asp Gly Gln Asp Asp Gly Asp Asp
545                 550                 555                 560

Glu Ala Pro Ala Asp Ala Leu Ile Val Asn Asp Tyr Asp Gly Asp Pro
                565                 570                 575

Ala Trp Ser Ser Asn Arg Asn Asp Leu Gly Gln Trp Cys Gly Ala Gly
            580                 585                 590

Ser Phe Glu Asn Asp Gly Gly Asp Val Gln Asp Gly Ala Leu Thr Leu
        595                 600                 605

Glu Tyr Asp Asn Gly Gly Trp Phe Val Glu Gln Leu Gly Gln Asp Val
    610                 615                 620

Ser Glu Tyr Ser Glu Ala Val Leu Arg Val Arg Gly Ala Asn Gly Gly
625                 630                 635                 640

Glu Glu Asp Glu Phe Ile Phe Asp Met Gly Gly Ala Arg Asp Ile Leu
                645                 650                 655

Ser Asn Leu Thr Asp Asp Ser Ile Ser Thr Ser Phe Ser Asn Val Thr
            660                 665                 670

Ile Asp Leu Glu Ser Ala Gly Ile Asp Pro Ser Ala Gly Gly Leu Ser
        675                 680                 685

Val Arg Leu Asn Phe Trp Gln Gly Gly Ser Thr Leu Glu Ile Glu
    690                 695                 700

Glu Ile Arg Leu Gln
705

<210> SEQ ID NO 2
<211> LENGTH: 768
<212> TYPE: PRT
<213> ORGANISM: Halorhabdus utahensis

<400> SEQUENCE: 2

Met Thr Asp Asn Asp Thr Tyr Asp Gly Gly Glu Ser Thr Thr Asn Asp
1               5                   10                  15

Ser Arg Ile Ile Asp Asp Val Ser Arg Arg Asp Val Leu Lys Ala Ala
            20                  25                  30

Gly Ala Ser Ala Leu Thr Ala Gly Phe Ala Ser Ser Ile Val Gly Ser
        35                  40                  45

Val Ser Ala Ala Gly Ile Pro Thr Pro Trp Leu Glu Arg Asp Gly Asn
    50                  55                  60

Leu Leu Arg Asp Pro Asp Gly Asn Gln Val Ile Leu Arg Gly Val Asn
65                  70                  75                  80

Met Ala Asp Pro Ala Arg Leu Ala Arg Ser Trp Arg Ser Lys Asp Ser
                85                  90                  95

Met Gly Val Phe Asp Lys Ala Thr Asn Thr Asp Glu Ser Asn Asp Gly
            100                 105                 110

Gly Trp His Asn Asn Ile Leu Arg Val Pro Thr Gln Pro Gln Asp Ile
        115                 120                 125

Gly Asp Ala Gly Ser Gly Ser Ile Gly Ser Met Pro His Gly Asp Asp
    130                 135                 140

Trp Gly Pro Leu Leu Pro Gly Gln Ile Asp Glu Ser Asp Leu Glu Thr
145                 150                 155                 160

Tyr Phe Ser Asp Tyr Ile Asp Pro Ile Val Asp Ala Ala Glu Glu Glu

```
                165                 170                 175
Gly Leu Tyr Val Met Ile Asp Tyr His Arg His Phe Pro Ile Phe His
                    180                 185                 190
Gln Pro Gln His Glu Glu Asp Leu Gly Asp Tyr Gln Cys Gly Asn Glu
                    195                 200                 205
Ser Phe Glu Asn Asp Ile Gly Phe Cys Gly Glu Arg Gly Val Leu Trp
            210                 215                 220
His Ser Glu Glu Gln Ala Ser Gln Leu Asp Gly Tyr Thr Glu Tyr
225                 230                 235                 240
Ala Ala Glu Leu Asn Gln Glu Leu Gln Met Tyr Trp Asn Phe Val Ala
                245                 250                 255
Pro Arg Tyr Asn Asp Arg Ser His Val Val Tyr Asp Ile Tyr Asn Glu
                260                 265                 270
Pro Thr Gly Pro Tyr Ala Gly Asp Trp Gly Ser Pro Thr Glu Leu Pro
                275                 280                 285
Ala Thr Gly Glu Glu Gly Glu Glu Asn Pro Ser Tyr Asp Ala Asp Ala
            290                 295                 300
Asn Gln Glu Tyr Trp Asp Met Trp Val Asp Arg Ala Gln Pro Trp Val
305                 310                 315                 320
Asp Thr Val Arg Glu His Ala Pro Asp Asn Leu Ile Thr Ile Gly Ser
                325                 330                 335
Pro Arg Trp Ser Gln Leu Thr Tyr Trp Ala Pro Thr Asn Glu Phe Asp
                340                 345                 350
Gly Glu Asn Ile Cys Tyr Thr Gly His Val Tyr Thr His Glu Gly Met
            355                 360                 365
Arg Pro Leu Ser Asp Ser Phe Gly Thr Ala Ala Glu Glu Val Pro Met
        370                 375                 380
Phe Phe Ser Glu Phe Gly Trp Ala Glu Gly Gly Arg Asp Gly Phe
385                 390                 395                 400
Ser Phe Leu Glu Gly Thr Thr Ser Glu Tyr Ala Asp Gly Phe Glu Thr
                405                 410                 415
Phe Leu Asp Glu Tyr Pro Val His Pro Ile Cys Trp Asn Phe Asp His
                420                 425                 430
Thr Trp Glu Pro Ser Phe Phe Val His Asp Glu Ser Gln Asp Gly Asp
            435                 440                 445
Trp Val Ile His Asp Tyr Glu Ala Arg Pro Ala Gln Trp Trp Gln Glu
        450                 455                 460
Tyr Leu Tyr Glu Asn Arg Asn Asp Asp Leu Pro Gly Ser Gly Gly Asp
465                 470                 475                 480
Asp Asp Asp Thr Thr Ala Pro Ser Ile Pro Ser Asn Leu Thr Val Thr
                485                 490                 495
Asp Glu Thr Ser Ser Ile Thr Val Ser Trp Ser Ala Ser Thr Asp
            500                 505                 510
Ser Gly Thr Ala Gly Leu Ala Gln Tyr Asn Val Leu Val Asp Gly Ser
        515                 520                 525
Leu Glu Gln Thr Val Ser Ala Gly Thr Thr Ser Ala Thr Ile Ser Gly
    530                 535                 540
Leu Ala Ala Asp Thr Ser Tyr Gln Ile Ala Val Ser Ala Glu Asp Gly
545                 550                 555                 560
Ala Gly Asn Thr Ser Gly Thr Thr Ile Thr Ala Asp Thr Asp Ala
                565                 570                 575
Gly Ser Asp Asp Gly Asp Thr Gln Ala Pro Ser Ala Pro Ser Asn Val
            580                 585                 590
```

```
Ser Val Glu Ser Thr Thr Glu Thr Ser Val Glu Val Ser Trp Ser Ala
            595                 600                 605

Ser Thr Asp Ser Gly Gly Ser Gly Leu Asp Ser Tyr Val Val Ser Val
            610                 615                 620

Asp Gly Ser Gln Asp Arg Thr Val Pro Ala Gly Thr Thr Ser Ala Thr
625                 630                 635                 640

Val Asp Gly Leu Ser Ala Gly Thr Ser Tyr Gln Ile Gly Val Ser Ala
            645                 650                 655

Val Asp Gly Ala Gly Asn Glu Ser Ala Ala Thr Thr Val Gly Ala Thr
            660                 665                 670

Thr Ser Glu Ser Asp Asp Asp Gly Thr Ser Gly Glu Pro Ile Ala
            675                 680                 685

Thr Ile Asp Pro Gly Thr Thr Ser Ala Ser Thr Gly Asp Leu Val Gln
            690                 695                 700

Phe Trp Ile Ser Asp Glu Thr Gly Asn Gln Thr Trp Ile Thr Gly Leu
705                 710                 715                 720

Glu Trp Glu Leu Gly Asn Gly Thr Thr Gly Arg Gly Trp Tyr Thr Asp
            725                 730                 735

Glu Arg Tyr Gln Ser Thr Gly Thr Tyr Thr Val Thr Leu Thr Ala Thr
            740                 745                 750

Asn Asn Glu Gly Glu Thr Ser Thr Asp Glu Val Glu Val Thr Ile Ser
            755                 760                 765

<210> SEQ ID NO 3
<211> LENGTH: 507
<212> TYPE: PRT
<213> ORGANISM: Halorhabdus utahensis

<400> SEQUENCE: 3

Met Thr Arg Asp Asp Thr Asp Glu Pro Thr Gly Glu Ser Thr Thr Ser
1               5                   10                  15

Ala Thr Thr Thr Asp Ser Gly Gly Arg Ser Arg Asp Arg Pro Ser Val
            20                  25                  30

Ser Ala Gln Thr Arg Arg Arg Phe Leu Leu Thr Gly Ala Gly Val Gly
            35                  40                  45

Leu Gly Ala Leu Ala Leu Asn Ala Ser Gly Pro Ala Ser Ala Ala Thr
        50                  55                  60

Val Glu Glu Val Cys Asn Ser Asp Asp Tyr Gly Ser Ile Asp Val Ala
65                  70                  75                  80

Asp Gly Phe Thr Leu Val Asp Asn Gln Trp Gly Asn Ser Asn Ala Asp
                85                  90                  95

Gln Cys Val Trp Leu Asn Asp Asp Gly Ser Tyr Gly Tyr Asp Phe Asp
            100                 105                 110

Ala Ala Gly Gly Ser Gly Ile Asn Tyr Pro Glu Val Ile Cys Gly Thr
        115                 120                 125

Lys Pro Trp Gly Thr Asp Thr Gly Val Ala Glu Phe Pro Ile Arg Arg
130                 135                 140

Arg Asp Val Asp Glu Leu Val Ile Asp Val Glu Ala Glu Tyr Ser Glu
145                 150                 155                 160

Ser Gly Gly Glu Trp Asp Trp Ala Glu Glu Trp Trp Leu Met Asp Gln
                165                 170                 175

Pro Pro Ser Gln Glu Thr Gly Thr His Gln Tyr Glu Ile Met Leu Leu
            180                 185                 190

Leu Asp Trp Asn Asp Gln His Asp His Gly Ala Val Glu Ala Glu Asn
```

```
                    195                 200                 205
Val Trp Thr Asp Arg Phe Gly Asn Thr Val Asp His Trp Thr Thr Tyr
210                 215                 220
Asn Ser Gly Gly Thr Asn Ala Thr Phe Tyr Ile Phe Arg Ile Gln Gly
225                 230                 235                 240
Gly His Asp Gly Gly Arg Ile Asp Leu Thr Glu Ile Val Asp Tyr Leu
                245                 250                 255
Thr Ala Glu His Gly Val Asp Glu Ser Leu Trp Leu Ser Gly Val Glu
                260                 265                 270
Leu Gly Asn Glu Tyr Trp Glu Gly Ser Ser Gly Glu Thr Thr Tyr Asn
                275                 280                 285
Thr Phe Asp Val Thr Ile Asn Gly Ser Thr Tyr Glu Ser Gly Ser Gly
                290                 295                 300
Thr Asp Thr Pro Thr Pro Thr Glu Thr Pro Thr Pro Thr Glu Thr Pro
305                 310                 315                 320
Thr Pro Thr Glu Thr Pro Thr Asp Thr Glu Thr Glu Thr Pro Thr Asp
                325                 330                 335
Thr Glu Thr Glu Thr Pro Thr Asp Thr Glu Thr Glu Thr Pro Thr Asp
                340                 345                 350
Thr Glu Thr Glu Thr Glu Thr Pro Ser Gly Asp Ala Leu Val Val Asn
                355                 360                 365
Asp Tyr Asp Gly Asp Pro Ala Trp Ser Ser Asn Arg Asn Asp Leu Gly
370                 375                 380
Gln Trp Cys Gly Ala Gly Ser Phe Glu Asn Gly Ser Gly Asp Val Gln
385                 390                 395                 400
Asp Gly Ala Leu Val Leu Glu Tyr Asp Asn Ala Gly Trp Phe Gln Glu
                405                 410                 415
Gln Ile Asn Gln Asp Leu Ser Gly Tyr Ser Asp Leu Val Phe Val Leu
                420                 425                 430
Ser Gly Ala Asp Gly Gly Glu Glu Asp Asp Phe Leu Leu Asp Val Gly
                435                 440                 445
Gly Ala Arg Gly Leu Leu Ser Ala Phe Ser Asp Asp Ala Ile Gly Thr
                450                 455                 460
Ser Ala Ser Thr Val Thr Val Asp Met Glu Ser Ala Gly Ile Asp Pro
465                 470                 475                 480
Ser Ala Gly Gly Leu Ser Val Arg Leu Asn Phe Trp Gln Gly Gly Ser
                485                 490                 495
Gly Thr Leu Glu Ile Asp Glu Ile Arg Phe Glu
                500                 505

<210> SEQ ID NO 4
<211> LENGTH: 523
<212> TYPE: PRT
<213> ORGANISM: Halorhabdus utahensis

<400> SEQUENCE: 4

Met Thr Arg Arg Thr Asn Asp Thr Gly Glu Val Asp Glu Lys Pro Ser
1               5                   10                  15
Ser Gly Ala Glu Gln Gln Gly Ser Asn Asp Ser Thr Gly Ser Arg Asp
                20                  25                  30
Pro Ser Arg Arg Asp Phe Leu Lys Ala Gly Ala Val Gly Ala Gly
                35                  40                  45
Thr Phe Ala Val Gly Leu Gly Gln Gln Ala Thr Ala Thr Thr Ala Thr
                50                  55                  60
```

```
Asp Pro Ser Asn Leu Asp Leu Tyr Leu Leu Phe Gly Gln Ser Asn Met
 65                  70                  75                  80

Glu Gly Gln Gly Pro Ile Glu Ala Gln Asp Arg Glu Thr His Pro Arg
                 85                  90                  95

Ile His Val Leu Ala Asp Lys Thr Cys Pro Asn Leu Asp Arg Glu Tyr
            100                 105                 110

Gly Glu Trp Tyr Leu Ala Glu Pro Leu Asn Arg Cys Tyr Gly Lys
        115                 120                 125

Leu Gly Pro Gly Asp Tyr Phe Ala Lys Ser Met Ile Glu Glu Met Pro
    130                 135                 140

Asp Asp Arg Ser Ile Gly Leu Val Pro Ala Ala Val Ser Gly Ala Asp
145                 150                 155                 160

Ile Ala Leu Phe Glu Lys Gly Ala Pro Ile Gly Arg Asn Asp Arg Asp
                165                 170                 175

Ile Pro Ser Gln Phe Asp Gly Gly Tyr Glu Trp Met Val Asp Leu Ala
            180                 185                 190

Glu Thr Ala Gln Gln Val Gly Thr Phe Arg Gly Ile Leu Phe His Gln
        195                 200                 205

Gly Glu Thr Asn Thr Asn Asp Gln Gln Trp Thr Asp Gln Val Gln Gly
    210                 215                 220

Ile Val Glu Asp Leu Arg Ala Asp Leu Gly Ile Gly Asn Val Pro Phe
225                 230                 235                 240

Leu Ala Gly Glu Met Leu Tyr Asp Ser Ala Gly Cys Cys Gly Ser
                245                 250                 255

His Asn Thr Glu Val Asn Glu Leu Pro Asp Val Ile Glu Asn Ala His
            260                 265                 270

Val Val Ser Ala Glu Gly Leu Ala Gly Gln Asp Tyr Ala His Phe Thr
        275                 280                 285

Ser Glu Ala Tyr Arg Glu Leu Gly Arg Arg Tyr Ala Ala Glu Met Leu
    290                 295                 300

Glu His Val Asp Val Ser Gly Gly Thr Asp Asp Gly Ser Gly Gly Asn
305                 310                 315                 320

Ser Gly Asp Asp Ser Gly Gly Asn Asp Gly Asp Gly Ser Gly Ser Asp
                325                 330                 335

Ser Asp Asp Asp Ser Asp Ser Asp Thr Gly Asp Ser Gly Asp Asp Ser
            340                 345                 350

Gly Ser Asp Thr Gly Asp Ser Ser Gly Asp Asp Ala Gly Ser Asp Ser
        355                 360                 365

Gly Gly Ser Ser Glu Tyr Pro Thr Trp Asp Ser Thr Ala Val Tyr Arg
    370                 375                 380

Thr Gly Asp Arg Val Val His Asp Gly Arg Val Trp Glu Ala Gln Trp
385                 390                 395                 400

Tyr Thr Gln Asp Gln Glu Pro Arg Glu Glu Asp Tyr Tyr Val Trp Gln
                405                 410                 415

Pro Val Glu Asp Glu Ser Ala Gly Asn Ser Gly Gly Asp Thr Ser Gly
            420                 425                 430

Glu Ser Gly Gly Asp Thr Gly Asn Leu Asn Ala Glu Met Asp Pro Ser
        435                 440                 445

Thr Thr Ala Ala Ser Val Gly Glu Arg Val Thr Phe Arg Val Thr Asp
    450                 455                 460

Thr Ser Gly Ser Ser Asn Trp Leu Thr Ser Leu Ala Phe Asp Phe Gly
465                 470                 475                 480

Asp Gly Met Thr Ala Thr Gly Trp Trp Ala Ala His Ser Phe Asp Ser
```

```
                    485                 490                 495
Pro Gly Thr Tyr Thr Val Thr Leu Thr Ala Thr Asp Asn Gly Gly Ala
                500                 505                 510

Ser Thr Thr His Glu Val Thr Ile Thr Val Ser
            515                 520

<210> SEQ ID NO 5
<211> LENGTH: 771
<212> TYPE: PRT
<213> ORGANISM: Halorhabdus utahensis

<400> SEQUENCE: 5

Val Thr Asp Pro Arg Pro Thr Ser Pro Ser Gly Asp Arg Asp Arg Arg
 1               5                  10                  15

Ala Gln His Thr Thr Ile Pro Met Thr Pro Asp Thr Asn Asp Asp Ile
                20                  25                  30

Asp Thr Ser Thr Ala Gly Pro Val Glu Ala Asp Ser Val Gly Ser
            35                  40                  45

Met Asp Arg Arg Asp Tyr Leu Gln Thr Val Ala Ala Ala Ala Ala
    50                  55                  60

Ala Gly Leu Gly Ala Ala Thr Thr Gly Gly Ala Ala Glu Thr Ala
65                  70                  75                  80

Asp Thr Ser Leu Ser Ile Asp Glu Arg Ile Glu Glu His Arg Thr Gly
                85                  90                  95

Thr Leu Glu Val Val Val Glu Asn Pro Asp Gly Ser Thr Val Ser Asp
                100                 105                 110

Ala Glu Val Ser Ile Ala Gln Gln Glu His Ala Phe Ser Phe Gly Thr
            115                 120                 125

Ala Val Asn Ala Asp Arg Leu Val Asn Glu Ser Asp Pro Gly Asp Asn
        130                 135                 140

Tyr Arg Glu Tyr Val Pro Glu Leu Phe Asn Thr Ala Val Leu Gly Asn
145                 150                 155                 160

His His Lys Trp Arg Phe Trp Glu Asn Asn Arg Glu Val Ala Asp Glu
                165                 170                 175

Ala Thr Asn Trp Leu Leu Asp Gln Gly Leu Asp Met Arg Gly His Val
            180                 185                 190

Cys Leu Trp Gly Arg Glu Asp Val Ala Ala Ile Pro Asp Asp Ile Leu
        195                 200                 205

Thr Ala Ile Glu Glu Arg Asp Ala Glu Thr Ile Arg Glu Arg Ser Met
210                 215                 220

Ala His Ile Glu Glu Ile Ile Thr His Tyr Gly Glu Asp Ile Thr Asp
225                 230                 235                 240

Trp Asp Val Val Asn Glu Ala Met His Ala Tyr Gln Leu Gln Leu Gly
                245                 250                 255

Val Tyr Gly Asp Arg Ile Asp Thr Glu Glu Pro Trp Asn Gly Glu Ile
            260                 265                 270

Val Pro Trp Thr Ser Pro Leu Leu Ala Ala Trp Tyr Glu Gln Ala Ala
        275                 280                 285

Ser Val Ile Ala Glu His Asp Leu Asp Val Gly Ile Ala Val Asn Asp
    290                 295                 300

Phe Asn Gln Phe Pro Tyr Ala Tyr Thr Asp Asn Arg Tyr Glu Ser Glu
305                 310                 315                 320

Ile Asp His Ile Asn Ala Asn Gly Ala Gln Leu Asp Thr Val Gly Leu
                325                 330                 335
```

-continued

```
Gln Ala His Ile Ala Ala Arg Glu Gly Phe Asn Ser Asn Asp Asp
            340                 345                 350

Pro Asp Gly Arg Ile Asp Ala Asp Gln Val Val Ser Glu Ile Asn Thr
        355                 360                 365

Trp Ala Asp His Gly Ala Arg Val Lys Ile Thr Glu Phe Asp Thr Tyr
        370                 375                 380

Asn Gly Asp Asp Trp Asn Ser Asp Glu Glu Arg Ala Asp Val Thr Glu
385                 390                 395                 400

Asn Tyr Leu Arg Gly Ala Phe Ser His Pro Gly Val Asp Ala Phe Ile
                405                 410                 415

Met Trp Gly Phe Trp Asp Gly Asp His Trp Glu Asp Glu Ala Pro Leu
            420                 425                 430

Phe Tyr Glu Asp Trp Ser Gln Lys Pro Ala Tyr Asp Val Trp Thr Gly
            435                 440                 445

Leu Val Tyr Asp Glu Trp Trp Thr Asp Asp Ser Gly Thr Thr Asp Ser
        450                 455                 460

Arg Gly Ala Tyr Thr Thr Thr Ala Phe Leu Gly Asp His Glu Val Thr
465                 470                 475                 480

Val Ser Thr Asp Ser Ala Glu Thr Thr Glu Ser Val Glu Val Thr Asp
                485                 490                 495

Ala Ser Gly Thr Thr Thr Val Thr Val Thr Val Ala Gly Asp Gly Ser
            500                 505                 510

Ala Ala Asp Asp Thr Gln Pro Pro Ser Val Pro Thr Asn Leu Ser Val
            515                 520                 525

Ser Thr Thr Thr Asp Ser Thr Val Thr Val Ser Trp Asp Gly Val Thr
        530                 535                 540

Asp Asn Gly Thr Ala Gly Leu Asp Gln Tyr Val Val Ser Val Gly Gly
545                 550                 555                 560

Ser Gln Asp Gln Thr Ile Gly Ala Gly Met Thr Thr Ala Thr Val Glu
                565                 570                 575

Gly Leu Asp Ala Ala Ala Thr Tyr Glu Ile Gly Val Ser Ala Val Asp
            580                 585                 590

Ser Ala Gly Asn Glu Ser Asp Ala Ala Thr Val Gln Ala Thr Thr Ala
        595                 600                 605

Glu Ala Asp Asp Gly Glu Asp Asp Glu Gly Asp Gly Thr Asp Asp Glu
        610                 615                 620

Thr Pro Ala Glu Ala Leu Val Val Asn Asp Tyr Asp Gly Asp Pro Ala
625                 630                 635                 640

Trp Ala Ser Asn Arg Asn Asp Leu Gly Gln Trp Cys Gly Ala Gly Ser
                645                 650                 655

Phe Glu Asn Gly Gly Gly Glu Val Glu Asp Gly Ala Leu Val Leu Glu
            660                 665                 670

Tyr Asp Asn Ala Gly Trp Phe Val Glu Gln Leu Asn Gln Asp Val Ser
        675                 680                 685

Glu Tyr Ser Glu Leu Val Leu Val Leu Ala Gly Asp Asp Val Gln Ala
        690                 695                 700

Asp Glu Phe Leu Leu Asp Val Gly Gly Ala Arg Gly Leu Leu Ser Ala
705                 710                 715                 720

Phe Thr Asp Asp Ala Ile Gly Thr Ser Ala Ser Thr Val Thr Val Asp
                725                 730                 735

Met Glu Ser Ala Gly Ile Asp Pro Ser Thr Gly Gly Leu Ser Val Arg
            740                 745                 750

Leu Asn Phe Trp Gln Gly Gly Ser Gly Thr Leu Glu Ile Glu Glu Ile
```

Arg Phe Gln
    770

<210> SEQ ID NO 6
<211> LENGTH: 831
<212> TYPE: PRT
<213> ORGANISM: Halorhabdus utahensis

<400> SEQUENCE: 6

Met Thr His Asp Asp Ser His Asp Ile Asp Ala Ser Ala His Glu Ser
1               5                   10                  15

Asp Asp Val His Asp Ala Ser Glu Pro Thr Thr Asp Gly Glu Gly Pro
            20                  25                  30

Ala Gly Ser Met Glu Arg Arg Asp Tyr Leu Arg Ala Val Ala Ala Ala
        35                  40                  45

Ala Ala Leu Gly Gly Leu Gly Gly Ala Ala Thr Gly Gly Ala Ala Ala
    50                  55                  60

Glu Thr Ala Asp Thr Ser Leu Asp Ile Asp Glu Arg Ile Glu Glu His
65                  70                  75                  80

Arg Thr Gly Asn Leu Glu Val Val Glu Asn Pro Asp Gly Ser Thr
                85                  90                  95

Val Ser Asp Ala Ser Val Ala Val Ser Gln Gln Glu His Asp Phe Gly
            100                 105                 110

Phe Gly Thr Ala Val Asn Ala Asn Thr Leu Ile Asn Ser Ser Ser Glu
        115                 120                 125

Gly Asp Asn Tyr Arg Glu Tyr Ile Pro Glu Leu Phe Asn Lys Ala Val
    130                 135                 140

Met Glu Asn Arg His Lys Trp Asp Phe Trp Glu Asn Glu Gln Gln Leu
145                 150                 155                 160

Ala Asp Glu Ala Thr Glu Trp Ile Leu Asn Gln Gly Leu Asp Met Arg
                165                 170                 175

Gly His Val Cys Ile Trp Gly Arg Glu Asp Val Ala Ala Ile Pro Asp
            180                 185                 190

Asp Ile Leu Thr Ala Ile Asp Glu Gly Asp Glu Gln Thr Ile Arg Glu
        195                 200                 205

Arg Ser Met Ala His Ile Glu Glu Ile Ile Thr His Tyr Gly Asp Asp
    210                 215                 220

Phe Thr Glu Trp Glu Val Val Asn Glu Ala Met His Ala Tyr Gln Leu
225                 230                 235                 240

Gln Ile Gly Val Tyr Gly Asp Gln Ile Asp Thr Glu Glu Pro Trp Thr
                245                 250                 255

Gly Asp Val Val Pro Trp Thr Ser Glu Leu Leu Ala Asp Trp Tyr Asp
            260                 265                 270

Gln Ala Glu Ser Val Ile Glu Glu Asn Gly Leu Asp Val Gly Ile Ala
        275                 280                 285

Val Asn Asp Phe Asn Gln Phe Ala Tyr Gly Tyr Thr Asp Asn Arg Tyr
    290                 295                 300

Val Asn Glu Ile Gln His Ile Asn Asp Asn Ala Val Gln Leu Asp Thr
305                 310                 315                 320

Val Gly Leu Gln Ala His Ala Gly Ala Arg Thr Gly Glu Phe Asn Ser
                325                 330                 335

Asn Asp Ser Pro Asp Gly Arg Ile Ser Ala Ala Gln Val Thr Glu Glu
            340                 345                 350

-continued

```
Met Asn Lys Trp Ala Asp Leu Gly Ala Arg Leu Lys Ile Thr Glu Phe
            355                 360                 365
Asp Thr Tyr Asn Gly Asp Asp Trp Asn Ser Asp Glu Glu Arg Ala Glu
        370                 375                 380
Val Leu Glu Asn Tyr Leu Arg Gly Ala Phe Ser His Pro Gly Cys Asp
385                 390                 395                 400
Asp Phe Ile Met Trp Gly Phe Trp Asp Gly Arg His Trp Glu Asn Glu
                405                 410                 415
Ala Pro Leu Phe Tyr Asp Asp Trp Ser Thr Lys Pro Ala Tyr Asp Val
            420                 425                 430
Trp Thr Gly Leu Val Tyr Asp Glu Trp Trp Thr Asp Asp Ser Gly Thr
        435                 440                 445
Thr Asp Ala Ser Gly Thr Tyr Ala Thr Thr Ala Phe Leu Gly Asp His
    450                 455                 460
Glu Val Thr Val Ser Thr Asp Ser Ala Glu Thr Thr Glu Thr Val Ser
465                 470                 475                 480
Val Ser Asp Ala Ser Gly Thr Thr Thr Val Thr Val Thr Leu Glu Gly
                485                 490                 495
Asp Gly Glu Ser Asp Gly Asp Thr Gln Pro Glu Thr Pro Thr Asn
            500                 505                 510
Leu Thr Ala Thr Asp Ser Thr Ser Ser Ser Ile Thr Val Ser Trp Asp
        515                 520                 525
Gly Val Thr Asp Asn Gly Thr Ser Gly Leu Asp Val Tyr Val Val Ser
    530                 535                 540
Val Asp Gly Ser Glu Asp Gln Thr Val Gly Ala Gly Met Thr Thr Ala
545                 550                 555                 560
Thr Ile Asp Gly Leu Asp Ala Ala Thr Thr Tyr Glu Ile Gly Val Ser
                565                 570                 575
Ala Val Asp Gly Ala Gly Asn Glu Ser Glu Thr Ala Thr Val Gln Ala
            580                 585                 590
Thr Thr Asp Glu Asp Gly Asp Gly Asp Gly Asp Ser Asp Gly
        595                 600                 605
Asp Gly Asp Gly Asp Gly Asn Gly Asp Gly Asp Gly Glu Glu Asp Gly
    610                 615                 620
Asp Glu Thr Gly Asp Gly Asp Leu Ile Ala Glu Met Asp Pro Ser Thr
625                 630                 635                 640
Thr Ser Pro Ala Val Gly Glu Arg Val Thr Phe Arg Val Thr Asp Thr
                645                 650                 655
Thr Asp Ser Gly Asn Trp Ile Ser Ser Leu Glu Trp Asp Leu Gly Asn
            660                 665                 670
Gly Asp Thr Ala Ser Gly Trp Tyr Thr Glu Thr Thr Tyr Glu Ser Ala
        675                 680                 685
Gly Thr Tyr Thr Val Ala Leu Thr Ala Thr Asn Asn Asp Asp Glu Ser
    690                 695                 700
Thr Thr His Glu Val Asp Ile Val Val Gly Gly Asp Gly Asp Gly
705                 710                 715                 720
Asp Gly Glu Gly Asp Gly Asp Gly Asp Gly Asn Gly Asp Gly
                725                 730                 735
Asp Gly Asp Gly Asp Gly Asp Gly Thr Thr Gly Asp Leu Val Ala Glu
            740                 745                 750
Ile Asp Pro Ser Thr Thr Glu Ala Ser Val Gly Gln Thr Val Gln Phe
        755                 760                 765
Trp Leu Thr Asp Ala Thr Gly Ser Ala Asn Trp Ile Thr Gly Ala Glu
```

```
                   770                 775                 780
Trp Asp Leu Gly Asn Gly Asp Thr Gly Ser Gly Trp Tyr Ala Glu Thr
785                 790                 795                 800

Thr Tyr Asp Ala Ala Gly Thr Tyr Thr Val Ser Leu Thr Ala Thr Asp
                805                 810                 815

Asn Asp Asp Glu Ser Thr Thr Asp Glu Val Thr Ile Thr Val Ser
                820                 825                 830

<210> SEQ ID NO 7
<211> LENGTH: 600
<212> TYPE: PRT
<213> ORGANISM: Halorhabdus utahensis

<400> SEQUENCE: 7

Met Thr Asp Asn Asn Thr Gln Ser Thr Thr Gln Ala Asp Arg Gln Gln
1               5                   10                  15

Thr Thr Thr Asp Arg Glu Ser Gly Arg Ser Gly Asp Ala Ser Ser Ser
                20                  25                  30

Asp Gly Leu Glu Ser Pro Ala Arg Arg Asp Val Leu Lys Ala Ile Gly
            35                  40                  45

Ser Gly Ala Leu Ile Gly Val Leu Gly Thr Gly Ser Ala Ser Ala Asp
        50                  55                  60

Pro Ala Thr Phe Gly Asp Gly Val Asn Leu Gln Pro Ser Tyr Phe Cys
65                  70                  75                  80

Asp Gly Asp Gln Ala Leu Gly Trp Asp Leu Met Asn Asp His Pro Asp
                85                  90                  95

Ile Glu Thr Val Arg Ile Glu Ile Glu Pro Phe Ser Phe Asp Glu Val
                100                 105                 110

Ala Thr Thr Val Glu Asp Ala Lys Arg Trp Ile Asp Glu Ala Ala Ala
            115                 120                 125

Asn Gly Lys Asn Val Ile Ala Thr Tyr His His Tyr Pro Asp Asn Gly
130                 135                 140

Ser Ala Glu Ala Ser Ala Leu Gln Asp Ala Ala Asp Phe Trp Val Glu
145                 150                 155                 160

His Tyr Glu Thr Leu Ala Ala Asp Thr Asp Phe Thr Val Asn Leu Met
                165                 170                 175

Asn Glu Trp Gly Asn His Asp Val Thr Ala Glu Glu Tyr Ala Ser Ala
                180                 185                 190

Tyr Asn Asp Ala Ile Ser Thr Val Arg Ser Gly Thr Ser Tyr Asp Gly
            195                 200                 205

Pro Ile Val Cys Asp Ala Pro Gly Trp Gly Gln Gly Thr Tyr Arg Leu
        210                 215                 220

Ala Asp Ala Val Glu Ser Ile Asp His Asp Asp Leu Ile Leu Ser Ala
225                 230                 235                 240

His Val Tyr Pro Ser Ala Trp Asn Ala Thr Thr Gly Gln Asn Leu Val
                245                 250                 255

Pro Glu Asp Leu Asp Val Leu Asp Glu Thr Gly Tyr Pro Cys Met Ile
                260                 265                 270

Gly Glu Phe Gly Asn Tyr Ala Asp Ser Thr Gly Ala Asp Trp Ser Ala
            275                 280                 285

Ile Ile Asp Tyr Ala Lys Glu Leu Gly Trp Pro Val Ile Gly Trp Ala
        290                 295                 300

Trp Asn Gly Asp Gly Ser Asp Asp Pro Met Asn Met Ala Asn Pro Tyr
305                 310                 315                 320
```

```
Trp Gly Asp Asp Cys Gly Ala Glu Ser Tyr Thr Ala Ser Glu Tyr Phe
                325                 330                 335

Asp Val Val Tyr Asp Lys Leu Gly Asp Ser Ala Gly Gly Gly Gly Gly
            340                 345                 350

Ser Asp Asp Gly Asp Asp Gly Thr Asp Gly Gly Asp Gly Thr Asp
        355                 360                 365

Asp Gly Gly Asp Thr Gly Glu Gly Ser Asp Gly Gln Asp Asp Gly Asp
        370                 375                 380

Gly Gly Thr Thr Val Asp Leu Leu Ala Glu Ile Arg Pro Ser Thr Thr
385                 390                 395                 400

Asp Ala Gly Val Gly Glu Arg Leu Thr Phe Ser Val Thr Asp Thr Ser
                405                 410                 415

Gly Thr Asp Arg Trp Ile Asp Ala Leu Ser Trp Asp Phe Asp Asp Gly
            420                 425                 430

Asp Thr Ala Ser Gly Trp Trp Ala Glu His Thr Tyr Asp Ser Ala Gly
        435                 440                 445

Thr Tyr Thr Val Ser Leu Thr Ala Thr Asp Asn Glu Gly Asp Ser Thr
    450                 455                 460

Thr His Gln Val Asp Ile Val Val Gly Gly Asp Asp Gly Ala Asp Asp
465                 470                 475                 480

Gly Gly Gly Gly Glu Ser Asp Gly Asp Asp Ser Glu Ser Ser Asp Glu
                485                 490                 495

Ser Gly Ser Gly Gly Ser Ser Asp Asp Gln Ala Gly Glu Asp Gly Gly
            500                 505                 510

Asp Ser Thr Gly Asp Val Leu Ala Glu Ile Thr Pro Ser Thr Thr Asp
        515                 520                 525

Ala Ala Val Gly Glu Arg Leu Thr Phe Ser Val Thr Asp Thr Ser Gly
    530                 535                 540

Asn Ser Arg Trp Ile Glu Ser Leu Ser Trp Asp Phe Asp Asp Gly Asp
545                 550                 555                 560

Thr Ala Thr Gly Trp Trp Thr Glu His Thr Tyr Asp Ala Thr Gly Thr
                565                 570                 575

Tyr Thr Val Ala Leu Thr Ala Thr Asp Asn Glu Gly Glu Ser Thr Thr
            580                 585                 590

His Glu Val Thr Ile Thr Val Ser
        595                 600

<210> SEQ ID NO 8
<211> LENGTH: 651
<212> TYPE: PRT
<213> ORGANISM: Halorhabdus utahensis

<400> SEQUENCE: 8

Met Thr Lys Asp Arg Ser Thr Glu Arg Thr Glu Thr Asp Glu Ser Thr
1               5                   10                  15

Thr Glu Arg Asp Glu Phe Thr Gln Glu Gly Pro Glu Thr Tyr Arg Ala
            20                  25                  30

Gly Ile Ser Arg Arg Ser Phe Leu Gln Thr Thr Ala Ala Ala Gly Leu
        35                  40                  45

Val Gly Leu Gly Val Gly Ser Gly Ala Val Gly Ser Ala Ala Ala Ala
    50                  55                  60

Gly Ile Pro Thr Pro Trp Leu Glu Val Asp Gly Asn Leu Leu Arg Asp
65                  70                  75                  80

Pro Asp Gly Asn Lys Val Ile Leu Arg Gly Val Asn Val Ile Asp Pro
                85                  90                  95
```

```
Ala Arg Ala Ala Lys Glu Trp Arg Lys Asn Ile Glu Pro Leu Ile Glu
            100                 105                 110

Leu Ala Thr Asp Pro Gly Glu Gly Trp His Ala His Val Ile Arg Leu
            115                 120                 125

Pro Met Gln Pro Gln Asp Ile Gly Asp His Gly Pro Gly Thr Ala Ala
            130                 135                 140

Pro Thr Pro Gly Phe Thr Gln Asp Glu Leu Gln Asn Tyr Leu Ala Glu
145                 150                 155                 160

Tyr Val Asp Pro Ala Val Asp Ala Ala Glu Asp Val Gly Ala Tyr Ile
                165                 170                 175

Met Leu Asp Tyr His Arg His Tyr Pro Glu Gly Pro Asp Trp Asp Ser
            180                 185                 190

Pro Glu Leu Asp Glu Glu Ile Arg Leu Phe Trp Asn Glu Val Ala Pro
            195                 200                 205

Arg Tyr Ser Asp Arg Ser His Val Ile Tyr Glu Leu Tyr Asn Glu Pro
            210                 215                 220

Asn Thr Pro Tyr Pro Gly Ala Gly Asp Pro Thr Asp Asp Val Gly Val
225                 230                 235                 240

Thr Asp Ala Arg Ala Glu Glu Asn Tyr Leu Tyr Trp Arg Glu Thr Ala
                245                 250                 255

Gln Pro Trp Val Asp Leu Ile Arg Glu His Ala Ser Arg Asn Leu Ile
            260                 265                 270

Val Ile Gly Ser Pro Arg Trp Ser Gln Phe Thr Tyr Trp Ala Gly Glu
            275                 280                 285

His Glu Phe Glu Gly Asp Asn Leu Ala Tyr Ala Gly His Val Tyr Ala
            290                 295                 300

His Glu Asn Leu Arg Pro Leu Ser Thr Tyr Phe Gly Glu Pro Ser Glu
305                 310                 315                 320

Glu Val Pro Val Phe Met Ser Glu Phe Gly Tyr Gly Thr Glu Gly Ser
                325                 330                 335

Pro Tyr Leu Val Gly Thr Asn Glu Val Glu Gly Gln Gln Phe Leu Asp
            340                 345                 350

Leu Phe Asp Ala His Asp Ile His Trp Gln Ala Trp Cys Phe Asp His
            355                 360                 365

Thr Trp Ser Pro Gly Met Leu Asn Arg Asp Tyr Glu Val Asp Ser Pro
            370                 375                 380

His Gly Arg Leu Phe Lys Glu Arg Leu Arg Glu Lys Arg Asn Asp Asp
385                 390                 395                 400

Leu Pro Ala Ser Ala Gly Gly Asp Glu Thr Pro Pro Ser Ala Pro
                405                 410                 415

Ser Asn Leu Ala Val Thr Glu Thr Gly Ser Glu Ser Val Gly Leu Ala
            420                 425                 430

Trp Asp Ala Ala Ser Asp Ser Gly Asp Ser Gly Leu Ala Thr Tyr Ala
            435                 440                 445

Val Tyr Leu Asp Gly Ala Leu Asp His Arg Val Thr Ala Gly Thr Thr
            450                 455                 460

Ala Thr Glu Val Ser Gly Leu Leu Pro Glu Thr Thr Tyr Glu Phe Ala
465                 470                 475                 480

Val Ser Ala Val Asp Gly Ala Gly Asn Glu Ser Asp Arg Ser Gly Val
                485                 490                 495

Val Thr Ala Thr Thr Asp Pro Pro Ala Ser Glu Arg Leu Val Leu Asn
            500                 505                 510
```

```
Asp Phe Asp Gly Asp Pro Ala Trp Ala Asp Ser Arg Asn Glu Leu Gly
            515                 520                 525

Asn Trp Cys Gly Ala Gly Ser Phe Ala Asn Asp Asp Gly Glu Val Val
530                 535                 540

Asp Gly Ala Leu Val Leu Glu Tyr Asp Gly Gly Trp Leu Gln Ser Tyr
545                 550                 555                 560

Val Arg Gln Asp Val Ser Ser Phe Ser Thr Leu Asn Leu Gln Val Arg
            565                 570                 575

Gly Ala Asp Gly Gly Glu Glu Ser Ala Phe Ala Val Glu Leu Gly Gly
                580                 585                 590

Gly Gly Gly Val Leu Ala Glu Ile Thr Asp Asp Thr Ile Gly Thr Ser
            595                 600                 605

Phe Ser Thr Val Ser Ile Asp Met Ala Ala Gly Met Asp Gly Ala
        610                 615                 620

Ser Pro Gly Ala Val Tyr Leu Asp Phe Trp Ser Gly Asp Gly Thr Ser
625                 630                 635                 640

Gly Thr Ile Glu Ile Asp Glu Ile Trp Phe Glu
            645                 650
```

<210> SEQ ID NO 9
<211> LENGTH: 1221
<212> TYPE: PRT
<213> ORGANISM: Halorhabdus utahensis

<400> SEQUENCE: 9

```
Met Thr His Asn Asn Pro Asp Asp Ser Thr Ala Arg Arg Thr Thr
1               5                   10                  15

Glu Ser Thr Glu Ser Pro Ser Thr Ala Gly Ile Ala Ser Ala Ser Arg
                20                  25                  30

Arg Asp Phe Leu Lys Ala Ala Ala Gly Gly Ala Ile Ala Thr Gly
                35                  40                  45

Phe Gly Gly Gly Leu Val Gly Ser Ala Ala Ala Asp Val Ile Pro Thr
    50                  55                  60

Pro Pro Leu His Val Asp Gly Asn Leu Ile Lys Asp Pro Asp Gly Ala
65                  70                  75                  80

Thr Val Asn Leu Arg Gly Val Asn Met Ala Asp Pro Lys Arg Ile Asn
                85                  90                  95

Val Thr Ala Pro Ala Arg Gly Lys Thr Ala Thr Asp Val Val Asp Leu
            100                 105                 110

Leu Thr Asn Thr Asp Asp Asp Trp His Ser Arg Val Ile Arg Ile Pro
        115                 120                 125

Val Gln Pro Val Asp Ile Gly Glu His Glu Pro Gly Glu Gly Pro Pro
    130                 135                 140

Pro Val Ala Phe Asp Glu Gly Gln Leu Glu Thr Tyr Leu Glu Glu His
145                 150                 155                 160

Leu Asp Pro Val Ile Glu Arg Cys Leu Gln Arg Gly Ala Tyr Ala Ile
                165                 170                 175

Ile Asp Tyr His Arg His Arg Asp Val Gln Trp Asn Asp Asp Thr Leu
            180                 185                 190

Gly Glu Glu Val Glu Met Phe Trp Asp Thr Val Ala Pro Arg Tyr Ala
        195                 200                 205

Asp Gln Pro His Val Met Tyr Glu Leu Tyr Asn Glu Pro Thr Glu Pro
    210                 215                 220

Gly Met Trp Gly Asp Pro Thr Gln Ser Gln Asn Trp Ala Asp Val Trp
225                 230                 235                 240
```

```
Arg Asp Trp Lys Ala Thr Ala Gln Pro Trp Val Asp Thr Ile Arg Glu
                245                 250                 255

His Ala Pro Asp Asn Leu Ile Leu Ile Gly Ser Pro Ser Trp Ser Gln
            260                 265                 270

Ser Pro Glu Gly Ala Leu Val Glu Pro Phe Asp Gly Glu Asn Leu Ala
        275                 280                 285

Tyr Thr Phe His Ile Tyr Pro Gly His Asn Ser Ser Gln Gln Asn Asp
    290                 295                 300

Trp Glu Asp Ala Thr Asn Asn Gly Glu Gly Val Ala Gly Val Tyr Glu
305                 310                 315                 320

Glu Tyr Pro Leu Phe Val Thr Glu Trp Gly Trp Glu Asn Gly Gly
                325                 330                 335

Gln Tyr Ile Gly Gly Thr Thr Ser Gly Tyr Gly Glu Pro Phe Leu Glu
            340                 345                 350

Phe Leu Glu Lys Ser Asp Ala Ile His Trp Thr Ala Trp Cys Ala Asp
        355                 360                 365

Pro Val Trp Arg Pro Val Met Phe Asp Arg Ala Phe Thr Glu Glu Ser
    370                 375                 380

Phe Glu Asp Asn Ile Gly Asn Pro Tyr Ala Glu Asp Val Pro Glu Asp
385                 390                 395                 400

Cys Ala Asp Leu Pro Cys Asp Trp Thr Leu Leu Gly Gly Asp Ser Tyr
                405                 410                 415

Met Gly Glu Thr Val Lys Asn Ala Leu Ile Asp Tyr Gln Asp Ala Asn
            420                 425                 430

Pro Pro Thr Val Pro Tyr Asp Glu Gln Pro Pro Thr Thr Pro Ser Asn
        435                 440                 445

Leu Thr Ala Glu Asn Val Thr Glu Thr Val Glu Leu Ser Trp Asp
    450                 455                 460

Gly Ser Thr Asp Gln Gly Glu Ala Gly Leu Ser His Tyr Asn Val Thr
465                 470                 475                 480

Val Asp Gly Gln Lys Ile Thr Gln Val Pro Glu Ala Thr Thr Ala Thr
                485                 490                 495

Thr Val Glu Gly Leu Glu Ser Asp Thr Thr Val Thr Ile Gly Val Ser
            500                 505                 510

Ala Val Asp Arg Ala Arg Asn Glu Ser Glu Thr Val Thr Val Glu Val
        515                 520                 525

Thr Thr Asp Ala Phe Glu Asp Ser Thr Pro Pro Ser Val Pro Ala Asn
    530                 535                 540

Leu Thr Ser Pro Glu Asn Thr Trp Gln Ser Val Ala Ile Ser Trp Asp
545                 550                 555                 560

Asp Ser Thr Asp Glu Gly Asp Ala Glu Thr Ala Gly Leu Asp Gly Tyr
                565                 570                 575

Val Val Tyr Val Asp Gly Glu Leu Glu Arg Glu Val Ala Ala Glu Thr
            580                 585                 590

Thr Gln Val Gln Ile Gly Gly Leu Asp Ser Asp Thr Thr Tyr Glu Phe
        595                 600                 605

Gly Val Ser Ala Val Asp Arg Ala Asp Asn Glu Ser Asp Ile Ala Thr
    610                 615                 620

Ile Asp Val Thr Thr Asp Leu Ala Arg Ala Gly Pro Asn Asp Leu Leu
625                 630                 635                 640

Ile Asn Asp Tyr Asp Gly Asp Pro Ala Trp Pro Asp Ser Asn Asp Leu
                645                 650                 655
```

Gly Asn Trp Val Gly Thr Gly Gly Phe Glu Ser Ala Glu Val Val Asp
            660                 665                 670

Gly Arg Leu Glu Ile Asp Tyr Asn Ala Ser Gly Trp Tyr Gly Thr Gly
        675                 680                 685

Val Ser Gln Asp Ile Thr Asp Tyr Pro Thr Leu Arg Met Lys Val Thr
    690                 695                 700

Gly Glu Asn Gly Gly Glu His Arg Gly Ile Glu Leu Gln Phe Ala Gly
705                 710                 715                 720

Ile Asp Pro Leu Leu Ser Glu Val Thr Asp Asp Thr Ile Gly Thr Thr
                725                 730                 735

Glu Ser Ile Val Ser Val Asp Leu Glu Ala Ala Gly Ala Asp Leu Glu
            740                 745                 750

Ser Pro Gly Gln Leu Thr Leu Arg Phe Tyr Asp Ala Gly Asp Ser Ser
        755                 760                 765

Ile Ser Ile Asp Glu Leu Trp Leu Asp Ser Asp Glu Pro Asp Asp Asp
    770                 775                 780

Gly Asp Ser Ile Ala Pro Thr Ala Pro Ala Ser Val Glu Ser Pro Thr
785                 790                 795                 800

Gln Ser Glu Thr Ala Val Glu Ile Glu Trp Ser Ala Ser Ser Asp Asp
                805                 810                 815

Gly Gly Ser Gly Leu Asp His Tyr Asn Val Ser Val Asp Gly Ser Ile
            820                 825                 830

Asp Gln Gln Val Pro Ala Gly Thr Ala Ala Thr Ile Glu Gly Leu
        835                 840                 845

Asp Ala Gly Ser Ser Tyr Glu Ile Gly Val Ser Ala Val Asp Gly Ala
    850                 855                 860

Gly Asn Glu Ser Ser Gln Thr Thr Val Thr Val Ser Thr Ala Gly Gly
865                 870                 875                 880

Asp Asp Glu Gln Ala Pro Ser Ala Pro Ala Asn Leu Thr Ser Thr Asp
                885                 890                 895

Arg Thr Asp Thr Ser Ile Asp Leu Ala Trp Asp Ala Ser Thr Asp Glu
            900                 905                 910

Gly Gly Ser Gly Leu Asp His Tyr Thr Val Ala Val Ala Gly Glu Gln
        915                 920                 925

Val Gln Gln Val Asp Ala Gly Thr Thr Thr Ala Thr Val Ser Glu Leu
    930                 935                 940

Ser Pro Gly Thr Ser Tyr Asp Ile Ala Val Thr Ala Val Asp Ala Ala
945                 950                 955                 960

Gly Asn Glu Ser Thr Pro Ala Thr Leu Thr Val Ala Thr Thr Asp Gly
                965                 970                 975

Asp Asp Gln Gln Ala Pro Thr Met Pro Gly Asn Leu Ser Val Thr Gly
            980                 985                 990

Ser Thr Ala Ala Ser Ile Ala Val Ser Trp Asp Ala Ser Thr Asp Ser
        995                 1000                1005

Gly Gly Ser Gly Leu Asp His Tyr Thr Val Phe Leu Asp Gly Ser
    1010                1015                1020

Gln Asp Gln Gln Ile Glu Gly Thr Thr Glu Ala Thr Val Val
    1025                1030                1035

Gly Leu Ser Ala Asp Thr Thr Tyr Glu Ile Gly Val Ser Ala Val
    1040                1045                1050

Asp Gly Ala Gly Asn Glu Ser Glu Thr Val Thr Ile Glu Thr Thr
    1055                1060                1065

Thr Pro Pro Gly Asp Pro Val Ala Gly Leu Val Val Asn Asp Tyr

```
                1070                1075                1080
Asp Gly Asp Pro Ala Trp Ser Asn His Arg Asn Asp Leu Gly Asn
            1085                1090                1095

Trp Cys Gly Ala Gly Ser Phe Ala Asn Gly Gly Gly Asp Val Glu
    1100                1105                1110

Asp Gly Ala Leu Val Leu Glu Tyr Asp Asn Ala Gly Trp Phe Val
    1115                1120                1125

Glu Gln Ile Gln Gln Asp Val Ser Glu Tyr Ser Ser Ile Val Phe
    1130                1135                1140

Ser Ile Ala Gly Ala Ser Gly Gly Glu Gly Asp His Phe Val Val
    1145                1150                1155

Gly Val Gly Gly Asn Arg Ser Thr Phe Ser Asp Val Ala Asp Gly
    1160                1165                1170

Ser Ile Gly Thr Ser Val Ala Asp Val Ala Ile Asp Met Glu Ser
    1175                1180                1185

Ala Gly Ile Asp Ala Gly Ser Leu Gly Glu Leu Arg Leu Asn Phe
    1190                1195                1200

Trp Gln Ala Gly Ser Gly Ser Gly Thr Leu Arg Ile Glu Glu Ile
    1205                1210                1215

Arg Leu Glu
    1220

<210> SEQ ID NO 10
<211> LENGTH: 1050
<212> TYPE: PRT
<213> ORGANISM: Halorhabdus utahensis

<400> SEQUENCE: 10

Met Ala Arg Asp Asn His Thr Tyr Ala Gly Gly Gly Ala Asp Arg Pro
1               5                   10                  15

Asp Gly Arg Thr Tyr Arg Pro Asp Asp Arg Arg Ser Ala Leu Ala Ala
            20                  25                  30

Ser Arg Arg Asp Val Leu Arg Thr Ile Gly Ala Gly Ala Leu Leu Gly
        35                  40                  45

Ser Ile Gly Thr Ala Arg Val Gln Ala Ala Pro Gly Asp Arg Glu Phe
    50                  55                  60

Val Ala Thr Asp Gly Pro Glu Phe Thr Val Gly Gly Glu Pro Ile Tyr
65                  70                  75                  80

Phe Ser Gly Thr Asn Asn Phe Trp Val Thr Asp Pro Tyr Ser Asp Arg
                85                  90                  95

Ser Arg Ile Asp Asp Val Leu Ala Leu Cys Ala Asp Leu Asp Gln Asn
            100                 105                 110

Leu Leu Arg Thr Trp Ala Phe Cys Ala Gly Glu Gly Gly Gln Cys Leu
        115                 120                 125

Gln Pro Glu Pro Gly Val Phe Asn Glu Ala Ala Leu Gln His Leu Asp
    130                 135                 140

Tyr Leu Val Ala Lys Ala Gly Glu His Gly Val Arg Leu Ile Leu Ser
145                 150                 155                 160

Leu Val Asn Asn Trp Asp Asp Tyr Gly Gly Met Ala Gln Tyr Ile Glu
                165                 170                 175

Trp Ala Asp Gly Ala Ser Glu His Gly Asp Phe Tyr Val Asn Glu Ala
            180                 185                 190

Cys Arg Glu Leu Tyr Arg Thr His Val Glu Thr Leu Leu Thr Arg Glu
        195                 200                 205
```

```
Asn Ser Ile Thr Gly Val Glu Tyr Arg Asn Asp Pro Ala Ile Ala Met
    210                 215                 220
Trp Glu Leu Ala Asn Glu Pro Arg Leu Glu Asp Asp Thr Glu Thr
225                 230                 235                 240
Ile Asp Asp Arg Glu Ala Ala Leu Thr Glu Trp Phe Ala Asp Met Ser
                245                 250                 255
Gly Phe Ile Lys Asp Phe Asp Asn His Leu Val Thr Thr Gly Leu
                260                 265                 270
Glu Gly Phe Tyr Thr Arg Ala Asp Gly Pro Asn Trp Met Tyr Gly Asp
                275                 280                 285
Trp Thr Gly Gln Asn Phe Ile Ala His His Glu Ile Asp Thr Ile Asp
290                 295                 300
Val Cys Ser Phe His Leu Tyr Pro Tyr His Trp Pro Gly Met Gly Leu
305                 310                 315                 320
Ala Gly Gln Leu Ala Glu Asp Val Val Ser Ala Val Glu Trp Ile
                325                 330                 335
Arg Glu His Ala Ala Asp Ala Arg Glu Thr Leu Glu Lys Pro Ala Leu
                340                 345                 350
Leu Gly Glu Phe Asn Val Asn Val Gln Glu His Asp Leu Ala Thr Arg
                355                 360                 365
Asn Asp Arg Leu Arg Ala Trp Tyr Asp Ala Leu Asp Ser Gln Asp Ala
370                 375                 380
Gly Ala Ala Ala Ile Trp Gln Leu Val Leu Glu Asp Thr Glu Asp His
385                 390                 395                 400
Asp Gly Phe Gln Val Tyr Arg Ser Glu Ser Gly Asp Ile Leu Ser Gly
                405                 410                 415
Tyr Ala Ser Thr Ile Arg Glu Lys Ser Gly His Ser Asp Gly Thr Pro
                420                 425                 430
Thr Ala Asp Ala Thr Ala Pro Ser Ser Leu Arg Ile Gly Glu Ser Gly
                435                 440                 445
Asp Phe Ser Gly Thr Tyr Ser Phe Asp Pro Asp Gly Ser Ile Ala Ala
                450                 455                 460
Tyr Asp Trp Ala Phe Asp Asp Gly Ala Thr Ala Thr Gly Glu Arg Val
465                 470                 475                 480
Ala His Arg Phe Ala Glu Thr Gly Ser His Glu Ala Glu Leu Thr Val
                485                 490                 495
Thr Asp Asp Ser Gly Ala Thr Asp Ala Asp Ile Glu Ser Val Ser Val
                500                 505                 510
Glu Gly Ile Pro Glu Asp Ser Phe Leu Val Gly Ala Gly Glu Thr
                515                 520                 525
Phe His Arg Asp Thr Lys Gln Cys His Phe Ala Ser Met Pro Ala Ser
530                 535                 540
Gly Asp Val Ala Val Thr Ala Arg Val Ala Asp Leu Glu Pro Val Asp
545                 550                 555                 560
Pro Glu Thr Gln Ala Gly Val Met Val Ala Asp Pro Asp Ala Pro
                565                 570                 575
Gly Ala Leu Gly Ala Ala Thr Ile Thr Pro Gly Glu Gly Ser Glu Leu
                580                 585                 590
Thr Arg Ala Tyr Asp Ser Thr Val Trp Arg Glu Arg Ala Gly Asp Asp
                595                 600                 605
Arg Thr Pro Pro Ile Trp Leu Arg Val Lys Arg Ser Gly Ser Thr Val
610                 615                 620
Ser Ala Ser Val Ser Pro Asn Gly Ser Asp Trp Thr Glu Ile Gly Ser
```

```
            625                 630                 635                 640
Gly Asp Val Asp Leu Pro Asp Val His Val Gly Leu Phe Val Ser
                645                 650                 655

Ser Asn Ala Ala Gly Glu Leu Ala Ala Ala Arg Phe Asp Glu Val Asp
                660                 665                 670

Trp Leu Glu Asp Trp Thr Ala Thr Asp Val Gly Pro Val Ser Val Ala
            675                 680                 685

Gly Ala Thr Thr Ala Gly Asp Gly Thr Thr Asp Gly Asp Gly Asp
690                 695                 700

Glu Asp Thr Thr Pro Pro Thr Ala Pro Gly Asp Leu Thr Val Thr Glu
705                 710                 715                 720

Thr Thr Asp Ser Ser Ile Ser Leu Ser Trp Asp Ala Ala Thr Asp Asp
                725                 730                 735

Gly Gly Ser Gly Leu Ala His Tyr Asp Val Ser Val Asp Gly Ala Leu
                740                 745                 750

Asp Gln Gln Val Pro Ala Gly Thr Thr Thr Ala Thr Val Glu Ala Leu
            755                 760                 765

Asp Pro Gly Thr Ala Tyr Asp Ile Gly Val Ser Ala Val Asp Gly Ala
770                 775                 780

Gly Asn Glu Ser Gly Thr Val Thr Val Thr Ala Thr Thr Gly Asp Gly
785                 790                 795                 800

Asp Asp Glu Ala Pro Thr Ala Pro Ala Asp Leu Thr Ala Thr Glu Thr
                805                 810                 815

Thr Ser Ser Ser Val Ser Leu Ser Trp Asp Ala Ser Thr Asp Ser Gly
                820                 825                 830

Gly Ser Gly Val Glu Gln Tyr Val Val Ala Val Asp Gly Glu Thr Ala
            835                 840                 845

His Thr Val Glu Ala Asp Thr Thr Ser Thr Thr Val Glu Glu Leu Asp
            850                 855                 860

Ala Glu Thr Thr Tyr Glu Leu Gly Val Ser Ala Val Asp Ala Ala Gly
865                 870                 875                 880

Asn Val Ser Asp Pro Ala Val Ile Glu Val Ala Thr Ala Glu Gly Asp
                885                 890                 895

Asp Ser Asp Glu Glu Pro Pro Glu Asn Ala Leu Val Val Asn Asp Tyr
                900                 905                 910

Asp Gly Asp Pro Ala Trp Ser Ser Asn Arg Asn Asp Leu Gly Asn Trp
            915                 920                 925

Cys Gly Ala Gly Ser Phe Ala Asn Gly Gly Asp Val Glu Asp Gly
            930                 935                 940

Ala Leu Val Leu Glu Tyr Asp Asn Ala Gly Trp Phe Val Glu Gln Leu
945                 950                 955                 960

Asn Gln Asp Val Ser Ala His Ser Glu Leu Val Phe Val Ser Gly
                965                 970                 975

Ala Ser Gly Gly Glu Gly Asp His Phe Val Ser Ala Gly Gly Val
            980                 985                 990

Arg Ser Arg Phe Ser Asp Val Ala Asp Gly Ser Ile Asp Thr Asp Pro
            995                 1000                1005

Lys Pro Ile Ala Ile Asp Met Glu Ser Ala Gly Ile Asp Ala Thr
        1010                1015                1020

Ser Pro Gly Glu Leu Arg Leu Asn Phe Trp Gln Gly Gly Ser Gly
        1025                1030                1035

Ser Gly Ala Leu Arg Ile Glu Glu Ile Arg Leu Glu
        1040                1045                1050
```

<210> SEQ ID NO 11
<211> LENGTH: 670
<212> TYPE: PRT
<213> ORGANISM: Halorhabdus utahensis

<400> SEQUENCE: 11

```
Met Thr Arg Glu Thr Asp Gly Asn Asp Arg Glu Arg Ala Ser Asn Leu
 1               5                  10                  15

Thr Arg Arg Val Leu Gln Ala Gly Ala Ser Gly Leu Leu Ala Ala
            20                  25                  30

Thr Val Gly Thr Ser Ala Leu Thr Ala Thr Gly Ala Val Thr Thr
            35                  40                  45

Ala Arg Ile Ser Pro Ser Asp Gly Phe Ala Ala Val Gly Asp Trp Leu
 50                  55                  60

Glu Asp Asp Glu Pro Glu Ile Tyr Arg Ile Gln Glu Pro Thr Arg Ser
 65                  70                  75                  80

Ala Val Glu Ala Ala Phe Gln Ala Ser Gly Pro Arg Val Val Phe
                85                  90                  95

Glu Thr Ser Gly Thr Ile Asp Leu Gly Gly Glu Ala Leu Ala Ile Thr
                100                 105                 110

Glu Asp Lys Cys Trp Val Ala Gly Gln Thr Ala Pro Ser Ser Gly Ile
                115                 120                 125

Thr Phe Val Lys Gly Met Val Gln Val Asp Ala Asp Asp Cys Val Val
 130                 135                 140

Gln His Ile Arg Thr Arg His Gly Pro Gly Ser Asp Gly Glu Ile Gln
145                 150                 155                 160

Ser Asn Asp Ser Leu Asn Thr Ala Asp Asp Thr Ser Asn Asn Val Ile
                165                 170                 175

Asp His Val Thr Ala Ser Trp Gly Thr Asp Glu Cys Leu Ser Val Gly
                180                 185                 190

Tyr Asp Thr Thr Asp Thr Thr Val Thr Asn Cys Leu Val Tyr Glu Gly
                195                 200                 205

Leu Tyr Asp Pro Tyr Gly Asp Ser Ser Asp His Asn Tyr Ala Thr Leu
    210                 215                 220

Val Gly Asp Gly Ala Glu Asn Val Thr Leu Ala Gly Asn Val Trp Ala
225                 230                 235                 240

Lys Cys Arg Gly Arg Val Pro Arg Leu Lys Ser Glu Thr Arg Ser Val
                245                 250                 255

Val Ala Asn Asn Val Met Tyr Phe Phe Asn Glu Ala Thr Asn Met Asp
                260                 265                 270

Gly Asp Thr Ala Ala Ile Val Gly Asn Val Tyr Ile Pro Gln Asp
                275                 280                 285

Val Asp Asp Thr Pro Ile Glu Asp Gly Asn Ala Ser Leu Ser Asp Asn
    290                 295                 300

Val Thr Asp Pro Ser Ser Thr Pro Leu Thr Gly Gly Thr Glu Glu Leu
305                 310                 315                 320

Ser Ser Arg Pro Leu Trp Pro Ala Gly Phe Glu Thr Leu Asp Val Ser
                325                 330                 335

Gly Val Glu Ser His Asn Leu Ser Asn Ala Gly Ala Arg Pro Ala Asp
                340                 345                 350

Arg Thr Asp Asn Asp Ala Arg Ile Val Ser Glu Ile Arg Asp Arg Ala
                355                 360                 365

Gly Asp Asp Tyr Leu Asp Ser Pro Tyr Asp Tyr Trp Val Pro His Pro
```

```
            370                 375                 380
Asp Ala Val Gly Gly Tyr Pro Asp Leu Pro Val Asn Thr His Ser Leu
385                 390                 395                 400

Ser Val Pro Asp Thr Gly Leu Arg Glu Trp Leu Thr Glu Trp Ala Ala
                405                 410                 415

Ala Val Glu Asp Ala Ser Ala Asp Pro Gly Thr Gly Gly Glu Ser
            420                 425                 430

Asp Glu Gly Asp Gly Asn Ser Gly Ser Asp Asp Gly Ser Gly Asp Asp
                435                 440                 445

Ser Gly Gly Asp Asp Gly Ser Asp Asp Gly Ser Gly Asp Ser Thr Asp
            450                 455                 460

Cys Glu Pro Thr Thr Ile Glu Pro Tyr Leu Arg Val Asp Gly Gly Asp
465                 470                 475                 480

Trp Gln Asn Thr Gly Glu Val Thr Val Glu Pro Gly Gly Ser Val Glu
                485                 490                 495

Phe Gly Pro His Pro His Asp Gly Thr Asp Asp Trp Val Trp Asn Gly
                500                 505                 510

Pro Gly Leu Ser Ala Thr Thr Arg Glu Val Val Glu Pro Asp Ala
            515                 520                 525

Thr Ala Thr Tyr Thr Ala Ala Tyr Thr Asn Asp Cys Gly Ala Val Ser
530                 535                 540

Glu Tyr Glu Phe Val Val Thr Val Glu Glu Arg Asp Asp Gly Ala Asp
545                 550                 555                 560

Ser Asp Ser Gly Gly Asp Gly Ser Gly Thr Asp Gly Ser Gly Asp
            565                 570                 575

Gly Ser Gly Asp Asp Glu Thr Ser Ser Asp Asp Leu Ile Ala Glu Leu
                580                 585                 590

Asp Pro Gly Thr Thr Asp Ala Ala Val Gly Glu Trp Ile Pro Phe Ala
            595                 600                 605

Ile Val Asp Thr Thr Asp Ser Asp His Trp Ile Thr Gly Leu Ser Trp
610                 615                 620

Ser Phe Gly Asp Gly Thr Thr Ala Thr Gly Trp Trp Asn Ala His Thr
625                 630                 635                 640

Tyr Asp Thr Ala Gly Thr Tyr Pro Val Ser Leu Thr Ala Thr Asn Asp
                645                 650                 655

Ala Gly Glu Ser Thr Thr His Glu Val Ser Ile Thr Val Thr
            660                 665                 670

<210> SEQ ID NO 12
<211> LENGTH: 1004
<212> TYPE: PRT
<213> ORGANISM: Halorhabdus utahensis

<400> SEQUENCE: 12

Met Thr Asp Glu Ala Thr Glu Ser Ile Glu Ala Ser Ala Thr Asp His
1               5                   10                  15

Thr Asp Glu Thr Ala Gly Asn Arg Lys Asp Pro Gly Leu Thr Ser Ser
                20                  25                  30

Arg Arg Thr Phe Leu Gly Ala Met Ala Ser Ala Gly Thr Ile Gly Ala
            35                  40                  45

Gly Leu Ser Ala Ala Thr Gly Thr Ala Ala Ala Gly Val Pro Thr Pro
        50                  55                  60

Arg Leu His Thr Glu Gly Arg Trp Ile Arg Asp Pro Ala Gly Asn Asp
65                  70                  75                  80
```

```
Val Thr Leu Arg Gly Met Ala Pro Ala Asp Pro Gly Phe Tyr Arg Gln
             85                  90                  95

Tyr His Pro Lys Ser Phe Glu Glu Val Leu Glu Trp Ala Thr Asp Thr
        100                 105                 110

Asp Arg Gly Trp His Pro Asn Ile Val Arg Leu Pro Cys Thr Gln Asp
        115                 120                 125

Ser Ile Asp Ala Leu Gly Leu Glu Thr Tyr Val Thr Glu Val Leu Arg
130                 135                 140

Pro Ala Val Asp Leu Leu Ala Ala Arg Asp Val Tyr Ala Leu Val Asp
145                 150                 155                 160

Phe His Leu Ile Arg Pro Tyr Thr Gln Asp Ala Thr Glu Thr Tyr Asn
                165                 170                 175

Glu Glu Asn Asp Asp Asp Leu Ala Pro Ile Asp Asp Val Met Thr Thr
                180                 185                 190

Phe Trp Asp Arg Val Ala Pro Glu Phe Ala Glu Asp Glu His Val Ile
            195                 200                 205

Tyr Glu Leu Phe Asn Glu Pro Thr Gln Pro Ala Met Tyr Gly Asp Asp
        210                 215                 220

Ala Gly Ala Phe Gln Ala Trp Arg Asp Ala Ala Gln Pro Trp Val Asp
225                 230                 235                 240

Leu Val Arg Glu His Ala Pro Glu Thr Pro Ile Ile Gly Ser Pro
                245                 250                 255

Arg Trp Thr Ser Val Thr His Met Ala Pro Glu Tyr Pro Phe Asp Gly
            260                 265                 270

Glu Asn Leu Ile Tyr Ala Ala His Ile Tyr Pro Asp Asn Gly Pro Pro
        275                 280                 285

Ala Asp Phe Asp Gln Trp Tyr Gly Glu Pro Ala Thr Glu Val Pro Val
        290                 295                 300

Val Val Thr Glu Phe Gly Trp Glu Pro Thr Gly Gly Ser Val Asp Gln
305                 310                 315                 320

Gly Thr Thr Ser Gly Trp Gly Pro Phe Arg Glu Trp Val Glu Gly
                325                 330                 335

Tyr Glu Asn Met Gly Trp Ile Ser Trp Cys Phe Asp Asp Ser Trp Glu
            340                 345                 350

Pro Ala Phe Phe Glu Ser Pro Asp Ala Gly Ala Asn Glu Pro Trp Thr
        355                 360                 365

Leu Lys Asp Asp Ala Asp Gln Met Gly Gly Tyr Ile Lys Thr Trp Leu
370                 375                 380

Glu Ala Thr Lys Asp Gln Gly Ile Pro Glu Ser Ala Ile Asp Asp
385                 390                 395                 400

Val Ala Pro Pro Val Pro Ser Gly Leu Glu Val Thr Arg Ser Thr Glu
                405                 410                 415

Ile Ser Val Glu Ile Ala Trp Asn Ala Val Thr Asp Glu Gly Glu Ala
            420                 425                 430

Gly Leu Ser His Tyr Asn Val Tyr Val Asp Gly Glu Arg Arg Gly Gln
        435                 440                 445

Val Ile Asp Gly Thr Ala Thr Thr Val Asp Gly Leu Glu Pro Ala Ser
450                 455                 460

Thr Tyr Glu Val Gly Val Ser Ala Val Asp Ser Ala Gly Asn Glu Ser
465                 470                 475                 480

Asn Gln Thr Thr Thr Val Ala Glu Thr Ile Ala Thr Asp Ala Gly Gln
                485                 490                 495

Ser Ala Phe Val Glu His Glu Leu Pro Gly Arg Ile Gln Ala Glu Asp
```

-continued

```
                500                 505                 510
Phe Asp Glu Gly Gly Gln Gly Ile Ala Tyr Tyr Asp Thr Gly Ser Thr
            515                 520                 525

Asn Glu Ala Gly Ala Asp Tyr Arg Glu Thr Gly Val Asp Ile Gly Thr
            530                 535                 540

Ala Val Glu Ser Gly Tyr Asn Val Gly Tyr Thr Glu Thr Gly Glu Trp
545                 550                 555                 560

Leu Glu Tyr Thr Val Thr Val Glu Ser Gly Gly Ser Tyr Glu Ala Thr
                565                 570                 575

Val Arg Val Ala Asn Gly Ala Asp Ser Gly Gly Asp Leu Arg Ile Glu
            580                 585                 590

Val Asp Arg Ala Glu Val Ala Thr Gln Asn Val Trp Pro Thr Gly Gly
            595                 600                 605

Trp Glu Asn Phe Glu Glu Ile Arg Val Gly Glu Val Asp Ile Pro Glu
            610                 615                 620

Gly Glu His Val Ile Arg Ile Val Val Glu Thr Ser Gly Trp Asn Phe
625                 630                 635                 640

Asp Trp Ile Glu Phe Thr Gly Gly Asp Gly Gly Glu Asp Val Thr
                645                 650                 655

Pro Pro Thr Ala Pro Ser Asn Leu Ser Val Thr Thr Thr Pro Ser
                660                 665                 670

Ser Ala Glu Ile Ala Trp Asp Ala Ala Thr Asp Glu Gly Gly Ser Gly
            675                 680                 685

Leu Asp His Tyr Ala Val Tyr Val Asp Gly Ser Leu Asp Gln Gln Val
            690                 695                 700

Pro Thr Gly Thr Thr Ser Ala Thr Ile Ala Asp Leu Ala Ala Glu Thr
705                 710                 715                 720

Ser Tyr Glu Ile Gly Val Ser Ala Val Asp Gly Ala Gly Asn Glu Ser
                725                 730                 735

Glu Ser Val Thr Val Asp Val Thr Thr Asp Ala Gly Asp Thr Thr
                740                 745                 750

Pro Pro Thr Val Pro Gly Asp Leu Ser Val Asp Gly Thr Thr Ala Thr
            755                 760                 765

Ser Ile Asp Val Ala Trp Ser Gly Ala Ser Asp Ala Gly Thr Gly Val
770                 775                 780

Asp Ala Tyr Ala Val Tyr Val Asp Gly Ser Arg Asp Gln Ala Val Lys
785                 790                 795                 800

Ala Gly Thr Thr Thr Ala Thr Ile Asp Ser Leu Ser Ala Val Thr Thr
                805                 810                 815

Tyr Glu Val Gly Val Ser Ala Ile Asp Gly Ala Gly Asn Glu Ser Ala
            820                 825                 830

Thr Ala Thr Val Glu Ala Thr Thr Asp Gln Ser Asp Gly Glu Asp
                835                 840                 845

Asp Glu Asp Asp Glu Ser Pro Ala Asp Ala Leu Val Val Asn Asp Tyr
            850                 855                 860

Asp Gly Asp Pro Ser Trp Ser Ser Asn Arg Asn Asp Leu Gly Lys Trp
865                 870                 875                 880

Cys Gly Ala Gly Ser Phe Gln Asn Gly Thr Ala Gly Gly Ala Val
                885                 890                 895

Glu Asp Gly Ala Leu Val Leu Glu Tyr Asp Asn Ala Gly Trp Phe Val
            900                 905                 910

Glu Gln Val Gln Gln Asp Val Ser Asp Tyr Ser Thr Val Val Leu Arg
            915                 920                 925
```

Val Ser Gly Ala Asn Gly Gly Glu Ser Glu Phe Leu Phe Asp Met
    930                 935                 940

Gly Gly Ala Arg Asp Leu Leu Ala Asn Leu Thr Asp Asp Ser Ile Thr
945                 950                 955                 960

Thr Ser Val Thr Asp Val Ala Ile Asp Met Glu Ser Ala Gly Ile Asp
            965                 970                 975

Pro Ser Gly Gly Gly Leu Ser Ile Arg Leu Asn Phe Trp Gln Gly Gly
            980                 985                 990

Ala Ser Thr Leu Glu Ile Glu Glu Ile Arg Leu Glu
            995                 1000

<210> SEQ ID NO 13
<211> LENGTH: 974
<212> TYPE: PRT
<213> ORGANISM: Halorhabdus utahensis

<400> SEQUENCE: 13

Met Gly Arg Thr Thr Thr Asp Gly Asp Thr Asp Leu Phe Arg Arg Asp
1               5                   10                  15

Leu Leu Ala Ala Met Gly Leu Gly Ala Gly Ser Val Ala Leu Gly Thr
            20                  25                  30

Asp Val Ala Thr Pro Ser Val Val Ser Arg Ala Ala Ala Gln Thr Asp
        35                  40                  45

Leu Gly Phe Asp Tyr Ala His Ala Leu Gln Gln Ser Leu Tyr Phe Tyr
    50                  55                  60

Asp Ala Asn Arg Cys Gly Ala Thr Thr Met Gly Asn Arg Leu Gln Trp
65                  70                  75                  80

Arg Gly Glu Cys His His Ser Asp Thr Glu Ile Pro Leu Asp Ala Ala
                85                  90                  95

Thr Glu Asp Gly Gly Thr Asn Leu Ser Gly Ser Phe Ile Glu Glu Tyr
            100                 105                 110

Ser Asp Val Leu Asp Pro Asp Gly Thr Gly Thr Ile Asp Val Ser Gly
        115                 120                 125

Gly Phe His Asp Ala Gly Asp His Met Lys Phe Gly Leu Pro Gln Ser
    130                 135                 140

Tyr Ser Ala Ser Thr Leu Ser Trp Ala Leu Tyr Glu Phe Glu Asp Ala
145                 150                 155                 160

Phe Arg Asp Val Gly Ser Tyr Asp His Met Val Asp Ile Leu Arg His
                165                 170                 175

Phe Ala Asp Tyr Phe Leu Lys Ser Thr Phe Arg Asp Asp Glu Gly Asn
            180                 185                 190

Val Val Ala Phe Cys Tyr His Val Gly Glu Gly Ser Ile Asp His Asn
        195                 200                 205

Tyr Trp Gly Pro Pro Glu Leu Gln Ser Ser Glu Glu Tyr Pro Arg Pro
    210                 215                 220

Ala Tyr Phe Ala Thr Pro Glu Asp Pro Ala Ser Asp Gln Cys Ala Gly
225                 230                 235                 240

Thr Ala Ala Ala Leu Thr Ile Thr Ser Leu Val Leu Glu Ser Glu Asp
                245                 250                 255

Ser Ala Tyr Ala Ala Glu Cys Leu Asp Thr Ala Gln Ala Leu Tyr Asp
            260                 265                 270

Phe Ala Val Glu Asn Arg Gly Leu Gly Tyr Asp Gly Phe Tyr Asp
        275                 280                 285

Ser Ser Tyr Asp Glu Asp Glu Leu Ser Trp Ala Ala Val Trp Leu His

```
            290                 295                 300
Ile Ala Thr Glu Asp Asp Ala Tyr Leu Asp Asp Ile Leu Ala Thr Asp
305                 310                 315                 320
Asp Ser Gly Thr Tyr Thr Gly Tyr Leu Gly Glu Ile Ile Asp Ser Thr
                    325                 330                 335
Asp Asp Asp Trp Gln Asn Ile Trp Val His Ser Trp Asp Thr Val Trp
                340                 345                 350
Gly Gly Val Phe Leu Lys Leu Ala Pro Ile Thr Asp Asp Pro Glu His
            355                 360                 365
Trp Gln Ile Ala Arg Trp Asn Leu Glu Tyr Leu Ser Gly Gly Ser Val
370                 375                 380
Glu His Glu Asp Asp Asn Asp Thr Asn Tyr Ala Ser Thr Ser Asp Ala
385                 390                 395                 400
Gly Phe Thr Val Leu Asn Thr Trp Gly Ser Ala Arg Tyr Asn Ala Ala
                    405                 410                 415
Ala Gln Phe Gln Ala Met Val Tyr Arg Lys Tyr Arg Asp Thr Glu Lys
                420                 425                 430
Ala Val Ala Leu Thr Asp Trp Ala Ala Thr Gln Met Asn Tyr Ile Met
            435                 440                 445
Gly Asp Asn Ser Phe Gly Tyr Ser Leu Ile Val Gly Phe Thr Asp Asp
450                 455                 460
His Ala Glu His Pro His His Arg Ala Ala His Gly Ser Lys Glu Asn
465                 470                 475                 480
Ser Met Glu Glu Pro Glu His Arg His Thr Leu Trp Gly Ala Leu
                    485                 490                 495
Val Gly Gly Pro Asp Glu Asp Asp Thr His Val Asp Glu Thr Ser Asp
                500                 505                 510
Tyr Val Tyr Asn Glu Val Ala Ile Asp Phe Asn Ala Gly Leu Val Gly
            515                 520                 525
Ala Leu Ala Gly Phe Asn Thr Phe Tyr Asp Asp Thr Gly Glu Ala Val
            530                 535                 540
Ala Glu Phe Pro Pro Gly Glu Glu Pro Ile Asp Ala Tyr Tyr Ala Glu
545                 550                 555                 560
Gly Glu Val Leu Gln Glu Asn Ala Asp Arg Thr Gln Val Arg Val Thr
                    565                 570                 575
Ile His Asn Glu Ser Ile His Pro Pro His Arg Glu Asp Gly Leu Ser
                580                 585                 590
Ala Arg Tyr Phe Ile Asp Val Ser Glu Leu Arg Asp Ala Gly Gln Ser
            595                 600                 605
Ile Asp Ala Val Ser Val Glu Val Gln Tyr Asp Gln Gln Ser Thr Met
610                 615                 620
Gly Asp Gly Ser Ala Asp Val Ser Gly Pro Ile Ala Trp Asp Glu Asp
625                 630                 635                 640
Ala Gly Ile Tyr Tyr Ile Glu Leu Asp Trp Ser Gly Asn Gln Ile Tyr
                    645                 650                 655
Gly Ala Arg Glu Ile Gln Ile Ser Met Ile Ala Glu Gln Asp Asp Asn
                660                 665                 670
Trp Glu Ser Asn Trp Asp Pro Ser Asn Asp Pro Ser Phe Gln Asp Ile
            675                 680                 685
Gly Glu Ala Ala Thr Val Thr Glu Ala Ile Ser Val Tyr Leu Asp Gly
            690                 695                 700
Glu Leu Val Tyr Gly Gln Leu Pro Gly Glu Ser Glu Ser Glu Pro Asp
705                 710                 715                 720
```

```
Asp Thr Thr Ala Pro Thr Ala Pro Ser Asn Leu Ser Val Val Glu Thr
                725                 730                 735

Thr Ala Ser Ser Ala Glu Val Glu Trp Glu Ala Ala Ser Asp Glu Gly
            740                 745                 750

Gly Ser Gly Leu Asp His Tyr Thr Ile Ser Val Ala Gly Asp Phe Asp
        755                 760                 765

Gln Gln Val Gly Ala Gly Thr Thr Thr Ala Thr Val Glu Glu Leu Asp
    770                 775                 780

Ala Glu Thr Thr Tyr Glu Ile Gly Val Ser Ala Val Asp Gly Ala Gly
785                 790                 795                 800

Asn Glu Ser Asp Thr Val Thr Val Glu Ala Thr Thr Asp Glu Ala Asp
                805                 810                 815

Asp Gly Glu Asp Asp Ser Asp Asp Glu Glu Ser Pro Thr Asp Ala Leu
            820                 825                 830

Val Val Asn Asp Tyr Asp Gly Asp Pro Ala Trp Ser Ser Asn Arg Asn
        835                 840                 845

Asp Leu Gly Gln Trp Cys Gly Ala Gly Ser Phe Glu Asn Gly Ala Gly
    850                 855                 860

Glu Val Ala Asp Gly Ala Leu Val Leu Glu Tyr Asp Asn Gly Gly Trp
865                 870                 875                 880

Tyr Gln Glu Gln Ile Asn Arg Asp Val Ser Asp Tyr Ser Ser Val Val
                885                 890                 895

Leu Asp Val Cys Gly Ala Asn Gly Gly Glu Asn Glu Ile Arg Phe
            900                 905                 910

Ala Met Gly Gly Val Ser Gly Leu Leu Gly Asp Leu Thr Gly Asp Ser
        915                 920                 925

Ile Gly Thr Ser Ala Gly Glu Val Arg Ile Asp Met Glu Ser Ala Gly
    930                 935                 940

Ile Asp Pro Thr Ala Glu Gly Leu Ala Val Arg Leu Asn Phe Trp Gln
945                 950                 955                 960

Gly Gly Glu Ser Thr Leu Ala Ile Glu Ala Ile Arg Leu Glu
                965                 970

<210> SEQ ID NO 14
<211> LENGTH: 611
<212> TYPE: PRT
<213> ORGANISM: Halorhabdus utahensis

<400> SEQUENCE: 14

Met Val Lys Arg Arg Thr Val Leu Lys Gly Ser Ile Ala Leu Gly Ser
1               5                   10                  15

Leu Gly Leu Ala Thr Ser Val Leu Gly Gln Glu His Ser Pro Leu Val
            20                  25                  30

Val His Glu Phe Asp Gly Gly Thr Tyr Pro Gly Ser Asn Asp Leu Gly
        35                  40                  45

Asn Trp Ala Asp Ala Gly Ser Phe Ala Asn Gly Ser Gly Ala Gly Glu
    50                  55                  60

Val Glu Asp Gly Ala Leu Arg Leu Glu Tyr Asp Asn Ala Gly Trp Phe
65                  70                  75                  80

Gly Ser Asn Val Ser Gln Ser Ile Asp Asp Tyr Gln Tyr Leu Thr Leu
                85                  90                  95

Arg Ile Arg Gly Asp Asp Gly Gly Glu Ser Asp Phe Arg Leu Lys
            100                 105                 110

Ile Gly Gly Ala Ser Asp Leu Leu Glu Asn Leu Thr Asp Asp Ser Ile
```

```
            115                 120                 125
Gly Thr Asp Tyr Ser Thr Val Ser Val Asp Leu Glu Ser Val Gly Ala
130                 135                 140

Asp Arg Glu Asn Pro Gln Ala Val Arg Phe Asn Phe Trp Gln Gly Ala
145                 150                 155                 160

Ser Gly Ala Val Glu Ile Asp Arg Ile Ala Val Thr Thr Asp Pro Asp
                165                 170                 175

Asp Asp Gly Ser Glu Thr Pro Thr Glu Thr Pro Glu Asp Thr Pro Thr
                180                 185                 190

Glu Thr Pro Glu Asp Thr Pro Thr Glu Thr Pro Glu Asp Thr Pro Thr
                195                 200                 205

Glu Glu Pro Asp Asp Asp Gly Glu Pro Thr Trp Asp Val Pro Phe
210                 215                 220

Pro Asp Arg Pro Pro Glu Pro Asp Thr Leu Pro Ser Asp Ile Thr Gly
225                 230                 235                 240

Ser Thr Thr Val Ala Glu Leu Tyr Glu His Phe Asp Asp Pro Tyr Tyr
                245                 250                 255

Val Pro Arg Asp Phe Thr Asp Tyr Leu Pro Gly Glu Thr Ser Ser Thr
                260                 265                 270

Gly Gln Thr Trp Thr Asp Ala Glu Lys Ala Glu Phe Asn Tyr Asp
                275                 280                 285

Val Glu Ala Val Gln Asn Asn Ile Ser Asp Gly Ser Leu Thr Leu Asp
290                 295                 300

Gln Leu Gly Thr Gln Ala Leu Pro Tyr Val Gln Gln Leu Ala Asp Asn
305                 310                 315                 320

Asp Phe Pro Ala His Ala Thr Val Lys Leu Leu Pro Arg Leu Ala Leu
                325                 330                 335

Leu Pro Asp Glu Thr Glu Asp Pro Gly Thr His Asp Asp Pro Asp Asn
                340                 345                 350

Val Trp Asp Glu Thr Ala Gly Pro Thr Gln Ala Thr Asn Gly Pro Asp
                355                 360                 365

Gln Phe Ile Gln Asp Arg Trp Pro Thr Asp Ala Arg Thr Tyr Gln Pro
370                 375                 380

Asp Glu Val Arg Val Arg Asp Arg Val His Asp Gln Pro Glu Tyr Asp
385                 390                 395                 400

Asp Ser Arg Glu Trp Gly Ser Ser Ala Asp Leu Pro Glu Asp Val Val
                405                 410                 415

Asn Asn Pro Asp Asn Pro Ile His Glu Met Val Ala Asp Lys Val Asp
                420                 425                 430

Pro Arg Thr Gly Glu Ser Leu Gly Gly Asp Gly Phe Thr Ala Asn Ala
                435                 440                 445

Pro Met Glu Ala Ser Val Glu Ile His Glu Asn Gly Gly Tyr Trp
450                 455                 460

Asn Gln Tyr Leu Val Leu Lys Asn Thr Ser Glu Val Pro Tyr Phe Gln
465                 470                 475                 480

Asp Gly Met Val Ile Thr Trp Leu Gly Pro Ser Gly Asp Ala Ala Asn
                485                 490                 495

Leu Ala Asp Gly His Trp Asn Asn Pro His Arg Pro Ser Gln Ser Leu
                500                 505                 510

Gly His Pro Gln Arg Asp Val Ile Glu Val Asn His Pro Asp Tyr Glu
                515                 520                 525

Gly Met Ser Ala Tyr Ala Val Arg Cys Ala Asn His Asp Glu Pro Tyr
                530                 535                 540
```

```
His Met Arg Thr Ile Tyr Pro Asn Gln Gln Val Ala Met Glu Ile Gly
545                 550                 555                 560

Thr Pro Ala Asn Pro Glu Gln Trp Ser Ser Ser Ala Arg Gln Asp
            565                 570                 575

Leu Val Asp Thr Met Leu Asp Ser Leu His Val Glu Leu Glu Thr Asn
            580                 585                 590

Leu Ser Arg Asn Asp Arg Leu Ile Asp Ala Ile Asp Leu Lys Tyr Arg
        595                 600                 605

Val Pro Asn
    610

<210> SEQ ID NO 15
<211> LENGTH: 16
<212> TYPE: PRT
<213> ORGANISM: Halorhabdus utahensis

<400> SEQUENCE: 15

Asp Gly Asn Leu Ile Lys Asp Pro Asp Gly Asn Thr Val Thr Leu Arg
1               5                   10                  15

<210> SEQ ID NO 16
<211> LENGTH: 8
<212> TYPE: PRT
<213> ORGANISM: Halorhabdus utahensis

<400> SEQUENCE: 16

Gly Val Asn Ile Ala Asp Pro Lys
1               5

<210> SEQ ID NO 17
<211> LENGTH: 9
<212> TYPE: PRT
<213> ORGANISM: Halorhabdus utahensis

<400> SEQUENCE: 17

Arg Ile Asn Glu Thr Ala Gln Ala Arg
1               5

<210> SEQ ID NO 18
<211> LENGTH: 21
<212> TYPE: PRT
<213> ORGANISM: Halorhabdus utahensis

<400> SEQUENCE: 18

Gly Met Thr Ala Thr Gln Val Ile Asp Met Leu Thr Asp Glu Ser Asn
1               5                   10                  15

Gly Trp Tyr Pro Arg
            20

<210> SEQ ID NO 19
<211> LENGTH: 10
<212> TYPE: PRT
<213> ORGANISM: Halorhabdus utahensis

<400> SEQUENCE: 19

Gly Val Tyr Cys Ile Ile Asp Tyr His Arg
1               5                   10

<210> SEQ ID NO 20
<211> LENGTH: 30
<212> TYPE: PRT
<213> ORGANISM: Halorhabdus utahensis
```

```
<400> SEQUENCE: 20

Asp Val Gln Trp Ala Glu Gly Gln Asp Gly Pro Val Asn Thr Glu Leu
1               5                   10                  15

Gln Asp Glu Val Asp Met Phe Trp Asp Thr Val Ala Pro Arg
            20                  25                  30

<210> SEQ ID NO 21
<211> LENGTH: 6
<212> TYPE: PRT
<213> ORGANISM: Halorhabdus utahensis

<400> SEQUENCE: 21

Pro Val Met Phe Ser Arg
1               5

<210> SEQ ID NO 22
<211> LENGTH: 7
<212> TYPE: PRT
<213> ORGANISM: Halorhabdus utahensis

<400> SEQUENCE: 22

Ser Ala Leu Glu Gln Tyr Arg
1               5

<210> SEQ ID NO 23
<211> LENGTH: 18
<212> TYPE: PRT
<213> ORGANISM: Halorhabdus utahensis

<400> SEQUENCE: 23

Gly Ala Asn Gly Gly Glu Glu Asp Glu Phe Ile Phe Asp Met Gly Gly
1               5                   10                  15

Ala Arg

<210> SEQ ID NO 24
<211> LENGTH: 17
<212> TYPE: PRT
<213> ORGANISM: Halorhabdus utahensis

<400> SEQUENCE: 24

Leu Asn Phe Trp Gln Gly Gly Ser Ser Thr Leu Glu Ile Glu Glu Ile
1               5                   10                  15

Arg
```

METHODS OF HYDROLYZING A CELLULOSE USING HALOPHILIC, THERMOSTABLE AND IONIC LIQUIDS TOLERANT CELLULASES

RELATED PATENT APPLICATIONS

The application claims priority as a divisional application of U.S. patent application Ser. No. 13/493,938, filed Jun. 11, 2012, which claims priority to U.S. Provisional Patent Application Ser. No. 61/495,893, filed Jun. 10, 2011, which are herein incorporated by reference in their entireties.

STATEMENT OF GOVERNMENTAL SUPPORT

The invention was made with government support under Contract No. DE-AC02-05CH11231 awarded by the U.S. Department of Energy. The government has certain rights in the invention.

FIELD OF THE INVENTION

The present invention is in the field of saccharification of biomass.

BACKGROUND OF THE INVENTION

Plant cell walls are composed of crystalline cellulose entangled with hemi-cellulose and lignin, forming a complex matrix rendering plant biomass largely inaccessible to cellulolytic enzymes in the native state. Current methods of lignocellulosic biofuel production typically involve disrupting plant cell walls using high temperatures and/or corrosive chemicals to liberate the polysaccharides and generate a product that is more accessible to hydrolytic saccharification. These pretreatments are costly, inefficient and, in certain cases, are environmentally toxic. It is, therefore, necessary to improve pretreatment methods.

Ionic liquids (ILs) represents a promising solution to the problem of recalcitrant biomass. ILs are nonvolatile salts, typically with melting points under 100° C., and some ILs can efficiently solubilize cellulose, hemicellulose and lignin from plant biomass under moderate temperatures[1-6]. The regeneration of cellulose from ILs can be achieved by adding an anti-solvent, such as water or ethanol, into the solution[7-9]. ILs can be recycled for new rounds of pretreatment. It has been shown that regenerated cellulose after IL pretreatment has reduced crystallinity, and is thus easier for cellulolytic enzymes to access[10-11].

Several improvements are needed in the ionic liquid pretreatment process technology before it is cost effective with other pretreatments that are based on the pulp and paper processing technologies that utilize dilute acids and bases. One of the most important areas for cost reduction is reducing the number of washes required after IL pretreatment. Unfortunately, commercial fungal cellulases are inhibited by some ILs[8, 12-13] and, therefore, require extensive washing after IL pretreatment. Therefore, it is crucial to identify IL-resistant enzymes for digesting cellulose in the presence of ionic liquids to decrease the number of washes required and increase the yields of monomeric sugars.

It has been suggested that ILs inhibit enzymatic activity by disrupting hydrogen bonding and hydrophobic interactions and depriving the water hydration shell of the protein[14-18]. This is similar to the denaturing effect caused by salt on mesophilic proteins. Although it's not clear if salt and ionic liquids denature proteins in identical ways, both create an environment characterized by low-water activity and high ionic strength[14, 19]. Microbes living in extremely high salt environments can possess a cytoplasm containing >3 M salt. Accordingly, such organisms have evolved a unique mechanism to compete with salt for water. In high salt concentrations, proteins contain an excessive number of negatively charged acidic amino acids on their surface, while at the same time having only few basic amino acids and a low hydrophobic amino acid content[20-23]. Among these, the negative charges are the most prominent feature[24-27] and are thought to keep the protein soluble in a high salt solution either by forming a hydrated ion network with cations or by preventing the formation of protein aggregation through electrostatic repulsive charges at the protein surface[25, 28-31]. Theoretically, positive charges on protein surface may have similar effect on protein stability in high salt environments as negative charges. Yet, in nature, majority of the halophilic proteins are enriched with acidic amino acids on the protein surface, suggesting that negatively charged proteins are under positive selection in halophilic microorganisms. In addition, reduced surface area is also important for the protein to remain folded and require less water to form a hydration shell. All of these salt adaptation strategies could be used for enzymes to resist ILs.

SUMMARY OF THE INVENTION

The present invention provides for an isolated or recombinant polypeptide comprising an amino acid sequence having at least 70% identity with the amino acid sequence of a *Halorhabdus utahensis* cellulase, such as Hu-CBH1, wherein said amino acid sequence has a halophilic thermostable and/or thermophilic cellobiohydrolase (CBH) activity. In some embodiments, the polypeptide has a CBH activity that is resistant to up to about 20% of ionic liquids.

The present invention also provides for a composition, such as a solution, comprising the isolated or recombinant polypeptide of the present invention and optionally a salt, such NaCl, an ionic liquid (IL), and/or, an alkaline pH. In some embodiments of the invention, the composition further comprises a biomass comprising cellulose capable of being cleaved by the polypeptide to produce cellobioses.

The present invention provides for a composition comprising an ionic liquid and the polypeptide of the present invention. In some embodiments, the composition comprises a condition whereby the polypeptide is capable of cleaving or hydrolyzing a cellulose to produce cellobioses. In some embodiments, the composition further comprises a cellulose, wherein the polypeptide is capable of hydrolyzing the cellulose. In some embodiments, the composition comprises a pretreatment biomass. In some embodiments, the pretreatment biomass comprises cellulose.

The present invention provides for a method of hydrolyzing a cellulose, comprising: (a) providing a composition of the present invention comprising the polypeptide of the present invention, a suitable salt concentration, an ionic liquid and a cellulose, and (b) incubating the composition for a suitable length of time, such that the cellulose is hydrolyzed by the polypeptide. In some embodiments, the solution comprises a pretreatment biomass.

The present invention provides for a method for converting lignocellulosic biomass to sugars for the production of biofuels. Methods for the pretreatment of biomass and the downstream enzymatic hydrolysis that is required to breakdown the long polymers of cellulose to simpler sugars for biofuels production.

BRIEF DESCRIPTION OF THE DRAWINGS

The foregoing aspects and others will be readily appreciated by the skilled artisan from the following description of illustrative embodiments when read in conjunction with the accompanying drawings.

Figure 8B:
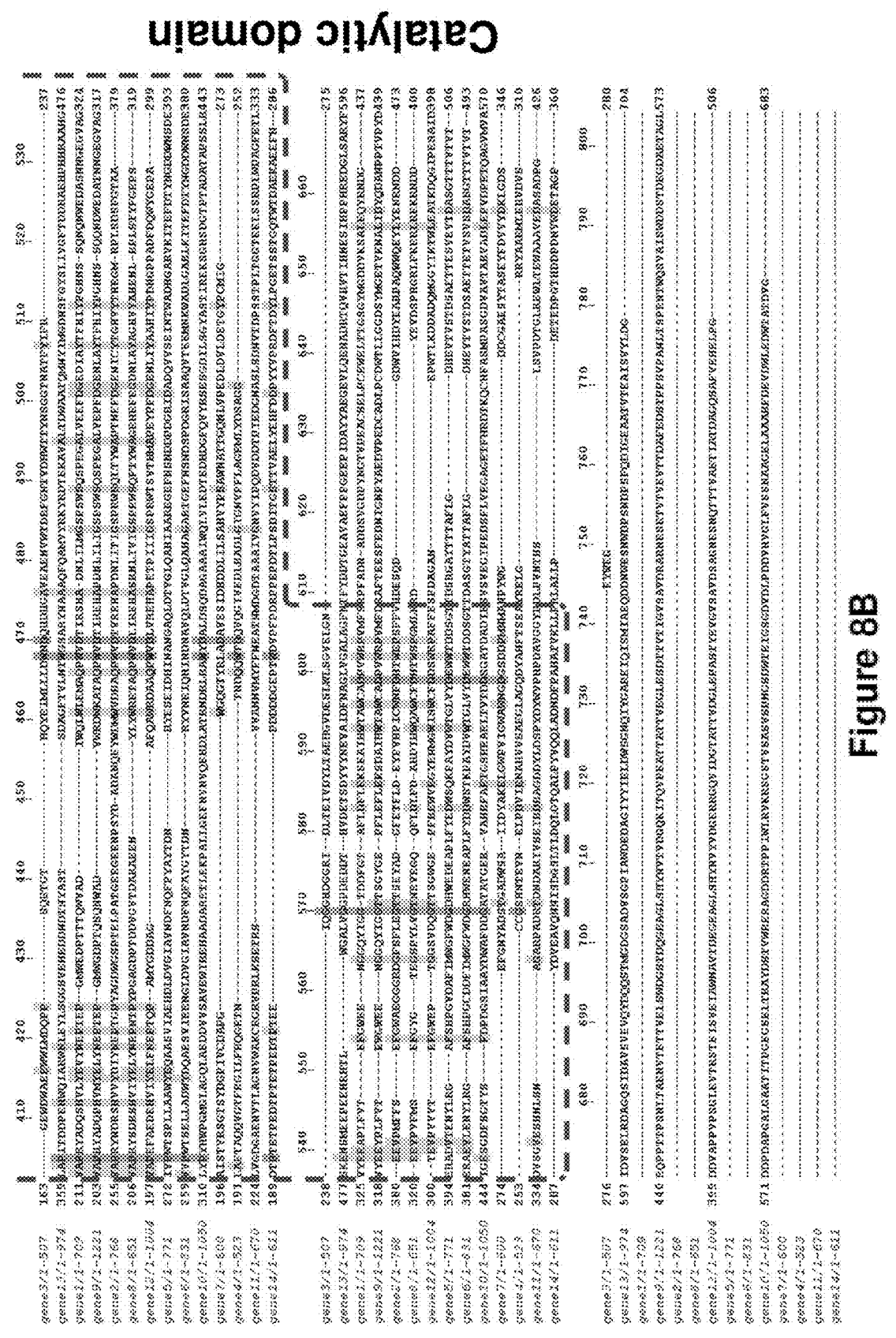

FIG. 8B shows a continuation of the alignment of amino acids sequences from FIG. 8A of putative glycosylhydrolase gene products in the cellulolytic gene cluster of *Halorhabdus utahensis*. Conserved amino acids are highlighted with blue shading. The location of the double arginine signature of a Tat secretion pathway signal motif is marked by double asterisks above the sequences. Catalytic, Fibronectin III (FN3) and Ig-like domains are highlighted by red, yellow and green coloured dash line enclosed regions, respectively.

DETAILED DESCRIPTION OF THE INVENTION

Figure 1:
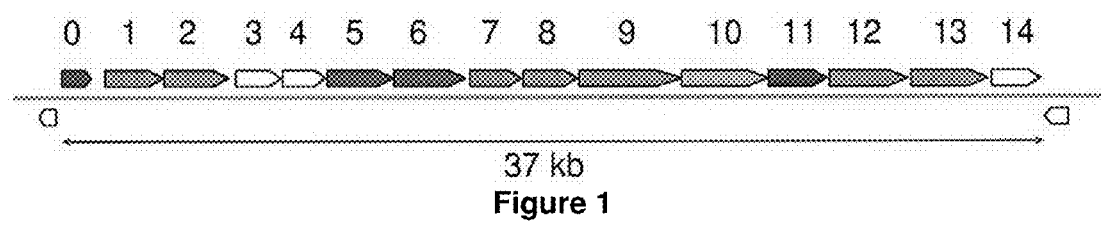
FIG. 1 shows the *Halorhabdus utahensis* genome contains a single gene cluster encoding cellulolytic enzymes with conserved domains. The gene cluster contains 1 sugar specific transcription regulator (in red), 7 cellulase (in green), 2 xylanase (in blue), 1 mannanase (in yellow), 1 pectate lyase (in pink) and 3 proteins with unknown function (in white).

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "IL" includes a single IL compound as well as a plurality of IL compounds, either the same (e.g., the same molecule) or different.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The Polypeptides and Compositions of the Present Invention

The present invention provides for an isolated or recombinant polypeptide comprising an amino acid sequence having at least 70% identity with the amino acid sequence of a *Halorhabdus utahensis* cellulase, such as Hu-CBH1, wherein said amino acid sequence has a halophilic thermostable and/or thermophilic cellobiohydrolase (CBH) activity.

The present invention also provides for a composition, such as a solution, comprising the isolated or recombinant polypeptide of the present invention and optionally a salt, such NaCl, an ionic liquid (IL), and/or, an alkaline pH. In some embodiments of the invention, the composition further comprises a biomass comprising cellulose capable of being cleaved by the polypeptide to produce cellobioses. In some embodiments of the invention, the composition further comprises a high salt concentration, such as equal to or less than about 5 M NaCl. In some embodiments of the invention, the composition further comprises an alkaline concentration, such as equal to or less than about 11.5 pH. In some embodiments of the invention, the composition further comprises an ionic liquid concentration, such as equal to or less than about 20% w/w. In some embodiments of the invention, the polypeptide is highly enriched with negatively charged acidic amino acids on the surface of the polypeptide, which is capable of forming a solvation shell that stabilizes the enzymatic polypeptide, through interaction with salt ions and/or water molecules.

Hu-CBH1 is a heat tolerant haloalkaliphilic cellulase and is active in salt concentrations up to 5 M NaCl. In high salt buffer, Hu-CBH1 can tolerate alkali (pH 11.5) conditions and, more importantly, is tolerant to high levels (20% w/w) of ILs, including 1-allyl-3-methylimidazolium chloride (AMIM Cl). In some embodiments of the invention, the tolerance of the polypeptide to the high heat, alkali and/or IL conditions is salt-dependent.

The present invention provides for a composition comprising an ionic liquid and the polypeptide of the present invention. In some embodiments, the composition comprises a condition whereby the polypeptide is capable of cleaving or hydrolyzing cellulose to produce cellobioses. In some embodiments, the composition further comprises cellulose, wherein the polypeptide is capable of hydrolyzing the cellulose. In some embodiments, the composition comprises a pretreatment biomass. In some embodiments, the pretreatment biomass comprises cellulose.

Figure 7:
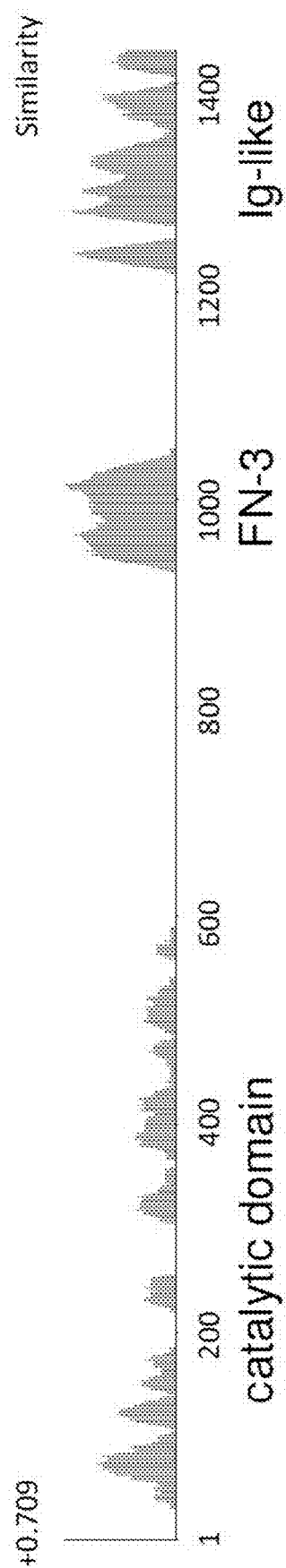
FIG. 7 shows there are 3 conserved domains among the 14 genes of the cellulolytic gene cluster in *Halorhabdus utahensis*. Deduced protein sequences of genes 1 to 14 were aligned by ClustalW. Gaps were allowed. The similarity between the aligned sequences was calculated using a 14 amino acid sliding windows across the entire gene product sequences. Three conserved regions were identified, namely, a catalytic domain, a fibronectin-3 domain (FN-3) and an Ig-like domain.
Figure 8A:
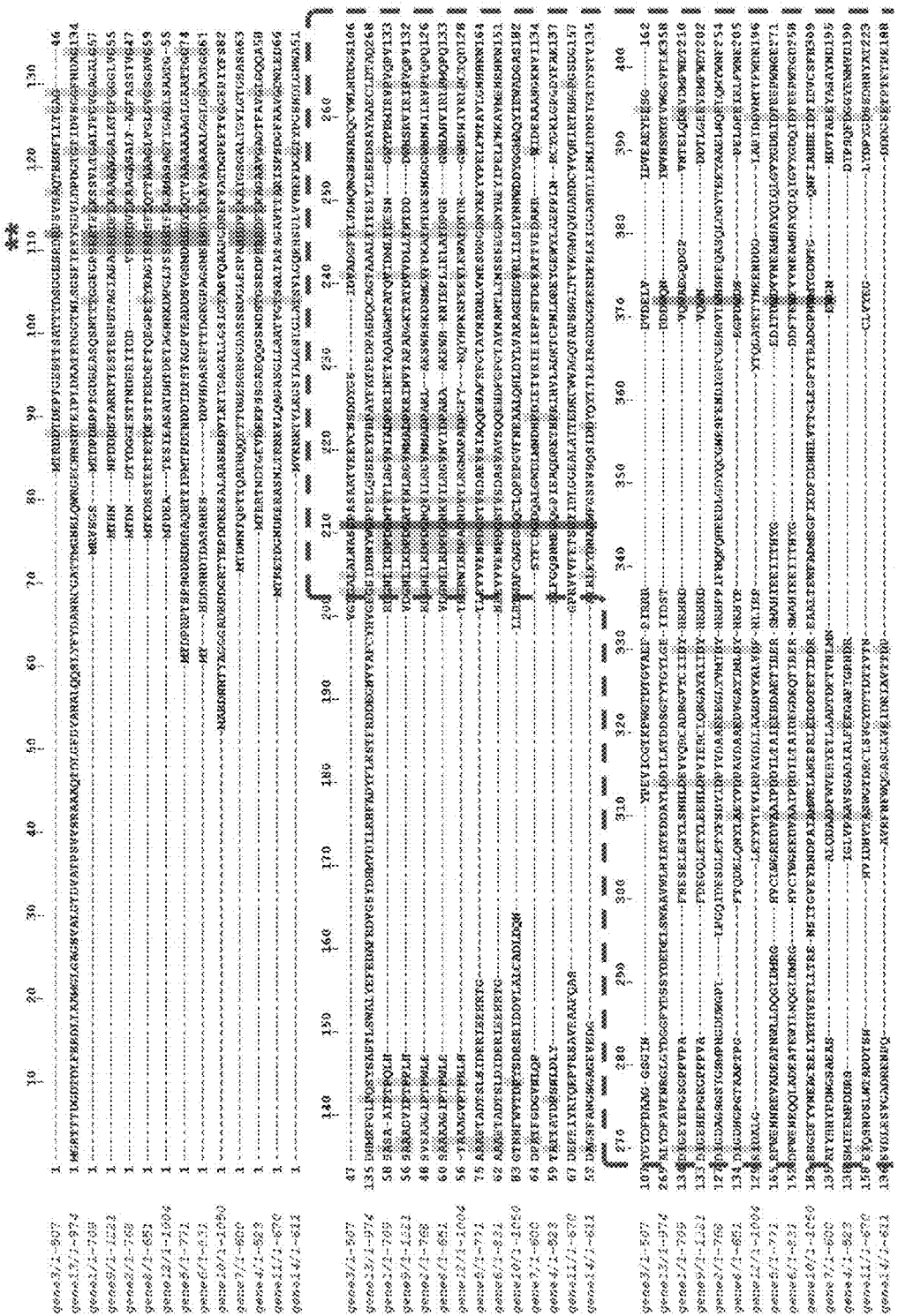
FIG. 8A shows the alignment of amino acids sequences of putative glycosylhydrolase gene products in the cellulolytic gene cluster of *Halorhabdus utahensis* revealed conserved motif and domains. Conserved amino acids are highlighted with blue shading. The location of the double arginine signature of a Tat secretion pathway signal motif is marked by double asterisks above the sequences. Catalytic, Fibronectin III (FN3) and Ig-like domains are highlighted by red, yellow and green coloured dash line enclosed regions, respectively.
Figure 8C:
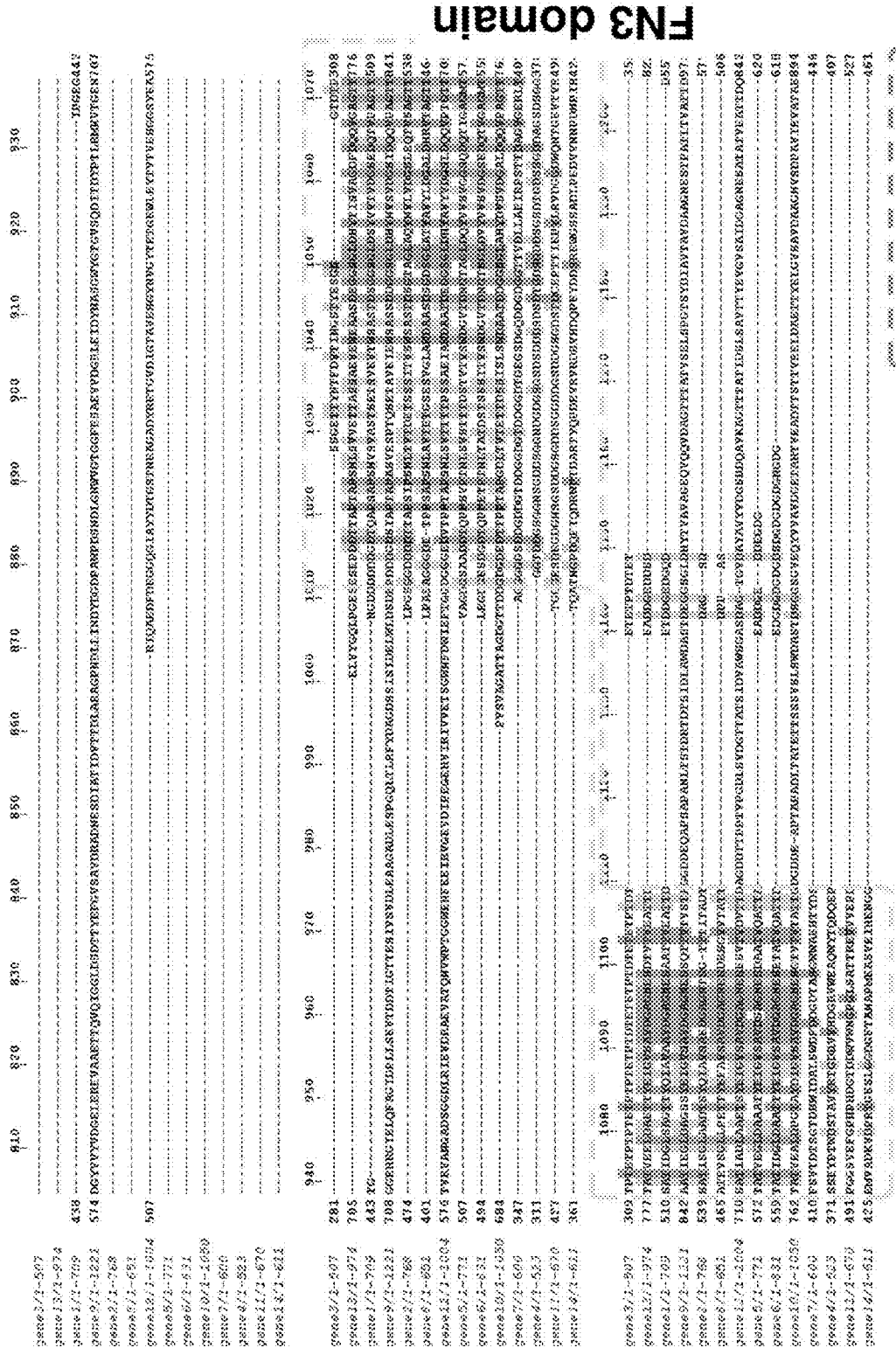
FIG. 8C shows a continuation of the alignment of amino acids sequences from FIG. 8B of putative glycosylhydrolase gene products in the cellulolytic gene cluster of *Halorhabdus utahensis*. Conserved amino acids are highlighted with blue shading. The location of the double arginine signature of a Tat secretion pathway signal motif is marked by double asterisks above the sequences. Catalytic, Fibronectin III (FN3) and Ig-like domains are highlighted by red, yellow and green coloured dash line enclosed regions, respectively.
Figure 8D:
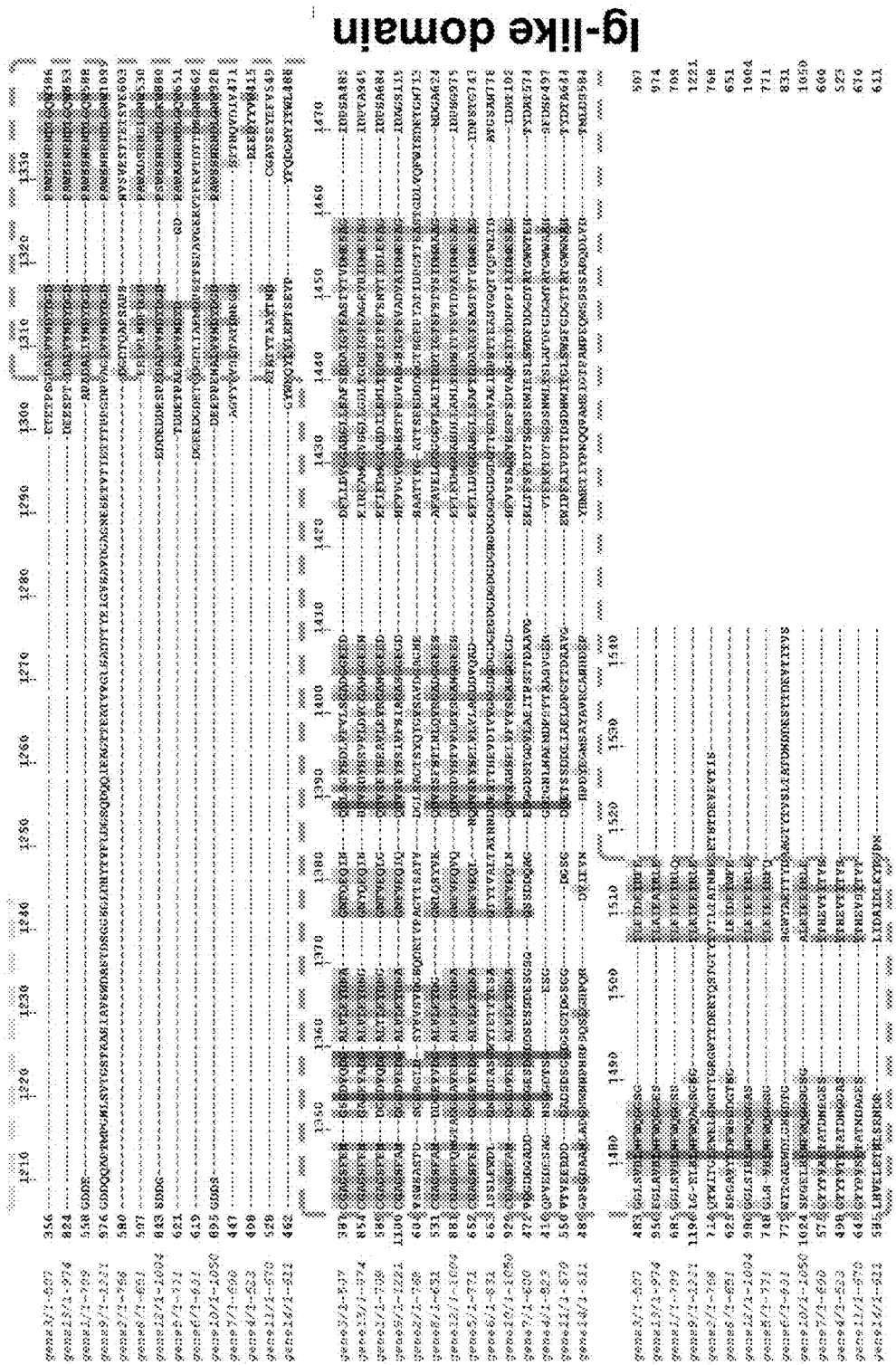
FIG. 8D shows a continuation of the alignment of amino acids sequences from FIG. 8C of putative glycosylhydrolase gene products in the cellulolytic gene cluster of *Halorhabdus utahensis*. Conserved amino acids are highlighted with blue shading. The location of the double arginine signature of a Tat secretion pathway signal motif is marked by double asterisks above the sequences. Catalytic, Fibronectin III (FN3) and Ig-like domains are highlighted by red, yellow and green coloured dash line enclosed regions, respectively.

In some embodiments of the invention, the *Halorhabdus utahensis* cellulase has the amino sequence depicted in SEQ ID NO:1-14. In some embodiments of the invention, the *Halorhabdus utahensis* cellulase has the amino sequence depicted in SEQ ID NO:1, 2, 7, 8, 9, 12, or 13. Hu-CBH1 has the amino acid sequence depicted by SEQ ID NO:1. In some embodiments of the invention, the polypeptide comprises a sequence catalytic domain depicted in FIG. 7. In some embodiments of the invention, the polypeptide comprises an amino acid sequence corresponding to the catalytic domain (as indicated in FIG. 7) of any one of SEQ ID NOs:1-14, or a 70%, 80%, 90%, 95%, or 99% identity thereof. In some embodiments of the invention, the polypeptide comprises the conserved residues of any one of SEQ ID NOs:1-14 as indicated within the catalytic domain (as indicated in FIG. 7). In some embodiments of the invention, the polypeptide comprises an amino acid sequence corresponding to the FN3 domain and/or Ig-like domain (as indicated in FIG. 7) of any one of SEQ ID NOs:1-14, or a 70%, 80%, 90%, 95%, or 99% identity thereof. In some embodiments of the invention, the polypeptide comprises the conserved residues of any one of SEQ ID NOs:1-14 as indicated within the FN3 domain and/or Ig-like domain (as indicated in FIG. 7).

In some embodiments of the invention, the *Halorhabdus utahensis* cellulase comprises the following amino acid sequence:

(SEQ ID NO: 1)
VRVSGSMTDPDRPPTGDREASQSNTTTGGEGPSRRTFLKSSVLTGALTFG

VGAGALGSASAAIPTPQLHRDGNLIKDPDGNTVTLRGVNIADPKRINETA

QARGMTATQVIDMLTDESNGWYPRMIRVPVQPVDIGEYEPGSGPPVPAFN

ESELESYLSNHLDEVVQRCADRGVYCIIDYHRHRDVQWAEGQDGPVNTEL

QDEVDMFWDTVAPRYADQSHVLYEVYNEPTEPGMWEDPTTTQWVADIWQL

WLEMAQPWVDTIRSHADNLILMGSPSWSQSPEGALVEEFDGEDIAYTFHI

YPGHNSSQNQNWEDASNNGEGVAGVYEEAPLFVTEFGWEENGGQYIGGTD

DFGTAFLDFLEKSEAIHWTAWCADPVWRPVMFSRPFADNADDSVGDPYNG

TVPEACSELPCEWELTTGSGYMGDDVKSALEQYRNDGIPGEGTGNGDDDD

DDGDTQAPSAPSNVSVASTSETSVEVTWSASTDSGGSGLDSYVVTVDGSE

DQTVPAGTTSATIDGLSAGTTYQIAVAAVDGAGNESAATTVEATTDETDD

GEDGQDDGDDEAPADALIVNDYDGDPAWSSNRNDLGQWCGAGSFENDGGD

VQDGALTLEYDNGGWFVEQLGQDVSEYSEAVLRVRGANGGEEDEFIFDMG

GARDILSNLTDDSISTSFSNVTIDLESAGIDPSAGGLSVRLNFWQGGSST

LEIEEIRLQ*.

In some embodiments of the invention, the *Halorhabdus utahensis* cellulase comprises the following amino acid sequence:

(SEQ ID NO: 2)
MTDNDTYDGGESTTNDSRIIDDVSRRDVLKAAGASALTAGFASSIVGSVS
AAGIPTPWLERDGNLLRDPDGNQVILRGVNMADPARLARSWRSKDSMGVF
DKATNTDESNDGGWHNNILRVPTQPQDIGDAGSGSIGSMPHGDDWGPLLP
GQIDESDLETYFSDYIDPIVDAAEEEGLYVMIDYHRHFPIFHQPQHEEDL
GDYQCGNESFENDIGFCGERGVLWHSEEQASQLDGYTEEYAAELNQELQM
YWNFVAPRYNDRSHVVYDIYNEPTGPYAGDWGSPTELPATGEEGEENPSY
DADANQEYWDMWVDRAQPWVDTVREHAPDNLITIGSPRWSQLTYWAPTNE
FDGENICYTGHVYTHEGMRPLSDSFGTAAEEVPMFFSEFGWAEGGGRDGF
SFLEGTTSEYADGFETFLDEYPVHPICWNFDHTWEPSFFVHDESQDGDWV
IHDYEARPAQWWQEYLYENRNDDLPGSGGDDDDTTAPSIPSNLTVTDETS
SSITVSWSASTDSGTAGLAQYNVLVDGSLEQTVSAGTTSATISGLAADTS
YQIAVSAEDGAGNTSGTTTITADTDAGSDDGDTQAPSAPSNVSVESTTET
SVEVSWSASTDSGGSGLDSYVVSVDGSQDRTVPAGTTSATVDGLSAGTSY
QIGVSAVDGAGNESAATTVGATTSESDDDDGTSGEPIATIDPGTTSASTG
DLVQFWISDETGNQTWITGLEWELGNGTTGRGWYTDERYQSTGTYTVTLT
ATNNEGETSTDEVEVTIS*.

In some embodiments of the invention, the *Halorhabdus utahensis* cellulase comprises the following amino acid sequence:

(SEQ ID NO: 3)
MTRDDTDEPTGESTTSATTTDSGGRSRDRPSVSAQTRRRFLLTGAGVGLG
ALALNASGPASAATVEEVCNSDDYGSIDVADGFTLVDNQWGNSNADQCVW
LNDDGSYGYDFDAAGGSGINYPEVICGTKPWGTDTGVAEFPIRRRDVDEL
VIDVEAEYSESGGEWDWAEEWWLMDQPPSQETGTHQYEIMLLLDWNDQHD
HGAVEAENVWTDRFGNTVDHWTTYNSGGTNATFYIFRIQGGHDGGRIDLT
EIVDYLTAEHGVDESLWLSGVELGNEYWEGSSGETTYNTFDVTINGSTYE
SGSGTDTPTPTETPTPTETPTPTETPTDTETETPTDTETETPTDTETETP
TDTETETETPSGDALVVNDYDGDPAWSSNRNDLGQWCGAGSFENGSGDVQ
DGALVLEYDNAGWFQEQINQDLSGYSDLVFVLSGADGGEEDDFLLDVGGA
RGLLSAFSDDAIGTSASTVTVDMESAGIDPSAGGLSVRLNFWQGGSGTLE
IDEIRFE*.

In some embodiments of the invention, the *Halorhabdus utahensis* cellulase comprises the following amino acid sequence:

(SEQ ID NO: 4)
MTRRTNDTGEVDEKPSSGAEQQGSNDSTGSRDPSRRDFLKAGAAVGAGTF
AVGLGQQATATTATDPSNLDLYLLFGQSNMEGQGPIEAQDRETHPRIHVL
ADKTCPNLDREYGEWYLAEPPLNRCYGKLGPGDYFAKSMIEEMPDDRSIG
LVPAAVSGADIALFEKGAPIGRNDRDIPSQFDGGYEWMVDLAETAQQVGT
FRGILFHQGETNTNDQQWTDQVQGIVEDLRADLGIGNVPFLAGEMLYDSA
GGCCGSHNTEVNELPDVIENAHVVSAEGLAGQDYAHFTSEAYRELGRRYA
AEMLEHVDVSGGTDDGSGGNSGDDSGGNDGDGSGSDSDDDSDSDTGDSGD
DSGSDTGDSSGDDAGSDSGGSSEYPTWDSTAVYRTGDRVVHDGRVWEAQW
YTQDQEPREEDYYVWQPVEDESAGNSGGDTSGESGGDTGNLNAEMDPSTT
AASVGERVTFRVTDTSGSSNWLTSLAFDFGDGMTATGWWAAHSFDSPGTY
TVTLTATDNGGASTTHEVTITVS*.

In some embodiments of the invention, the *Halorhabdus utahensis* cellulase comprises the following amino acid sequence:

(SEQ ID NO: 5)
VTDPRPTSPSGDRDRRAQHTTIPMTPDTNDDIDTSTAGPVEADDSVGSMD
RRDYLQTVAAAAAAAGLGAATTGGAAAETADTSLSIDERIEEHRTGTLEV
VVENPDGSTVSDAEVSIAQQEHAFSFGTAVNADRLVNESDPGDNYREYVP
ELFNTAVLGNHHKWRFWENNREVADEATNWLLDQGLDMRGHVCLWGREDV
AAIPDDILTAIEERDAETIRERSMAHIEEIITHYGEDITDWDVVNEAMHA
YQLQLGVYGDRIDTEEPWNGEIVPWTSPLLAAWYEQAASVIAEHDLDVGI
AVNDFNQFPYAYTDNRYESEIDHINANGAQLDTVGLQAHIAAREGEFNSN
DDPDGRIDADQVVSEINTWADHGARVKITEFDTYNGDDWNSDEERADVTE
NYLRGAFSHPGVDAFIMWGFWDGDHWEDEAPLFYEDWSQKPAYDVWTGLV
YDEWWTDDSGTTDSRGAYTTTAFLGDHEVTVSTDSAETTESVEVTDASGT
TTVTVTVAGDGSAADDTQPPSVPTNLSVSTTTDSTVTVSWDGVTDNGTAG
LDQYVVSVGGSQDQTIGAGMTTATVEGLDAAATYEIGVSAVDSAGNESDA
ATVQATTAEADDGEDDEGDGTDDETPAEALVVNDYDGDPAWASNRNDLGQ
WCGAGSFENGGGEVEDGALVLEYDNAGWFVEQLNQDVSEYSELVLVLAGD
DVQADEFLLDVGGARGLLSAFTDDAIGTSASTVTVDMESAGIDPSTGGLS
VRLNFWQGGSGTLEIEEIRFQ*.

In some embodiments of the invention, the *Halorhabdus utahensis* cellulase comprises the following amino acid sequence:

(SEQ ID NO: 6)
MTHDDSHDIDASAHESDDVHDASEPTTDGEGPAGSMERRDYLRAVAAAAA
LGGLGGAATGGAAAETADTSLDIDERIEEHRTGNLEVVVENPDGSTVSDA
SVAVSQQEHDFGFGTAVNANTLINSSSEGDNYREYIPELFNKAVMENRHK
WDFWENEQQLADEATEWILNQGLDMRGHVCIWGREDVAAIPDDILTAIDE
GDEQTIRERSMAHIEEIITHYGDDFTEWEVVNEAMHAYQLQIGVYGDQID
TEEPWTGDVVPWTSELLADWYDQAESVIEENGLDVGIAVNDFNQFAYGYT
DNRYVNEIQHINDNAVQLDTVGLQAHAGARTGEFNSNDSPDGRISAAQVT
EEMNKWADLGARLKITEFDTYNGDDWNSDEERAEVLENYLRGAFSHPGCD
DFIMWGFWDGRHWENEAPLFYDDWSTKPAYDVWTGLVYDEWWTDDSGTTD
ASGTYATTAFLGDHEVTVSTDSAETTETVSVSDASGTTTVTVTLEGDGES

-continued

```
DGDTQPPETPTNLTATDSTSSSITVSWDGVTDNGTSGLDVYVVSVDGSED

QTVGAGMTTATIDGLDAATTYEIGVSAVDGAGNESETATVQATTDEDGDG

DGDGDSDGDGDGDGNGDGDGEEDGDETGDGDLIAEMDPSTTSPAVGERVT

FRVTDTTDSGNWISSLEWDLGNGDTASGWYTETTYESAGTYTVALTATNN

DDESTTHEVDIVVGGGDGDGDGEGDGDGDGDGNGDGDGDGDGDGTTGDLV

AEIDPSTTEASVGQTVQFWLTDATGSANWITGAEWDLGNGDTGSGWYAET

TYDAAGTYTVSLTATDNDDESTTDEVTITVS*.
```

In some embodiments of the invention, the *Halorhabdus utahensis* cellulase comprises the following amino acid sequence:

(SEQ ID NO: 7)
```
MTDNNTQSTTQADRQQTTTDRESGRSGDASSSDGLESPARRDVLKAIGSG

ALIGVLGTGSASADPATFGDGVNLQPSYFCDGDQALGWDLMNDHPDIETV

RIEIEPFSFDEVATTVEDAKRWIDEAAANGKNVIATYHHYPDNGSAEASA

LQDAADFWVEHYETLAADTDFTVNLMNEWGNHDVTAEEYASAYNDAISTV

RSGTSYDGPIVCDAPGWGQGTYRLADAVESIDHDDLILSAHVYPSAWNAT

TGQNLVPEDLDVLDETGYPCMIGEFGNYADSTGADWSAIIDYAKELGWPV

IGWAWNGDGSDDPMNMANPYWGDDCGAESYTASEYFDVVYDKLGDSAGGG

GGSDDGDDGTDDGGDGTDDGGDTGEGSDGQDDGDGGTTVDLLAEIRPSTT

DAGVGERLTFSVTDTSGTDRWIDALSWDFDDGDTASGWWAEHTYDSAGTY

TVSLTATDNEGDSTTHQVDIVVGGDDGADDGGGGESDGDDSESSDESGSG

GSSDDQAGEDGGDSTGDVLAEITPSTTDAAVGERLTFSVTDTSGNSRWIE

SLSWDFDDGDTATGWWTEHTYDATGTYTVALTATDNEGESTTHEVTITV

S*.
```

In some embodiments of the invention, the *Halorhabdus utahensis* cellulase comprises the following amino acid sequence:

(SEQ ID NO: 8)
```
MTKDRSTERTETDESTTERDEFTQEGPETYRAGISRRSFLQTTAAAGLVG

LGVGSGAVGSAAAAGIPTPWLEVDGNLLRDPDGNKVILRGVNVIDPARAA

KEWRKNIEPLIELATDPGEGWHAHVIRLPMQPQDIGDHGPGTAAPTPGFT

QDELQNYLAEYVDPAVDAAEDVGAYIMLDYHRHYPEGPDWDSPELDEEIR

LFWNEVAPRYSDRSHVIYELYNEPNTPYPGAGDPTDDVGVTDARAEENYL

YWRETAQPWVDLIREHASRNLIVIGSPRWSOFTYWAGEHEFEGDNLAYAG

HVYAHENLRPLSTYFGEPSEEVPVFMSEFGYGTEGSPYLVGTNEVEGQQF

LDLFDAHDIHWQAWCFDHTWSPGMLNRDYEVDSPHGRLFKERLREKRNDD

LPASAGGGDETPPSAPSNLAVTETGSESVGLAWDAASDSGDSGLATYAVY

LDGALDHRVTAGTTATEVSGLLPETTYEFAVSAVDGAGNESDRSGVVTAT

TDPPASERLVLNDFDGDPAWADSRNELGNWCGAGSFANDDGEVVDGALVL

EYDGGWLQSYVRQDVSSFSTLNLQVRGADGGEESAFAVELGGGGGVLAEI

TDDTIGTSFSTVSIDMAAAGMDGASPGAVYLDFWSGDGTSGTIEIDEIWF

E*.
```

In some embodiments of the invention, the *Halorhabdus utahensis* cellulase comprises the following amino acid sequence:

(SEQ ID NO: 9)
```
MTHNNPDDDSTARRTTESTESPSTAGIASASRRDFLKAAAAGGAIATGFG

GGLVGSAAADVIPTPPLHVDGNLIKDPDGATVNLRGVNMADPKRINVTAP

ARGKTATDVVDLLTNTDDDWHSRVIRIPVQPVDIGEHEPGEGPPPVAFDE

GQLETYLEEHLDPVIERCLQRGAYAIIDYHRHRDVQWNDDTLGEEVEMFW

DTVAPRYADQPHVMYELYNEPTEPGMWGDPTQSQNWADVWRDWKATAQPW

VDTIREHAPDNLILIGSPSWSQSPEGALVEPFDGENLAYTFHIYPGHNSS

QQNDWEDATNNGEGVAGVYEEYPLFVTEWGWEENGGQYIGGTTSGYGEPF

LEFLEKSDAIHWTAWCADPVWRPVMFDRAFTEESFEDNIGNPYAEDVPED

CADLPCDWTLLGGDSYMGETVKNALIDYQDANPPTVPYDEQPPTTPSNLT

AENVTETTVELSWDGSTDQGEAGLSHYNVTVDGQKITQVPEATTATTVEG

LESDTTVTIGVSAVDRARNESETVTVEVTTDAFEDSTPPSVPANLTSPEN

TWQSVAISWDDSTDEGDAETAGLDGYVVYVDGELEREVAAETTQVQIGGL

DSDTTYEFGVSAVDRADNESDIATIDVTTDLARAGPNDLLINDYDGDPAW

PDSNDLGNWVGTGGFESAEVVDGRLEIDYNASGWYGTGVSQDITDYPTLR

MKVTGENGGEHRGIELQFAGIDPLLSEVTDDTIGTTESIVSVDLEAAGAD

LESPGQLTLRFYDAGDSSISIDELWLDSDEPDDDGDSIAPTAPASVESPT

QSETAVEIEWSASSDDGGSGLDHYNVSVDGSIDQQVPAGTTAATIEGLDA

GSSYEIGVSAVDGAGNESSQTTVTVSTAGGDDEQAPSAPANLTSTDRTDT

SIDLAWDASTDEGGSGLDHYTVAVAGEQVQQVDAGTTTATVSELSPGTSY

DIAVTAVDAAGNESTPATLTVATTDGDDQQAPTMPGNLSVTGSTAASIAV

SWDASTDSGGSGLDHYTVFLDGSQDQQIEAGTTEATVVGLSADTTYEIGV

SAVDGAGNESETVTIETTTPPGDPVAGLVVNDYDGDPAWSNHRNDLGNWC

GAGSFANGGGDVEDGALVLEYDNAGWFVEQIQQDVSEYSSIVFSIAGASG

GEGDHFVVGVGGNRSTFSDVADGSIGTSVADVAIDMESAGIDAGSLGELR

LNFWQAGSGSGTLRIEEIRLE*.
```

In some embodiments of the invention, the *Halorhabdus utahensis* cellulase comprises the following amino acid sequence:

(SEQ ID NO: 10)
```
MARDNHTYAGGGADRPDGRTYRPDDRRSALAASRRDVLRTIGAGALLGS

IGTARVQAAPGDREFVATDGPEFTVGGEPIYFSGTNNFWVTDPYSDRSR

IDDVLALCADLDQNLLRTWAFCAGEGGQCLQPEPGVFNEAALQHLDYLV

AKAGEHGVRLILSLVNNWDDYGGMAQYIEWADGASEHGDFYVNEACREL

YRTHVETLLTRENSITGVEYRNDPAIAMWELANEPRLEDDDTETIDDRE

AALTEWFADMSGFIKDFDDNHLVTTGLEGFYTRADGPNWMYGDWTGQNF

IAHHEIDTIDVCSFHLYPYHWPGMGLAGQLAEDDVVSAVEWIREHAADA

RETLEKPALLGEFNVNVQEHDLATRNDRLRAWYDALDSQDAGAAAIWQL

VLEDTEDHDGFQVYRSESGDILSGYASTREKSGHSDGTPTADATAPSSL
```

-continued
RIGESGDFSGTYSFDPDGSIAAYDWAFDDGATATGERVAHRFAETGSHE

AELTVTDDSGATDADIESVSVEGIPEDSFLVEGAGETFHRDTKQCHFAS

MPASGDVAVTARVADLEPVDPETQAGVMVADDPDAPGALGAATITPGEG

SELTRAYDSTVWRERAGDDRTPPIWLRVKRSGSTVSASVSPNGSDWTEI

GSGDVDLPDDVHVGLFVSSNAAGELAAARFDEVDWLEDWTATDVGPVSV

AGATTAGDGTTDDGDGDEDTTPPTAPGDLTVTETTDSSISLSWDAATDD

GGSGLAHYDVSVDGALDQQVPAGTTTATVEALDPGTAYDIGVSAVDGAG

NESGTVTVTATTGDGDDEAPTAPADLTATETTSSSVSLSWDASTDSGGS

GVEQYVVAVDGETAHTVEADTTSTTVEELDAETTYELGVSAVDAAGNVS

DPAVIEVATAEGDDSDEEPPENALVVNDYGDPAWSSNRNDLGNWCGAG

SFANGGGDVEDGALVLEYDNAGWFVEQLNQDVSAHSELVFVVSGASGGE

GDHFVVSAGGVRSRFSDVADGSIDTDPKPIAIDMESAGIDATSPGELRL

NFWQGGSGSGALRIEEIRLE*.

In some embodiments of the invention, the *Halorhabdus utahensis* cellulase comprises the following amino acid sequence:

(SEQ ID NO: 11)
MTRETDGNDRERASNLTRRRVLQAGASGLLAATVGTSALTATAGAVTTA

RISPSDGFAAVGDWLEDDEPEIYRIQEPTRSAVEAAFQASGPRVVVFET

SGTIDLGGEALAITEDKCWVAGQTAPSSGITFVKGMVQVDADDCVVQHI

RTRHGPGSDGEIQSNDSLNTADDTSNNVIDHVTASWGTDECLSVGYDTT

DTTVTNCLVYEGLYDPYGDSSDHNYATLVGDGAENVTLAGNVWAKCRGR

VPRLKSETRSVVANNVMYFFNEATNMDGDTAAAIVGNVYIPQDVDDTPI

EDGNASLSDNVTDPSSTPLTGGTEELSSRPLWPAGFETLDVSGVESHNL

SNAGARPADRTDNDARIVSEIRDRAGDDYLDSPYDYWVPHPDAVGGYPD

LPVNTHSLSVPDTGLREWLTEWAAAVEDASADPGTGGGESDEGDGNSGS

DDGSGDDSGGDDGSDDGSGDSTDCEPTTIEPYLRVDGGDWQNTGEVTVE

PGGSVEFGPHPHDGTDDWVWNGPGLSATTREVVVEPDATATYTAAYTND

CGAVSEYEFVVTVEERDDGADSDSGGDGSGTDGSGGDGSGDDETSSDDL

IAELDPGTTDAAVGEWIPFAIVDTTDSDHWITGLSWSFGDGTTATGWWN

AHTYDTAGTYPVSLTATNDAGESTTHEVSITVT*.

In some embodiments of the invention, the *Halorhabdus utahensis* cellulase comprises the following amino acid sequence:

(SEQ ID NO: 12)
MTDEATESIEASATDHTDETAGNRKDPGLTSSRRTFLGAMASAGTIGAGL

SAATGTAAAGVPTPRLHTEGRWIRDPAGNDVTLRGMAPADPGFYRQYHPK

SFEEVLEWATDTDRGWHPNIVRLPCTQDSIDALGLETYVTEVLRPAVDLL

AARDVYALVDFHLIRPYTQDATETYNEENDDDLAPIDDVMTTFWDRVAPE

FAEDEHVIYELFNEPTQPAMYGDDAGAFQAWRDAAQPWVDLVREHAPETP

IIIGSPRWTSVTHMAPEYPFDGENLIYAAHIYPDNGPPADFDQWYGEPAT

EVPVVVTEFGWEPTGGSVDQGTTSGWGEPFREWVEGYENMGWISWCFDDS

WEPAFFESPDAGANEPWTLKDDADQMGGYIKTWLEATKDQOPESAIDDDV

APPVPSGLEVTRSTEISVEIAWNAVTDEGEAGLSHYNVYVDGERRGQVID

GTATTVDGLEPASTYEVGVSAVDSAGNESNQTTTVAETIATDAGQSAFVE

HELPGRIQAEDFDEGGQGIAYYDTGSTNEAGADYRETGVDIGTAVESGYN

VGYTETGEWLEYTVTVESGGSYEATVRVANGADSGGDLRIEVDRAEVATQ

NVWPTGGWENFEEIRVGEVDIPEGEHVIRIVVETSGWNFDWIEFTGGDGG

GEDVTPPTAPSNLSVTTTTPSSAEIAWDAATDEGGSGLDHYAVYVDGSLD

QQVPTGTTSATIADLAAETSYEIGVSAVDGAGNESESVTVDVTTDAGDDT

TPPTVPGDLSVDGTTATSIDVAWSGASDAGTGVDAYAVYVDGSRDQAVKA

GTTTATIDSLSAVTTYEVGVSAIDGAGNESATATVEATTDQSDDGEDDED

DESPADALVVNDYDGDPSWSSNRNDLGKWCGAGSFQNGTAGGGAVEDGAL

VLEYDNAGWFVEQVQQDVSDYSTVVLRVSGANGGEESEFLFDMGGARDLL

ANLTDDSITTSVTDVAIDMESAGIDPSGGGLSIRLNFWQGGASTLEIEEI

RLE*.

In some embodiments of the invention, the *Halorhabdus utahensis* cellulase comprises the following amino acid sequence:

(SEQ ID NO: 13)
MGRTTTDGDTDLFRRDLLAAMGLGAGSVALGTDVATPSVVSRAAAQTDLG

FDYAHALQQSLYFYDANRCGATTMGNRLQWRGECHHSDTEIPLDAATEDG

GTNLSGSFIEEYSDVLDPDGTGTIDVSGGFHDAGDHMKFGLPQSYSASTL

SWALYEFEDAFRDVGSYDHMVDILRHFADYFLKSTFRDDEGNVVAFCYHV

GEGSIDHNYWGPPELQSSEEYPRPAYFATPEDPASDQCAGTAAALTITSL

VLESEDSAYAAECLDTAQALYDFAVENRGLGYDGGFYDSSYDEDELSWAA

VWLHIATEDDAYLDDILATDDSGTYTGYLGEIIDSTDDDWQNIWVHSWDT

VWGGVFLKLAPITDDPEHWQIARWNLEYLSGGSVEHEDDNDTNYASTSDA

GFTVLNTWGSARYNAAAQFQAMVYRKYRDTEKAVALTDWAATQMNYIMGD

NSFGYSLIVGFTDDHAEHPHHRAAHGSKENSMEEPEEHRHTLWGALVGGP

DEDDTHVDETSDYVYNEVAIDFNAGLVGALAGFNTFYDDTGEAVAEFPPG

EEPIDAYYAEGEVLQENADRTQVRVTIHNESIHPPHREDGLSARYFIDVS

ELRDAGQSIDAVSVEVQYDQQSTMGDGSADVSGPIAWDEDAGIYYIELDW

SGNQIYGAREIQISMIAEQDDNWESNWDPSNDPSFQDIGEAATVTEAISV

YLDGELVYGQLPGESESEPDDTTAPTAPSNLSVVETTASSAEVEWEAASD

EGGSGLDHYTISVAGDFDQQVGAGTTTATVEELDAETTYEIGVSAVDGAG

NESDTVTVEATTDEADDGEDDSDDEESPTDALVVNDYDGDPAWSSNRNDL

GQWCGAGSFENGAGEVADGALVLEYDNGGWYQEQINRDVSDYSSVVLDVC

GANGGEENEIRFAMGGVSGLLGDLTGDSIGTSAGEVRIDMESAGIDPTAE

GLAVRLNFWQGGESTLAIEAIRLE*.

In some embodiments of the invention, the *Halorhabdus utahensis* cellulase comprises the following amino acid sequence:

(SEQ ID NO: 14)
MVKRRTVLKGSIALGSLGLATSVLGQEHSPLVVHEFDGGTYPGSNDLGN

WADAGSFANGSGAGEVEDGALRLEYDNAGWFGSNVSQSIDDYQYLTLRI

RGDDGGEESDFRLKIGGASDLLENLTDDSIGTDYSTVSVDLESVGADRE

NPQAVRFNFWQGASGAVEIDRIAVTTDPDDDGSETPTETPEDTPTETPE

DTPTETPEDTPTEEPDDDDGEPTWDVPFPDRPPEPDTLPSDITGSTTVA

ELYEHFDDPYYVPRDFTDYLPGETSSTGQTWTDAEKAEEFNYDVEAVQN

NISDGSLTLDQLGTQALPYVQQLADNDFPAHATVKLLPRLALLPDETED

PGTHDDPDNVWDETAGPTQATNGPDQFIQDRWPTDARTYQPDEVRVRDR

VHDQPEYDDSREWGSSADLPEDVVNNPDNPIHEMVADKVDPRTGESLGG

DGFTANAPMEASVEIHENGGGYWNQYLVLKNTSEVPYFQDGMVITWLGP

SGDAANLADGHWNNPHRPSQSLGHPQRDVIEVNHPDYEGMSAYAVRCAN

HDEPYHMRTIYPNQQVAMEIGTPANPEQWSSSSARQDLVDTMLDSLHVE

LETNLSRNDRLIDAIDLKYRVPN*.

In some embodiments of the invention, the polypeptide comprises one or more of the following amino acid sequences: DGNLIKDPDGNTVTLR (SEQ ID NO:15), GVNIADPK (SEQ ID NO:16), RINETAQAR (SEQ ID NO:17), GMTATQVIDMLTDESNGWYPR (SEQ ID NO:18), GVYCIIDYHR (SEQ ID NO:19), DVQWAE-GQDGPVNTELQDEVDMFWDTVAPR (SEQ ID NO:20), PVMFSR (SEQ ID NO:21), SALEQYR (SEQ ID NO:22), GANGGEEDEFIFDMGGAR (SEQ ID NO:23), and LNF-WQGGSSTLEIEEIR (SEQ ID NO:24).

Isolated or purified Hu-CBH1 enzyme when incubated with 50 µl of 0.5% soluble carboxymethyl cellulose (CMC) in 200 µl reaction buffer, containing 2 M NaCl and 10 mM Tris-HCl (pH 7.0), at 37° C. for 30 minutes is capable of cleaving or hydrolyzing the CMC to release glucose (as described herein in Example 1). In some embodiments of the invention, the polypeptide has a specific activity, as measured by this method, of equal to or more than 1, 2, 3, or 4 µmol/min/mg (i.e., µmols of glucose released by 1 mg of enzyme per minute).

In some embodiments of the invention, the polypeptide has an enzymatic activity with an optimal temperature of from about 37° C. to about 60° C. in a composition having 1 M NaCl. In some embodiments of the invention, the polypeptide has an enzymatic activity with an optimal temperature of from about 50° C. to about 70° C. in a composition having 2 M NaCl. In some embodiments of the invention, the polypeptide has an enzymatic activity with an optimal temperature of from about 60° C. to about 80° C. in a composition having 3 M NaCl. In some embodiments of the invention, the polypeptide has an enzymatic activity with an optimal temperature of from about 70° C. to about 90° C. in a composition having 5 M NaCl.

In some embodiments of the invention, the polypeptide has an enzymatic activity with an optimal temperature of equal to or more than about 50° C. In some embodiments of the invention, the polypeptide has an enzymatic activity with an optimal temperature of equal to or more than about 60° C. In some embodiments of the invention, the polypeptide has an enzymatic activity with an optimal temperature of equal to or more than about 70° C. In some embodiments of the invention, the polypeptide has an enzymatic activity with an optimal temperature of equal to or more than about 80° C.

In some embodiments of the invention, the composition has a temperature of from about 37° C. to about 90° C. In some embodiments of the invention, the composition has a temperature of from about 50° C. to about 90° C. In some embodiments of the invention, the composition has a temperature of from about 60° C. to about 90° C. In some embodiments of the invention, the composition has a temperature of from about 70° C. to about 90° C. In some embodiments of the invention, the composition has a temperature of from about 80° C. to about 90° C.

In some embodiments of the invention, the composition has a NaCl, or other suitable salt, or mixture thereof, concentration of from more than 0 M to about 5 M. In some embodiments of the invention, the composition has a NaCl, or other suitable salt, or mixture thereof, concentration of from about 0.1 M to about 5 M. In some embodiments of the invention, the composition has a NaCl, or other suitable salt, or mixture thereof, concentration of from about 0.5 M to about 5 M. In some embodiments of the invention, the composition has a NaCl, or other suitable salt, or mixture thereof, concentration of from about 1 M to about 5 M. In some embodiments of the invention, the composition has a NaCl, or other suitable salt, or mixture thereof, concentration of from about 2 M to about 5 M. In some embodiments of the invention, the composition has a NaCl, or other suitable salt, or mixture thereof, concentration of from about 3 M to about 5 M.

In some embodiments of the invention, the composition comprises seawater which would account of essentially all, or substantially all, of the NaCl concentration of the composition.

In some embodiments of the invention, the composition has an alkaline pH. In some embodiments of the invention, the composition has a pH of equal to or more than about 8 pH. In some embodiments of the invention, the composition has a pH of equal to or more than about 9 pH. In some embodiments of the invention, the composition has a pH of equal to or more than about 10 pH. In some embodiments of the invention, the composition has a pH of equal to or more than about 11 pH. In some embodiments of the invention, the composition has a pH of equal to or more than about 12 pH.

Ionic Liquid (IL)

The suitable IL used in the present invention can be any IL suitable for pretreatment of biomass and for the hydrolysis of cellulose by the CBH of the present invention. Suitable IL are taught in ChemFiles (2006) 6(9) (which are commercially available from Sigma-Aldrich; Milwaukee, Wis.). Such suitable IL include, 1-alkyl-3-alkylimidazolium alkanate, 1-alkyl-3-alkylimidazolium alkylsulfate, 1-alkyl-3-alkylimidazolium methylsulfonate, 1-alkyl-3-alkylimidazolium hydrogensulfate, 1-alkyl-3-alkylimidazolium thiocyanate, and 1-alkyl-3-alkylimidazolium halide, wherein an "alkyl" is an alkyl group comprising from 1 to 10 carbon atoms, and an "alkanate" is an alkanate comprising from 1 to 10 carbon atoms. In some embodiments, the "alkyl" is an alkyl group comprising from 1 to 4 carbon atoms. In some embodiments, the "alkyl" is a methyl group, ethyl group or butyl group. In some embodiments, the "alkanate" is an alkanate comprising from 1 to 4 carbon atoms. In some embodiments, the "alkanate" is an acetate. In some embodiments, the halide is chloride.

Such suitable IL include, but are limited to, 1-allyl-3-methylimidazolium acetate (AMIM Acetate), 1-allyl-3-methylimidazolium chloride (AMIM Cl), 1-allyl-3-methylimidazolium hydrogensulfate (AMIM HOSO$_3$), 1-allyl-3-methylimidazolium methylsulfate (AMIM MeOSO$_3$), 1-allyl-3-methylimidazolium ethylsulfate (AMIM EtOSO$_3$), 1-allyl-3-methylimidazolium methanesulfonate (AMIM MeSO$_3$), 1-allyl-3-methylimidazolium tetrachloroaluminate (AMIM AlCl$_4$), 1-ethyl-3-methylimidazolium acetate (EMIM Acetate), 1-ethyl-3-methylimidazolium chloride (EMIM Cl), 1-ethyl-3-methylimidazolium hydrogensulfate (EMIM HOSO$_3$), 1-ethyl-3-methylimidazolium methylsulfate (EMIM MeOSO$_3$), 1-ethyl-3-methylimidazolium ethylsulfate (EMIM EtOSO$_3$), 1-ethyl-3-methylimidazolium methanesulfonate (EMIM MeSO$_3$), 1-ethyl-3-methylimidazolium tetrachloroaluminate (EMIM AlCl$_4$), 1-ethyl-3-methylimidazolium thiocyanate (EMIM SCN), 1-butyl-3-methylimidazolium acetate (BMIM Acetate), 1-butyl-3-methylimidazolium chloride (BMIM Cl), 1-butyl-3-methylimidazolium hydrogensulfate (BMIM HOSO$_3$), 1-butyl-3-methylimidazolium methanesulfonate (BMIM MeSO$_3$), 1-butyl-3-methylimidazolium methylsulfate (BMIM MeOSO$_3$), 1-butyl-3-methylimidazolium tetrachloroaluminate (BMIM AlCl$_4$), 1-butyl-3-methylimidazolium thiocyanate (BMIM SCN), 1-ethyl-2,3-dimethylimidazolium ethylsulfate (EDIM EtOSO$_3$), Tris(2-hydroxyethyl)methylammonium methylsulfate (MTEOA MeOSO$_3$), 1-methylimidazolium chloride (MIM Cl), 1-methylimidazolium hydrogensulfate (MIM HOSO$_3$), 1,2,4-trimethylpyrazolium methylsulfate, tributylmethylammonium methylsulfate, choline acetate, choline salicylate, and the like. The ionic liquid can comprises one or a mixture of the compounds. Further IL are taught in U.S. Pat. No. 6,177,575, which is incorporated by reference.

In some embodiments of the invention, the composition has an IL concentration of more than 0% w/w. In some embodiments, the concentration of IL is equal to or more than 1% w/w, equal to or more than 2% w/w, equal to or more than 3% w/w, equal to or more than 5% w/w, equal to or more than 10% w/w, equal to or more than 15% w/w, or equal to or more than 20% w/w.

In some embodiments of the invention, the IL has a concentration from more than 0% to about 50% w/w. In some embodiments of the invention, the IL has a concentration from more than 0% to about 35% w/w. In some embodiments of the invention, the IL has a concentration from more than 0% to about 20% w/w. In some embodiments of the invention, the IL has a concentration from about 5% to about 20% w/w.

Methods of the Present Invention

The present invention provides for a method of hydrolyzing a cellulose, comprising: (a) providing a composition of the present invention comprising the polypeptide of the present invention, a suitable salt concentration, an ionic liquid and a cellulose, and (b) incubating the composition for a suitable length of time, such that the cellulose is hydrolyzed by the polypeptide. In some embodiments, the solution comprises a pretreatment biomass.

In some embodiments, the pretreatment biomass is a pretreatment cellulose biomass, pretreatment hemicellulose biomass, pretreatment ligno-cellulose biomass, or a mixture thereof.

The present invention provides for a method for converting lignocellulosic biomass to sugars for the production of biofuels. Methods for the pretreatment of biomass and the downstream enzymatic hydrolysis that is required to breakdown the long polymers of cellulose to simpler sugars for biofuels production.

The present invention provides for a method that is compatible with biomass pretreatment with IL.

In some embodiments, the method results in essentially the 100% hydrolysis of the cellulose into cellobioses. In some embodiments, the method results in at least 90% hydrolysis of the cellulose into cellobioses. In some embodiments, the method results in at least 80% hydrolysis of the cellulose into cellobioses. In some embodiments, the method results in at least 70% hydrolysis of the cellulose into cellobioses. In some embodiments, the method results in at least 50% hydrolysis of the cellulose into cellobioses.

Biomass Pretreatment

Biomass or cellulose pretreatment is described in Hermanutz, et al. (2008) Macromol. Symp. 262:23-27, which is incorporated by reference.

The present invention addresses two significant challenges in biomass processing—IL have shown to be very effective in "solubilizing" lignocellulosic biomass. While the solubilized components of biomass—cellulose, hemicellulose and lignin—can be separated by the addition of solvents, it is inherently expensive and time consuming additional step. The polypeptide can tolerate high concentrations of IL can make the process more cost effective in two ways—first, the enzymes can be used directly in the solution of IL and biomass to produce sugars from cellulose; and second, if the cellulose is "crashed out", that is, precipitated from the solution using antisolvents like water and ethanol, with a resulting carryover of the IL, then the enzymes can be used to solubilize the cellulosic sugars without need for further washing to remove the IL.

Applications

The present invention can be used in the hydrolysis of pretreated biomass for the production of sugars from biomass. The sugars can be used in all process that use C6 sugars, such as glucose, as the enzymes and the process has shown to hydrolyze cellulose and the resulting sugars can be used for any intended purpose. The process is of significant interest in biomass processing or biofuels and other biomaterials, paper recycling and pulp processing for paper manufacturing. The present invention can be applied to ILs mediated biomass pretreatment. It can also be used in diluted acids/bases biomass pretreatment for hydrolysis of cellulose in presence of salt. It can be served as additives in detergents, and has wide applications in pulp, paper and textile industries and bioremediation for environment protection.

REFERENCES CITED (1) Wasserscheid, P.; Keim, W. Angew Chem Int Ed Engl 2000, 39, 3772.
(2) Swatloski, R. P.; Spear, S. K.; Holbrey, J. D.; Rogers, R. D. J Am Chem Soc 2002, 124, 4974.
(3) Kilpelainen, I.; Xie, H.; King, A.; Granstrom, M.; Heikkinen, S.; Argyropoulos, D. S. J Agric Food Chem 2007, 55, 9142.
(4) Zavrel, M.; Bross, D.; Funke, M.; Buchs, J.; Spiess, A. C. Bioresour Technol 2009, 100, 2580.
(5) Singh, S.; Simmons, B. A.; Vogel, K. P. Biotechnol Bioeng 2009, 104, 68.
(6) Fort, D. A.; Remsing, R. C.; Swatloski, R. P.; Moyna, P.; Moyna, G.; Rogers, R. D. Green Chemistry 2007, 9, 63.
(7) Fort, D. A.; Swatloski, R. P.; Moyna, P.; Rogers, R. D.; Moyna, G. Chem Commun (Camb) 2006, 714.
(8) Zhao, H.; Jones, C. L.; Baker, G. A.; Xia, S.; Olubajo, O.; Person, V. N. J Biotechnol 2009, 139, 47.
(9) Lee, S. H.; Doherty, T. V.; Linhardt, R. J.; Dordick, J. S. Biotechnol Bioeng 2009, 102, 1368.
(10) Dadi, A. P.; Varanasi, S.; Schall, C. A. Biotechnol Bioeng 2006, 95, 904.

(11) Dadi, A. P.; Schall, C. A.; Varanasi, S. *Appl Biochem Biotechnol* 2007, 137-140, 407.
(12) Kamiya, N.; Matsushita, Y.; Hanaki, M.; Nakashima, K.; Narita, M.; Goto, M.; Takahashi, H. *Biotechnol Lett* 2008, 30, 1037.
(13) Turner, M. B.; Spear, S. K.; Huddleston, J. G.; Holbrey, J. D.; Rogers, R. D. *Green Chemistry* 2003, 443.
(14) Park, S.; Kazlauskas, R. J. *Curr Opin Biotechnol* 2003, 14, 432.
(15) Bose, S.; Armstrong, D. W.; Petrich, J. W. *J Phys Chem B* 2010, 114, 8221.
(16) Moniruzzaman, M.; Kamiya, N.; Goto, M. *Org Biomol Chem* 2010, 8, 2887.
(17) Zhao, H.; Olubajo, O.; Song, Z.; Sims, A. L.; Person, T. E.; Lawal, R. A.; Holley, L. A. *Bioorg Chem* 2006, 34, 15.
(18) Constantinescu, D.; Herrmann, C.; Weingartner, H. *Phys Chem Chem Phys* 2010, 12, 1756.
(19) van Rantwijk, F.; Sheldon, R. A. *Chem Rev* 2007, 107, 2757.
(20) Paul, S.; Bag, S. K.; Das, S.; Harvill, E. T.; Dutta, C. *Genome Biol* 2008, 9, R70.
(21) Lanyi, J. K. *Bacteriol Rev* 1974, 38, 272.
(22) Hutcheon, G. W.; Vasisht, N.; Bolhuis, A. *Extremophiles* 2005, 9, 487.
(23) Fukuchi, S.; Yoshimune, K.; Wakayama, M.; Moriguchi, M.; Nishikawa, K. *J Mol Biol* 2003, 327, 347.
(24) Frolow, F.; Harel, M.; Sussman, J. L.; Mevarech, M.; Shoham, M. *Nat Struct Biol* 1996, 3, 452.
(25) Tadeo, X.; Lopez-Mendez, B.; Trigueros, T.; Lain, A.; Castano, D.; Millet, O. *PLoS Biol* 2009, 7, e1000257.
(26) Coquelle, N.; Talon, R.; Juers, D. H.; Girard, E.; Kahn, R.; Madern, D. *J Mol Biol* 2010, 404, 493.
(27) Zaccai, G. *Philos Trans R Soc Lond B Biol Sci* 2004, 359, 1269.
(28) Zaccai, G.; Cendrin, F.; Haik, Y.; Borochov, N.; Eisenberg, H. *Journal of Molecular Biology* 1989, 208, 491.
(29) Ebel, C.; Costenaro, L.; Pascu, M.; Faou, P.; Kernel, B.; Proust-De Martin, F.; Zaccai, G. *Biochemistry* 2002, 41, 13234.
(30) Mevarech, M.; Frolow, F.; Gloss, L. M. *Biophys Chem* 2000, 86, 155.
(31) Ebel, C.; Faou, P.; Kernel, B.; Zaccai, G. *Biochemistry* 1999, 38, 9039.
(32) Waino, M.; Tindall, B. J.; Ingvorsen, K. *Int J Syst Evol Microbiol* 2000, 50 Pt 1, 183.
(33) Wu, D.; Hugenholtz, P.; Mavromatis, K.; Pukall, R.; Dalin, E.; Ivanova, N. N.; Kunin, V.; Goodwin, L.; Wu, M.; Tindall, B. J.; Hooper, S. D.; Pati, A.; Lykidis, A.; Spring, S.; Anderson, I. J.; D'Haeseleer, P.; Zemla, A.; Singer, M.; Lapidus, A.; Nolan, M.; Copeland, A.; Han, C.; Chen, F.; Cheng, J. F.; Lucas, S.; Kerfeld, C.; Lang, E.; Gronow, S.; Chain, P.; Bruce, D.; Rubin, E. M.; Kyrpides, N. C.; Klenk, H. P.; Eisen, J. A. *Nature* 2009, 462, 1056.
(34) Waino, M.; Ingvorsen, K. *Extremophiles* 2003, 7, 87.
(35) Bakke, P.; Carney, N.; Deloache, W.; Gearing, M.; Ingvorsen, K.; Lotz, M.; McNair, J.; Penumetcha, P.; Simpson, S.; Voss, L.; Win, M.; Heyer, L. J.; Campbell, A. M. *PLoS One* 2009, 4, e6291.
(36) Little, E.; Bork, P.; Doolittle, R. F. *J Mol Evol* 1994, 39, 631.
(37) Kataeva, I. A.; Seidel, R. D., 3rd; Shah, A.; West, L. T.; Li, X. L.; Ljungdahl, L. G. *Appl Environ Microbiol* 2002, 68, 4292.
(38) Liu, H.; Pereira, J. H.; Adams, P. D.; Sapra, R.; Simmons, B. A.; Sale, K. L. *FEBS Lett* 2010, 584, 3431.
(39) Pereira, J. H.; Sapra, R.; Volponi, J. V.; Kozina, C. L.; Simmons, B.; Adams, P. D. *Acta Crystallogr D Biol Crystallogr* 2009, 65, 744.
(40) Natale, P.; Bruser, T.; Driessen, A. J. M. *Bba-Biomembranes* 2008, 1778, 1735.
(41) Vyazmensky, M.; Barak, Z.; Chipman, D. M.; Eichler, J. *Comp Biochem Physiol B Biochem Mol Biol* 2000, 125, 205.
(42) Datta, S.; Holmes, B.; Park, J. I.; Chen, Z. W.; Dibble, D. C.; Hadi, M.; Blanch, H. W.; Simmons, B. A.; Sapra, R. *Green Chemistry* 2010, 12, 338.
(43) Shill, K.; Padmanabhan, S.; Xin, Q.; Prausnitz, J.; Clark, D. S.; Blanch, H. W. *Biotechnol Bioeng* 2011, 108, 511-520.
(44) Wu, J.; Zhang, J.; Zhang, H.; He, J.; Ren, Q.; Guo, M. *Biomacromolecules* 2004, 5, 266.
(45) Zhu, S. D.; Wu, Y. X.; Chen, Q. M.; Yu, Z. N.; Wang, C. W.; Jin, S. W.; Ding, Y. G.; Wu, G. *Green Chemistry* 2006, 8, 325.
(46) Vreeland, R. H.; Piselli, A. F., Jr.; McDonnough, S.; Meyers, S. S. *Extremophiles* 1998, 2, 321.
(47) Rohban, R.; Amoozegar, M. A.; Ventosa, A. *J Ind Microbiol Biotechnol* 2009, 36, 333.
(48) Rees, H. C.; Grant, S.; Jones, B.; Grant, W. D.; Heaphy, S. *Extremophiles* 2003, 7, 415.
(49) Voget, S.; Steele, H. L.; Streit, W. R. *J Biotechnol* 2006, 126, 26.
(50) Gao, Z.; Ruan, L.; Chen, X.; Zhang, Y.; Xu, X. *Appl Microbiol Biotechnol* 2010, 87, 1373.
(51) Taupin, C. M.; Hartlein, M.; Leberman, R. *Eur J Biochem* 1997, 243, 141.
(52) Cendrin, F.; Chroboczek, J.; Zaccai, G.; Eisenberg, H.; Mevarech, M. *Biochemistry* 1993, 32, 4308.
(53) Zhou, W.; Irwin, D. C.; Escovar-Kousen, J.; Wilson, D. B. *Biochemistry* 2004, 43, 9655.
(54) Bayer, E. A.; Lamed, R.; White, B. A.; Flint, H. *J. Chem Rec* 2008, 8, 364.
(55) Hakamada, Y.; Hatada, Y.; Koike, K.; Yoshimatsu, T.; Kawai, S.; Kobayashi, T.; Ito, S. *Biosci Biotechnol Biochem* 2000, 64, 2281.
(56) Endo, K.; Hakamada, Y.; Takizawa, S.; Kubota, H.; Sumitomo, N.; Kobayashi, T.; Ito, S. *Appl Microbiol Biotechnol* 2001, 57, 109.
(57) Hirasawa, K.; Uchimura, K.; Kashiwa, M.; Grant, W. D.; Ito, S.; Kobayashi, T.; Horikoshi, K. *Antonie Van Leeuwenhoek* 2006, 89, 211.
(58) Blecher, O.; Goldman, S.; Mevarech, M. *Eur J Biochem* 1993, 216, 199.
(59) Kaczowka, S. J.; Maupin-Furlow, J. A. *J Bacteriol* 2003, 185, 165.
(60) Cline, S. W.; Lam, W. L.; Charlebois, R. L.; Schalkwyk, L. C.; Doolittle, W. F. *Can J Microbiol* 1989, 35, 148.
(61) Ghose, T. K. *Pure & Appl. Chem.* 1987, 59, 257.
(62) Arnold, K.; Bordoli, L.; Kopp, J.; Schwede, T. *Bioinformatics* 2006, 22, 195.
(63) Kiefer, F.; Arnold, K.; Kunzli, M.; Bordoli, L.; Schwede, T. *Nucleic Acids Res* 2009, 37, D387.
(64) Peitsch, M. C. *Bio-Technol* 1995, 13, 723.
(65) Dolinsky, T. J.; Nielsen, J. E.; McCammon, J. A.; Baker, N. A. *Nucleic Acids Research* 2004, 32, W665.
(66) The PyMOL Molecular Graphics System, version 1.2r2, Schrödinger, LLC.
(67) Baker, N. A.; Sept, D.; Joseph, S.; Holst, M. J.; McCammon, J. A. *P Natl Acad Sci USA* 2001, 98, 10037.
(68) Gutowski, K. E.; Broker, G. A.; Willauer, H. D.; Huddleston, J. G.; Swatloski, R. P.; Holbrey, J. D.; Rogers, R. D. *J Am Chem Soc* 2003, 125, 6632.

The above references are incorporated by reference as though each is individually and specifically incorporated by reference.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Identification of a Haloalkaliphilic and Thermostable Cellulase with Improved Ionic Liquid Tolerance Some ionic liquids (ILs) have been shown to be very effective solvents for biomass pretreatment. It is known that some ILs can have a strong inhibitory effect on fungal cellulases, making the digestion of cellulose inefficient in the presence of ILs. The identification of IL-tolerant enzymes that could be produced as a cellulase cocktail would reduce the costs and water use requirements of the IL pretreatment process. Due to their adaptation to high salinity environments, halophilic enzymes are hypothesized to be good candidates for screening and identifying IL-resistant cellulases. Using a genome-based approach, we have identified and characterized a halophilic cellulase (Hu-CBH1) from the halophilic archaeon, *Halorhabdus utahensis*. Hu-CBH1 is present in a gene cluster containing multiple putative cellulolytic enzymes. Sequence and theoretical structure analysis indicate that Hu-CBH1 is highly enriched with negatively charged acidic amino acids on the surface, which may form a solvation shell that may stabilize the enzyme, through interaction with salt ions and/or water molecules. Hu-CBH1 is a heat tolerant haloalkaliphilic cellulase and is active in salt concentrations up to 5 M NaCl. In high salt buffer, Hu-CBH1 can tolerate alkali (pH 11.5) conditions and, more importantly, is tolerant to high levels (20% w/w) of ILs, including 1-allyl-3-methylimidazolium chloride ([Amim]Cl). Interestingly, the tolerances to heat, alkali and ILs are found to be salt-dependent, suggesting that the enzyme is stabilized by the presence of salt. Our results indicate that halophilic enzymes are good candidates for the screening of IL-tolerant cellulolytic enzymes.

We have identified a gene cluster that contains multiple cellulolytic enzymes from the halophilic archaeon, *Halorhabdus utahensis*. We cloned and expressed one cellobiohydrolase in a different haloarchaeal host, *Haloferax volcanii*. We named this gene as *Halorhabdus utahensis* CBH1, or Hu-CBH1, in short. Using cellulase activity assay, we found that this enzyme is a haloalkaliphilic and heat tolerant cellobiohydrolase. The protein is enriched in acidic amino acids and presents strong negative charges on its surface. Interestingly, we determined that salt is essential for the stability and function of the protein and that it can tolerate up to 20% (w/w) of ILs, including 1-ethyl-3-methylimidazolium acetate ([Emim]Ac), 1-ethyl-3-methylimidazolium chloride ([Emim]Cl), 1-butyl-3-methylimidazolium chloride ([Bmim]Cl) and 1-allyl-3-methylimidazolium chloride ([Amim]Cl).

Results

*Halorhabdus utahensis* Contains Multiple Cellulase Genes

*Halorhabdus utahensis* is an obligatory halophilic archaeon that requires 27% NaCl for optimal growth[32]. Sequence analysis of its genome revealed that 44 putative glycosyl hydrolases (GH), including cellulases, are encoded (Iain Anderson, et al., manuscript in preparation)[33]. Given the native hypersaline environment of *Hrd. utahensis*, these GHs may include strong candidates for salt-tolerant cellulases. The organism could be cultured on xylan, but not cellulose as substrate, raising the question of whether these cellulase genes are indeed functional[34-35] and/or perhaps incorrectly classified as cellulases.

Seven of the putative cellulase genes are found in a 37 kb genomic locus together with sequences predicted to encode two xylanases, a mannase, a pectinase, a sugar-specific transcription regulator, and three uncharacterized proteins (Table 1). These genes are organized in head to tail orientation (FIG. 1), similar to genes in bacterial operons. Except for the transcription regulator, these genes share three conserved domains, namely a catalytic domain, a fibronectin domain 3 (FN-3) and an Ig-like domain (FIG. 7). These domains are present in both cellulase and non-cellulase genes in the gene cluster. The catalytic domain is less conserved, suggesting that these enzymes serve diverse functions. However, the FN-3 and Ig-like domains are more conserved than the catalytic domain (FIGS. 8A to 8D), In bacteria, FN-3 and Ig-like domains have often been found in glycosyl hydrolase enzymes, suggesting that members in the gene cluster may be involved in carbohydrate metabolic pathways[36-39]. The existence of conserved domains among these genes suggests that the gene cluster was created by gene duplications from one parental gene, and that the functional differences of these genes were acquired later, primarily through mutation of the catalytic domain.

TABLE 1

The Gene IDs from 0 to 14 are assigned based on the position of the genes from beginning to the end of the gene cluster. All genes are in same orientation in the cluster. The predicted protein sequences were used to search NCBI NR protein database. The best hit of the BLAST search was assigned to each gene. Sequence similarity between the predicted genes to their best hits is below or close to 50%.

| Locus Tag | Internal ID | BLAST hits |
| --- | --- | --- |
| Huta_2386 | 0 | Transcriptional regulator (sugar-specific) |
| Huta_2387 | 1 | Cellulase (GH 5) |
| Huta_2388 | 2 | Cellulase (GH 5) |
| Huta_2389 | 3 | Hypothetical protein. |
| Huta_2390 | 4 | Uncharacterized protein |
| Huta_2391 | 5 | Beta-1,4-xylanase |
| Huta_2392 | 6 | Beta-1,4-xylanase |
| Huta_2393 | 7 | Cellulase (GH 5) |
| Huta_2394 | 8 | Cellulase |
| Huta_2395 | 9 | Cellulase |
| Huta_2396 | 10 | Endo-beta-mannanase |
| Huta_2397 | 11 | Pectate lyase |
| Huta_2398 | 12 | Cellulase (GH 5) |
| Huta_2399 | 13 | Cellulase (GH 9) |
| Huta_2400 | 14 | Hypothetical protein |

Figure 9:
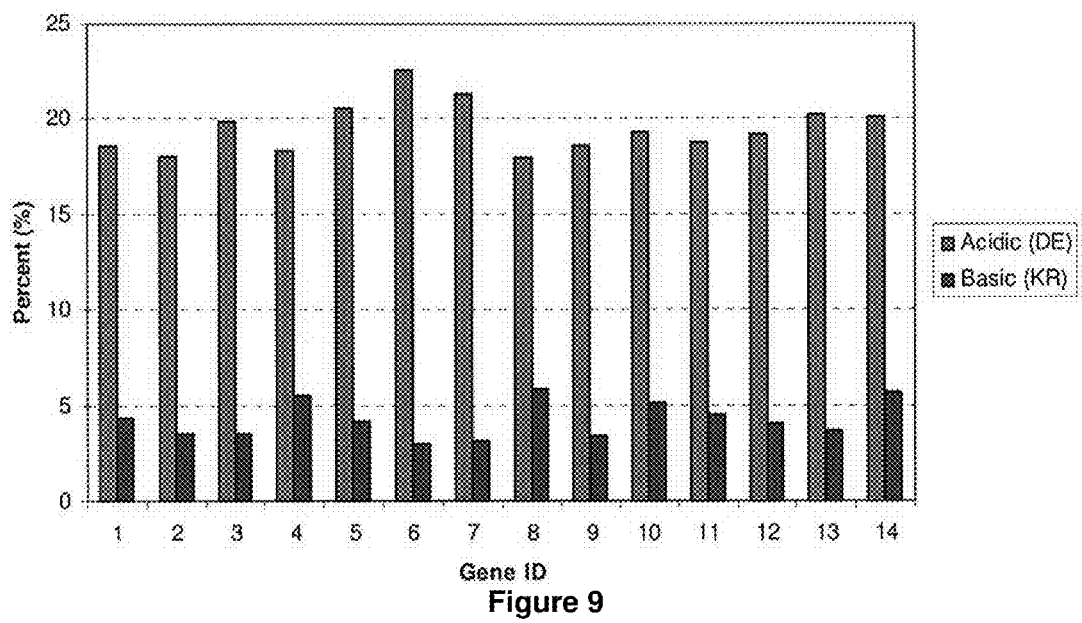
FIG. 9 shows halophilic proteins encoded by the cellulolytic gene cluster are highly enriched with acidic amino acids (Aspartate or D, and Glutamate or E), but significantly deprived of basic amino acids (Arginine or R, and Lysine or L). The percentages of acidic and basic amino acids are shown in blue and red columns, respectively. Gene-1 is identical to Hu-CBH1.

Enrichment of acidic amino acids is a common feature of halophilic proteins. Analysis of the amino acid sequences revealed that proteins from the cellulolytic enzyme gene cluster are enriched with acidic amino acids (FIG. 9). This indicates that these genes have adapted to the high salt environment and are not a result of any recent lateral gene transfer of cellulolytic enzymes from mesophilic organisms. The calculated pI of these proteins is around 4, indicating that these proteins are negatively charged under physiological conditions. To study the function of these genes, we selected Hu-CBH1 (Huta-2387) for our initial work.

The Hu-CBH1 is a Secreted Cellobiohydrolase

Figure 2:
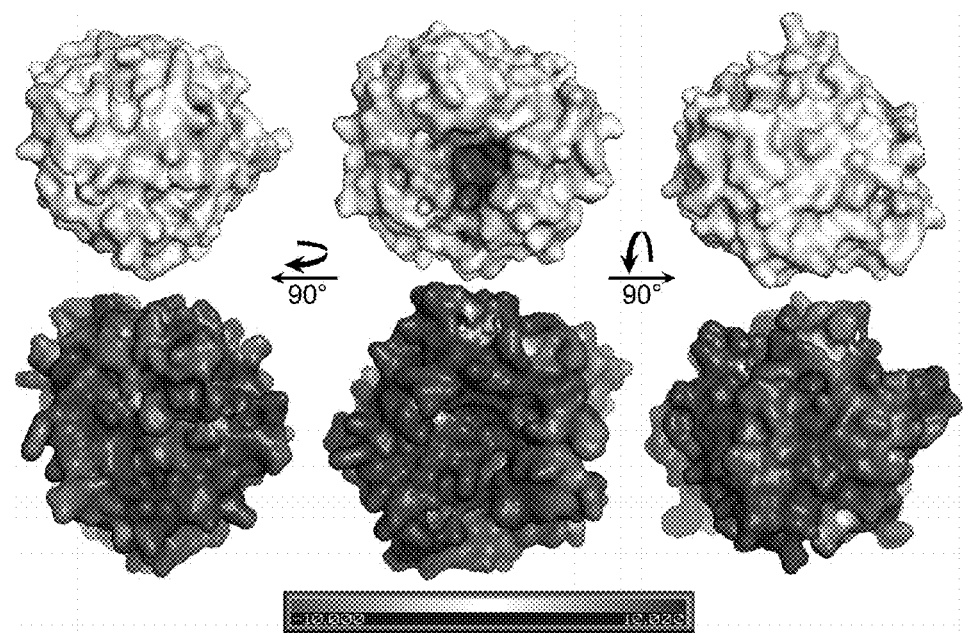
FIG. 2 shows acidic amino acids are highly enriched in halophilic proteins present in the gene cluster. The Hu-CBH1 (gene-1) protein surface is extensively covered by negatively charged amino acids. Electrostatics of the cellulase (neutral protein) from *Erwinia chrysanthemi* (PDB: 1EGZ; top) and the homology model of the cellulase domain of Hu-CBH1 (acidic protein) from *Halorhabdus utahensis* (bottom).
Figure 3A:
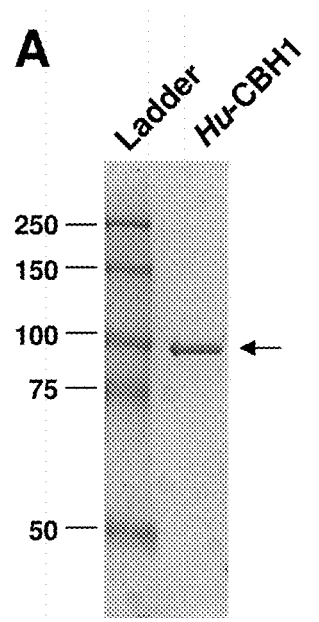
FIG. 3A shows Hu-CBH1 is a secreted protein with cellulase activity. Hu-CBH1 protein bearing a polyhistidine tag was purified from culture medium using Ni-NTA resin and analyzed by SDS-PAGE. The protein migrated as a ~90 kDa band in the gel. The size of protein ladder is in kDa.
Figure 3B:
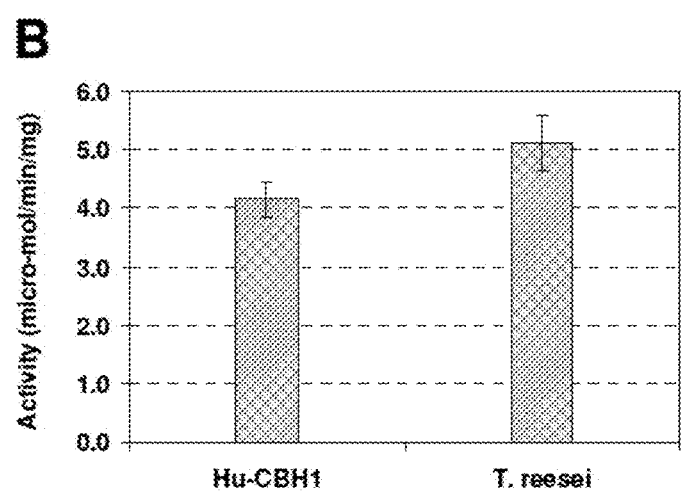
FIG. 3B shows Hu-CBH1 is a secreted protein with cellulase activity. Purified recombinant Hu-CBH1 protein and *T. reesei* cellulase were incubated with carboxymethyl cellulose (CMC) in 2 M NaCl and 10 mM Tris-HCl (pH 7.0) at 37° C. for 30 minutes. The specific activity was measured by the DNS assay, and quantified as μmol of glucose produced per mg of enzyme per minute.

Structure prediction of Hu-CBH1 indicates that the negatively charged amino acids are predominantly present on the protein surface (FIG. 2, bottom). On the contrary, the distribution of acidic amino acids in a mesophilic cellulase homologue from *Erwinia chrysanthemi* is restricted to the catalytic pocket region (FIG. 2, top). Hu-CBH1 bearing a C-terminal 6 His-tag was cloned and expressed in *Haloferax volcanii*, a culturable moderate halophile that is widely use for heterogeneous expression of halophilic proteins. The cells were cultured in a medium containing 20% NaCl, which is required for proper folding of halophilic proteins. The N-terminal region of the Hu-CBH1 protein contains the double arginine-based signature of a TAT secretion pathway signal peptide[40] (FIGS. 8A to 8D). The 709 amino acid sequence predicts a protein of 76 kDa, which was purified from culture medium by binding of the protein to Ni-NTA beads. The secreted protein migrates as a single band of ~90 kDa (FIG. 3A). The identity of the protein was confirmed by mass spectrometry analysis (see Experimental). The apparent slow migration of the protein in SDS PAGE gel was likely caused by the excessive amount of acidic amino acids in the protein[41]. Purified Hu-CBH1 showed comparable enzyme activity to fungal cellulase from *T. reesei*, suggesting that Hu-CBH1 is an active enzyme in this organism (FIG. 3B).

Figure 10:
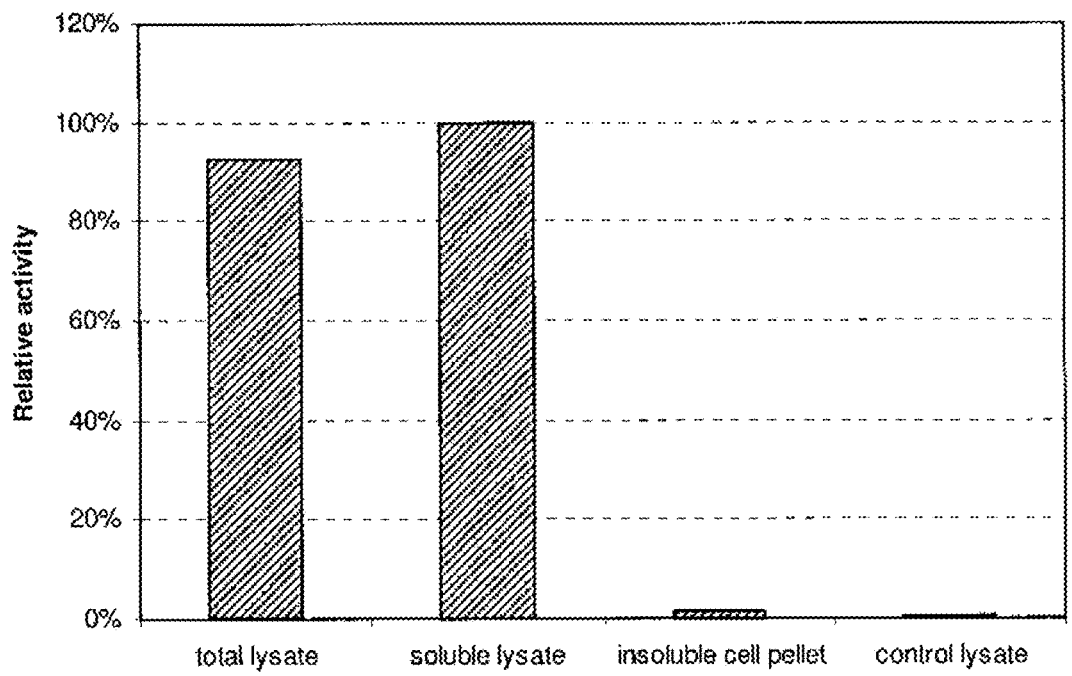
FIG. 10 shows Hu-CBH1 was present in soluble fraction of cell lysate. Recombinant protein was expressed in *Haloferax volcanii* cells. The cells were pelleted, resuspended in lysis buffer (2 M NaCl and 10 mM Tris-HCl (pH 7.0)) and lyzed by sonication. The soluble and insoluble lysate fractions were separated by centrifugation. Control lysate was prepared using cells transformed with the expression vector only. Equal amounts of total lysate from Hu-CBH1-expressing and control cells, and equal proportion of soluble and insoluble fractions of Hu-CBH1 lysate were used as enzyme source in a CMC assay performed in 2 M NaCl and 10 mM Tris-HCl (pH 7.0), at 37° C. for 1 hour. For comparison, the activity of the soluble fraction of Hu-CBH1 lysate was set as 100%.

Enzyme activity on carboxymethyl cellulose (CMC) substrate was also detected in both cell lysate and culture medium. About 39% of the crude enzyme activity was present in culture medium, while 59% of the crude enzyme activity was present in the cell lysate (data not shown). In the cell lysate, the active enzyme was present exclusively in the soluble fraction (FIG. 10). Therefore, the Hu-CBH1 is a soluble protein when expressed in the non-native halophilic host. We have tested the substrate specificity of the enzyme and found that it was only reactive to p-nitrophenyl-beta-D-cellobioside and CMC, suggesting that it is a cellobiohydrolase (Table 2).

TABLE 2

| Polysaccharide subtrate | Total Activity (mM of glucose released) |
|---|---|
| Mannan | ND |
| Carboxymethyl Cellulose | 0.85 |
| p-nitrophenyl-beta-D-glucoside | ND |
| p-nitrophenyl-beta-D-cellobioside | 0.69 |
| p-nitrophenyl-beta-D-xyloside | ND |
| p-nitrophenyl-beta-D-mannoside | ND |

Different polysaccharide substrates were used to determine substrate specificity of the enzyme. Hu-BCH1 was only reactive to carboxymethyl cellulose and p-nitrophenyl-beta-D-cellobioside, suggesting that the enzyme is a cellobiohydrolase.

Hu-CBH1 is a Salt-Dependant Thermal Tolerant Cellulase.

Figure 4A:
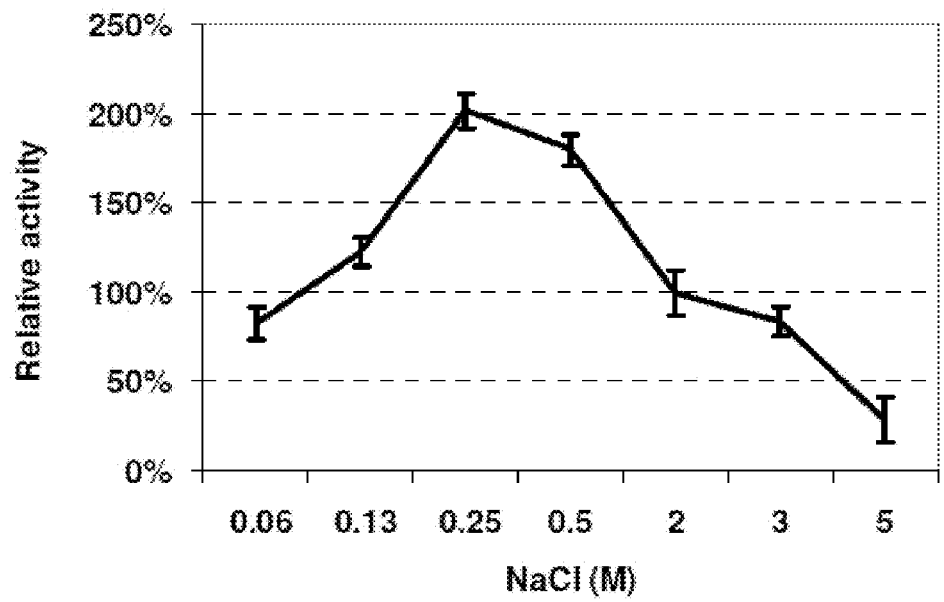
FIG. 4A shows Hu-CBH1 activity and stability are regulated by salt. Hu-CBH1 was used in a CMC assay conducted in different concentrations of NaCl buffer and 10 mM Tris-HCl (pH 7.0), at 37° C. for 1 hour. The enzyme activity in reaction containing 2 M NaCl is set as 100%.
Figure 4B:
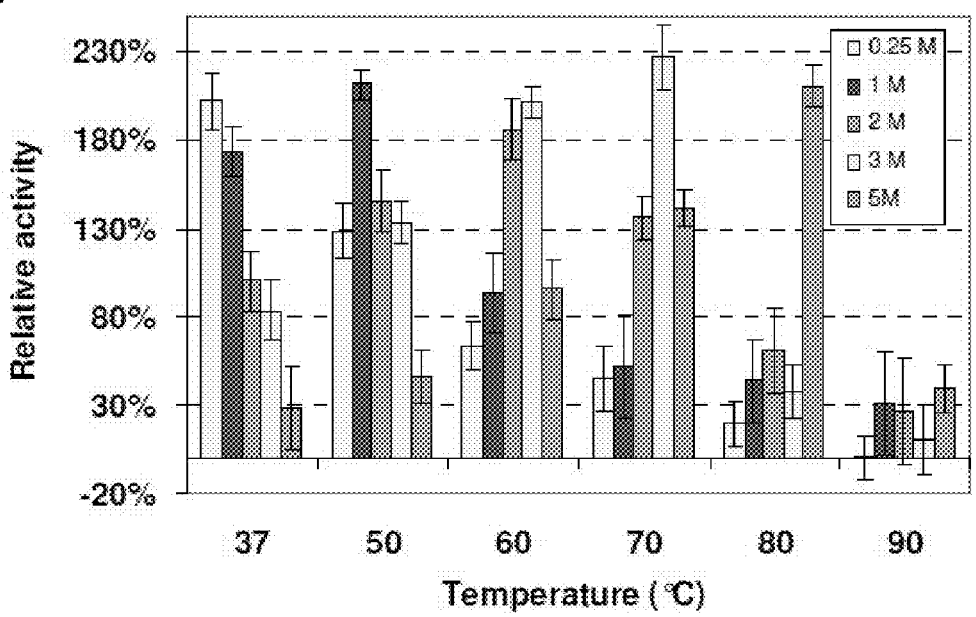
FIG. 4B shows Hu-CBH1 activity and stability are regulated by salt. Hu-CBH1 was used in a CMC assay conducted in different concentrations of NaCl and 10 mM Tris-HCl (pH 7.0) at different temperatures for 1 hour. The activity of reaction in 2 M NaCl at 37° C. was set as 100%.

Many halophilic enzymes require minimum 2 M salt for proper function. However, Hu-CBH1 showed a different level of salt-dependence at different temperatures. At 37° C., the optimal salt concentration of Hu-CBH1 is 0.25 M NaCl (FIG. 4A). However, at 80° C., the optimal salt concentration is 5 M NaCl (FIG. 4B). In low salt buffer, although the enzyme is active at low temperature, its activity was reduced with increasing temperature. This suggests that the enzyme is not stable under low salt conditions. By contrast, in a high salt buffer, activity was stimulated by elevation of temperature but dropped quickly beyond the optimal temperature. The extreme thermal stability is closely correlated with salt concentration, suggesting that salt may help to reinforce the protein structure, probably through forming a salt-ion hydration shell to "lock" the protein in a properly folded structure.

Hu-CBH1 is an Alkaliphilic Cellulase

Figure 5:
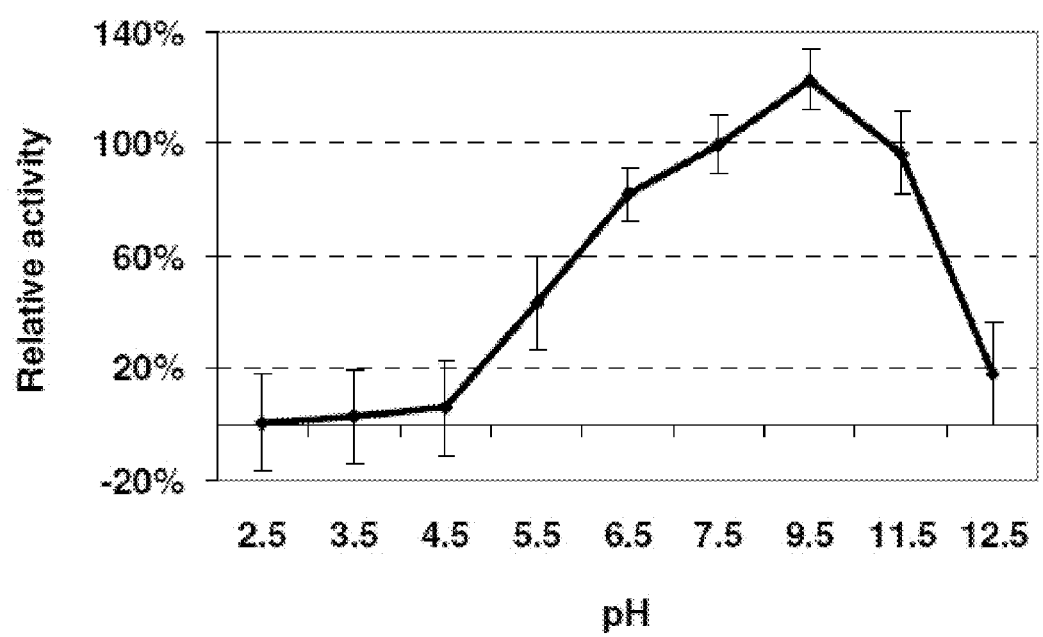
FIG. 5 shows Hu-CBH1 requires high pH for its activity. Hu-CBH1 was used in a CMC assay containing 2 M NaCl, at 37° C., at different pH values for 1 hour. The activity detected at pH 7.5 was set as 100%.
Figure 11:
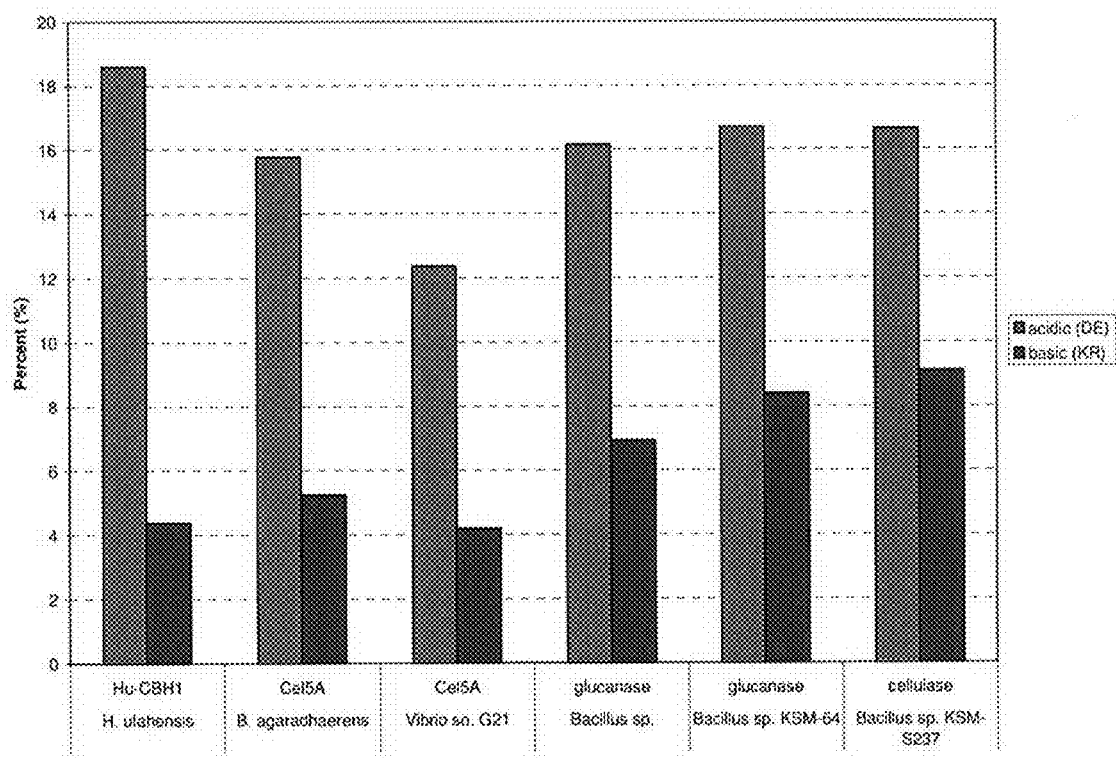
FIG. 11 shows Hu-CBH1 and other 5 known alkaliphilic cellulases are enriched with acidic amino acids. The percentages of acidic and basic amino acids are shown in blue and red bars, respectively. Accession numbers for Cel5A of *B. agaradhaerens*, Cel5A of *Vibrio* so. G21, glucanase of *Bacillus* sp., glucanase of *Bacillus* sp. KSM-64 and alkaline cellulase of *Bacillus* sp. KSM-S237 are O85465, ADJ93836, P19424, AAA73189 and JC7532, respectively.

Since the surface of Hu-CBH1 is negatively charged at physiological pH, we further tested the effect of pH on enzyme activity. In 2M NaCl, the optimal pH of the enzyme was at 9.5, but could tolerate a pH up to 11.5 (FIG. 5). However, the enzyme was very sensitive to low pH, and was completely inactive at pH 4.5. The observed enzyme activity at high pH suggests that maintaining the negative charges on the protein surface is important for enzyme function. Interestingly, some alkaliphilic cellulase proteins are also enriched in acidic amino acids (FIG. 11). Therefore, negatively charged amino acids are selected for proteins in both halophilic and alkaliphilic organisms.

Hu-CBH1 is Resistant to Ionic Liquids

Figure 6A:
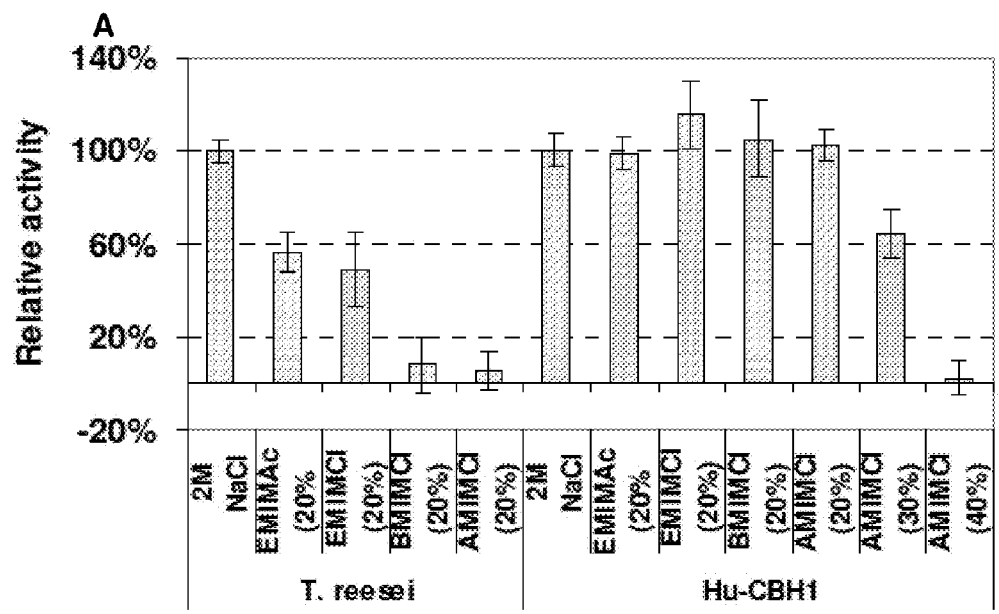
FIG. 6A shows Hu-CBH1 is resistant to high concentrations of ILs in the presence of salt. *T. reesei* cellulase and the Hu-CBH1 were are incubated with CMC substrate at 37° C. for 1 hour in the presence of 2 M NaCl and 10 mM Tris-HCl (pH 7.0), with or without addition of 20% of [Emim]Ac, [Emim]Cl, [Bmim]Cl or 20%, 30% and 40% of [Amim]Cl. The activities in reactions without ILs were set as 100% for both enzymes.
Figure 6B:
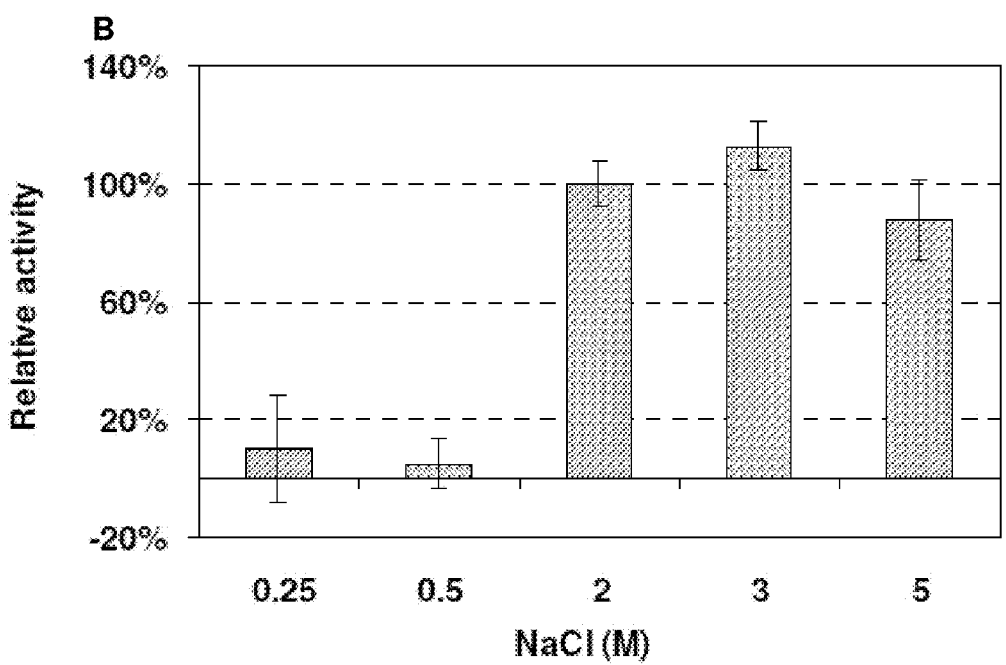
FIG. 6B shows Hu-CBH1 is resistant to high concentrations of ILs in the presence of salt. Hu-CBH1 was incubated with CMC substrates and 20% [Amim]Cl, in the presence of 0.25, 0.5, 2, 3 and 5 M NaCl and 10 mM Tris-HCl (pH 7.0), at 37° C. for 1 hour. The activity of the reaction performed in 2 M NaCl was set as 100%.

Given that Hu-CBH1 is stabilized by salt and is tolerant of high temperatures, we further tested its ability to resist [Emim]Ac, [Emim]Cl, [Bmim]Cl and [Amim]Cl, common choices of ILs for cellulose solvation[3-4, 42-45]. In 20% of [Emim]Ac or [Emim]Cl, *T. reesei* cellulase was partially inhibited (FIG. 6A). However, in 20% of [Bmim]Cl or [Amim]Cl, *T. reesei* cellulase was almost completely inhibited (FIG. 6A). However, Hu-CBH1 activity was unchanged and, sometimes, slightly stimulated in present of 20% of one of these ILs. Therefore, the resistance to ILs is a general character of Hu-CBH1. It should be noted that the activity of Hu-CBH1 in solutions of ILs was also observed to be dependent on salt. In 0.25 M NaCl, Hu-CBH1 was completely inhibited by 20% [Amim]Cl (FIG. 6B), suggesting that the enzyme was not stable in low salt buffer. Interestingly, in high salt buffer, the enzyme activity was not inhibited, but rather stimulated by the presence of [Amim]Cl. This may indicate that [Amim]Cl and NaCl have different effects in terms of protein folding and activity. The reason for which is not clear and requires further investigation. We have tested the upper limit of [Amim]Cl that Hu-CBH1 could tolerate in the presence of 2 M salt. However, further increasing [Amim]Cl concentration in 2M salt buffer caused precipitation of NaCl and hence sharply reduced enzyme activity. In 30% [Amim]Cl, only ~60% of Hu-CBH1 activity was observed. In 40% of [Amim]Cl, the enzyme was completely inactivated. As salt is important for enzyme stability, reducing salt in the reaction might have destabilized the enzyme and reduced its activity in the presence of higher concentrations of ILs.

Discussion

Certain microbes are known to thrive in hypersaline environments. Culturing methods have been used to identify cellulose degrading salt tolerant microbes from salt mines and salt lakes[46-48]. However, none of the cellulase genes were identified. Indeed, detailed characterization of these genes and their products is extremely difficult. Recently, salt-tolerant cellulases have been found by functional screening of recombinant genomic libraries[49-50]. The primary limitation of these studies is that halophilic enzymes may not fold properly when expressed in *E. coli*, and as such are not detectable by functional screening[51-52]. Our study represents the first known case of using a sequence homology-oriented approach for the prediction of halophilic cellulases, and the expression of these salt-tolerant genes in a halophilic host. This strategy enhances the possibility of identifying true obligatory halophilic enzymes.

Like other halophilic proteins, expression products of the cellulolytic gene cluster in Hrd. utahensis are all enriched with acidic amino acids, suggesting that these enzymes are specifically adapted to tolerate and function in the high salt environment. Although their homologies to known collections of fungal glycosylhydrolases are, as expected, low, the operon-like structure of the gene cluster increases the confidence of gene prediction. In addition, the presence of a fibronectin 3 domain in these genes further indicates that they may indeed be involved in lignocellulose metabolism. In bacteria, the FN3 domain is only found in extracellular glycosylhydrolase proteins[36]. It has been shown that this domain is not directly involved in cellulose hydrolysis but rather enhances disruption of the surface of crystalline cellulose and enhances saccharification efficiency[37,53]. The function of the conserved Ig-like domain is unknown, but it may be important for salt-tolerant enzyme function[38-39]. More studies are required for elucidating its function. It remains to be determined whether some of these proteins may form a protein complex for cellulose degradation, similar to cellulosome[54].

Given the importance of the salt hydration shell on protein stability, it is natural that the protein needs to maintain its negative charges in order to resist the denaturing environment created by high salt concentrations. Interestingly, this strategy has also been observed in alkaliphilic proteins that are also enriched with acidic amino acid residues[55-57] and exhibit improved salt-tolerance and salt-dependent thermal stability. This suggests that converged evolution has made these proteins both salt- and alkali-tolerant and as such, could be strong candidates for the discovery of enzymes that can tolerate high concentration of ILs. A recent study demonstrated that hyperthermophilic cellulases are also resistant to ILs, suggesting that there are different mechanisms for extremophiles to maintain their stability in extreme environments[42].

A halophilic host provides an ideal environment for halophilic protein folding. However, growing halophiles takes a long time and requires high levels of salt in the medium. These are technical issues to be overcome before it is possible to produce halophilic enzymes on the large scale. We have expressed Hu-CBH1 in E. coli. The recombinant protein formed insoluble aggregates (data not shown). This may be due to improper folding of protein in the low salt growth conditions required for E. coli. It has been reported that aggregated proteins can be rescued by denaturing the protein in 6 M guanidine hydrochloride or urea followed by renaturing the protein through dilution into salt solutions[58]. It would be interesting to see if such approach can be used to refold Hu-CBH1 proteins produced by E. coli. Nevertheless, understanding the mechanism of salt-tolerance may help to engineer novel cellulolytic enzymes adapted to ionic liquid environments.

EXPERIMENTAL

Cloning and Expression of Hu-CBH1 in a Halophilic Host.

The Hu-CBH1 coding region was amplified by PCR, using genomic DNA of Halorhabdus utahensis (DSM 12940) as template. The coding sequences of six histidines followed by a stop codon were introduced in-frame to the 3'-end of the gene through one of the PCR primers. The PCR products were cloned into the Haloferax volcanii pJAM202 shuttle vector[59]. The plasmids were first transformed and propagated in Escherichia coli cells. The fidelity of the cloned DNA was validated by Sanger sequencing of the plasmids. Later, Hu-CBH1-containing plasmids were transformed into Hfx. volcanii strain WR-340 cells, following the procedure described previously[60]. Positive clones were screened by PCR. The cells were then cultured in liquid halophile culture medium, containing NaCl (206 g), $MgSO_4 \cdot 7H_2O$ (37 g), $MnCl_2$ (75 mg/liter) (1.7 ml), 1M Tris-HCl (pH 7.2) (50 ml), KCl (3.7 g), yeast extract (3 g), tryptone (5 g) and $CaCl_2 \cdot 2H_2O$ (10%) (5 ml) per liter of liquid medium, supplemented with 0.5 µg/ml of novobiocin (final concentration). Cells were cultured at 40° C. with shaking for 6 to 10 days till the cells were confluent.

Recombinant Protein Purification.

Haloferax volcanii cells from 200 ml culture were collected by centrifugation. The supernatant was saved for purifying secreted proteins. The cell pellets were resuspended in 15 ml extraction buffer, containing 2 M NaCl and 10 mM Tris-HCl (pH 7). Cells were broken by acoustic homogenization using a Covaris S220 ultra-sonicator. Cell lysates were spun down by centrifugation at 12,000×g for 15 minutes. The supernatants were separated from cell debris and used for enzyme activity assays.

Hu-CBH1 proteins were purified from culture medium by incubation with Ni-NTA beads (Qiagen). Proteins were eluted with an elution buffer containing 250 mM imidazole, 2 M NaCl and 10 mM Tris-HCl (pH 7). Purified enzymes were quantified using Bradford Protein Assay Kit from Bio-Rad (Cat #500-0001). The yield of purified proteins was 35 µg per 200 ml of culture medium supernatant. The purity and molecular weight of the protein were assessed by electrophoresis in a 7.5% SDS polyacrylamide gel and Coomassie staining.

To confirm the identity of the purified protein, the 90 kDa band was excised from the gel and subject to trypsin digestion and mass spectrometry analysis. A total of 10 unique peptides identical to the Hu-CBH1 protein sequence were identified, namely (1) DGNLIKDPDGNTVTLR (SEQ ID NO:15), (2) GVNIADPK (SEQ ID NO:16), (3) RINTETAQAR (SEQ ID NO:17), (4) GMTATQVIDMLTDESNGWYPR (SEQ ID NO:18), (5) GVYCIIDYHR (SEQ ID NO:19), (6) DVQWAEGQDGPVNTELQDEVDMFWDTVAPR (SEQ ID NO:20), (7) PVMFSR (SEQ ID NO:21), (8) SALEQYR (SEQ ID NO:22), (9) GANGGEEDEFIFDMGGAR (SEQ ID NO:23), and (10) LNFWQGGSSTLEIEEIR (SEQ ID NO:24).

Enzyme Activity Assay

Hu-CBH1 enzymes (2 µg) purified from culture medium or Trichoderma reesei cellulase (Sigma, #C8546) (2 µg) were incubated with 50 µl of 0.5% soluble carboxymethyl cellulose (CMC) in 200 µl reaction buffer, containing 2 M NaCl and 10 mM Tris-HCl (pH 7.0), at 37° C. for 30 minutes. The specific activities of enzymes were determined by measuring the amount of glucose released through enzyme digestion using the DNS assay[61]. The enzyme activity was calculated as mols of glucose released by 1 mg of enzyme per minute.

Lysate supernatants of Hu-CBH1 expressing cells were used to determine enzyme activities in response to changes of temperature, pH and different concentrations of salt and ionic liquids. Briefly, lysate supernatants (50 µl) were mixed with 0.5% soluble carboxymethyl cellulose (CMC) (50 µl) and appropriate buffers (100 µl). Salt and ILs concentrations and pH were adjusted as described in the figure legends. The reactions were incubated for 1 hour, at different temperatures as also described in the figure legends. The amounts of glucose released were determined by the DNS assay. Enzyme activity assays were performed in triplicate for each experimental condition tested. Averaged readings were used to calculate the glucose released by the enzymes. The mock reaction mixtures (without incubation), containing lysate supernatants (50 µl), 0.5% CMC substrates (50 µl) and buffers (100 µl), were used as background controls for each experimental condition tested. The amount of 'glucose' present in the mock reaction mixture was determined by the DNS assay. Background control readings of glucose were subtracted from the enzyme reaction readings to determine the actual amount of glucose released from enzyme hydrolysis reactions. Lysate supernatants of *Haloferax volcanii* cells transformed with control vector showed no cellulase activity.

1-Ethyl-3-methylimidazolium acetate ([Emim]Ac) (#689483), 1-Ethyl-3-methylimidazolium chloride ([Emim]Cl) (#30764), 1-butyl-3-methylimidazolium chloride ([Bmim]Cl) (#94128), 1-Allyl-3-methylimidazolium chloride ([Amim]Cl) (#43961) were purchased from Sigma and used as received.

Assay for Determine Substrate Specificity

The substrate specificity of Hu-CBH1 was determined by assaying against pNPC, pNPX, pNPG, pNPM and Mannan (Sigma, Mo.). The enzymatic reactions (100 µl), containing 4 mM final substrate concentration in 100 mM phosphate buffer (pH 9.5) and 2 M sodium chloride, were incubated for 30 minutes at 37° C. The amount of p-nitrophenol released was measured at 405 nm, after the reaction had been quenched by adding 2 M sodium carbonate, using a molar extinction coefficient of 18,000 $M^{-1}$ $cm^{-1}$. The amount of sugars released when using mannan as substrate was determined by the DNS assay.

Structure of Hu-CBH1

The theoretical structure of the cellulase domain of Hu-CBH1 from *Halorhabdus utahensis* was modeled using the SWISS-MODEL[62-64] server, an automated homology modeling program. The *Pseudoalteromonas haloplanktis* cellulase (PDB: 1TVN) was selected as the template using "Automated Mode". Residues 64 to 382 of Hu-CBH1 aligned to residues 1 to 267 of the template structure with 20.3% sequence identity.

Electrostatics of the model were generated by first removing heteroatoms from the PDB coordinate files for the homology model of the Hu-CBH1 cellulase domain and for the structure of the cellulase (PDB: 1EGZ) from *Erwinia chrysanthemi*. PQR files were generated from the PDB files with PARSE as the forcefield using the program PDB2PQR program[64]. The electrostatics were then calculated in PyMOL[65] using the APBS[66] plug-in with the PDB and PQR files as input. Surface electrostatics were visualized by coloring the PyMOL surface model[67] by the potential on the solvent accessible surface, using $-10\ k_BT/e$ and $+10\ k_BT/e$ as the Low and High surface potentials, respectively.

Conclusions

Our results showed that Hu-CBH1 is clearly a halophilic cellulase. It can function in high salt, it remains active at high temperature, and can tolerate up to 20% (w/w) [Amim]Cl. Structure prediction suggested that the surface of this protein is enriched in acidic amino acids. Our data supports the hypothesis that this negative surface charge may interact with the hydrated salt cations present in the solution to form a hydration shell. This makes the proteins resistant to heat, although neither *Hrd. utahensis* nor *Hfx. volcanii* is typically heat resistant. Indeed, we found that Hu-CBH1 is a salt-dependant enzyme and that its activity can be sustained and stimulated by salt at high temperatures. These results indicate that enzymes isolated from hypersaline environments are strong candidates for the development of IL-tolerant enzymes and cocktails capable of efficiently liberating monomeric sugars from IL-pretreated biomass. Furthermore, it has been recently reported that recovery of ILs from cellulose/ILs solution can be achieved by adding aqueous kosmotropic salt solutions, such $K_3PO_4$[43, 68]. This offers the possibility of integrating IL pretreatment and enzymatic saccharification using halophilic enzymes with minimal washing and high rates of ionic liquid recovery.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of hydrolyzing a cellulose, comprising: (a) providing a composition comprising (i) an isolated or recombinant polypeptide comprising an amino acid sequence having at least 90% identity with the amino acid sequence of SEQ ID NO:1 or SEQ ID NO:5, wherein said isolated or recombinant polypeptide comprises a catalytic domain, a fibronectin domain 3 (FN-3) and an Ig-like domain, and has a halophilic thermostable or thermophilic cellobiohydrolase (CBH) activity, (ii) a suitable salt concentration, (iii) an ionic liquid (IL), and (iv) a cellulose; and (b) incubating the composition for a suitable length of time, such that the cellulose is hydrolyzed by the polypeptide.

2. The method of claim 1, wherein the composition comprises a pretreatment biomass.

3. The method of claim 1, wherein the amino acid sequence has at least 95% identity with the amino acid sequence of SEQ ID NO:1 or SEQ ID NO:5.

4. The method of claim 3, wherein the amino acid sequence has at least 99% identity with the amino acid sequence of SEQ ID NO:1 or SEQ ID NO:5.

5. The polypeptide of claim 4, wherein the amino acid sequence of the polypeptide comprises the amino acid sequence of SEQ ID NO:1 or SEQ ID NO:5.

6. The method of claim 2, wherein the composition has a temperature of from about 37° C. to about 90° C.

7. The method of claim 6, wherein the composition has a temperature of from about 50° C. to about 90° C.

8. The method of claim 7, wherein the composition has a temperature of from about 60° C. to about 90° C.

9. The method of claim 2, wherein the composition has a NaCl, or other suitable salt, or mixture thereof, concentration of from about 0.1 M to about 5 M.

10. The method of claim 9, wherein the composition has a NaCl, or other suitable salt, or mixture thereof, concentration of from about 2 M to about 5 M.

11. The method of claim 2, wherein the composition has a pH of from 7.5 to 12.5.

12. The method of claim 11, wherein the composition has a pH of equal to or more than about 8 pH.

13. The method of claim 2, wherein the composition has a concentration of IL equal to or more than 1% w/w.

14. The method of claim 13, wherein the composition has a concentration of IL of 20 to 30%.

15. The method of claim 2, wherein the composition comprises 1-alkyl-3-alkylimidazolium alkanate, 1-alkyl-3-alkylimidazolium alkylsulfate, 1-alkyl-3-alkylimidazolium methylsulfonate, 1-alkyl-3-alkylimidazolium hydrogensulfate, 1-alkyl-3-alkylimidazolium thiocyanate, or 1-alkyl-3-alkylimidazolium halide, wherein an "alkyl" is an alkyl group comprising from 1 to 10 carbon atoms, and an "alkanate" is an alkanate comprising from 1 to 10 carbon atoms.

16. The method of claim 15, wherein the composition comprises 1-allyl-3-methylimidazolium acetate (AMIM Acetate), 1-allyl-3-methylimidazolium chloride (AMIM Cl), 1-allyl-3-methylimidazolium hydrogensulfate (AMIM HOSO$_3$), 1-allyl-3-methylimidazolium methylsulfate (AMIM MeOSO$_3$), 1-allyl-3-methylimidazolium ethylsulfate (AMIM EtOSO$_3$), 1-allyl-3-methylimidazolium methanesulfonate (AMIM MeSO$_3$), 1-allyl-3-methylimidazolium tetrachloroaluminate (AMIM AlCl$_4$), 1-ethyl-3-methylimidazolium acetate (EMIM Acetate), 1-ethyl-3-methylimidazolium chloride (EMIM Cl), 1-ethyl-3-methylimidazolium hydrogensulfate (EMIM HOSO$_3$), 1-ethyl-3-methylimidazolium methylsulfate (EMIM MeOSO$_3$), 1-ethyl-3-methylimidazolium ethylsulfate (EMIM EtOSO$_3$), 1-ethyl-3-methylimidazolium methanesulfonate (EMIM MeSO$_3$), 1-ethyl-3-methylimidazolium tetrachloroaluminate (EMIM AlCl$_4$), 1-ethyl-3-methylimidazolium thiocyanate (EMIM SCN), 1-butyl-3-methylimidazolium acetate (BMIM Acetate), 1-butyl-3-methylimidazolium chloride (BMIM Cl), 1-butyl-3-methylimidazolium hydrogensulfate (BMIM HOSO$_3$), 1-butyl-3-methylimidazolium methanesulfonate (BMIM MeSO$_3$), 1-butyl-3-methylimidazolium methylsulfate (BMIM MeOSO$_3$), 1-butyl-3-methylimidazolium tetrachloroaluminate (BMIM AlCl$_4$), 1-butyl-3-methylimidazolium thiocyanate (BMIM SCN), 1-ethyl-2,3-dimethylimidazolium ethylsulfate (EDIM EtOSO$_3$), Tris(2-hydroxyethyl)methylammonium methylsulfate (MTEOA MeOSO$_3$), 1-methylimidazolium chloride (MIM Cl), 1-methylimidazolium hydrogensulfate (MIM HOSO$_3$), 1,2,4-trimethylpyrazolium methylsulfate, tributylmethylammonium methylsulfate, choline acetate, choline salicylate, or a mixture thereof.

17. The method of claim 2, wherein the incubating step results in at least 50% hydrolysis of the cellulose into cellobioses.

18. The method of claim 17, wherein the incubating step results in at least 70% hydrolysis of the cellulose into cellobioses.

* * * * *